US011702411B2

(12) United States Patent
Li et al.

(10) Patent No.: US 11,702,411 B2
(45) Date of Patent: Jul. 18, 2023

(54) PYRIDINE, PYRAZINE, AND TRIAZINE COMPOUNDS AS ALLOSTERIC SHP2 INHIBITORS

(71) Applicant: Revolution Medicines, Inc., Redwood City, CA (US)

(72) Inventors: Jie Jack Li, Redwood City, CA (US); Elena S. Koltun, Redwood City, CA (US); Adrian Liam Gill, Redwood City, CA (US); Andreas Buckl, Redwood City, CA (US); Walter Won, Redwood City, CA (US); Naing Aay, Redwood City, CA (US); Kevin Mellem, Redwood City, CA (US); Christos Tzitzilonis, Redwood City, CA (US); Ashutosh Jogalekar, Redwood City, CA (US); James Joseph Cregg, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 0 days.

(21) Appl. No.: 16/845,539

(22) Filed: Apr. 10, 2020

(65) Prior Publication Data
US 2020/0339552 A1  Oct. 29, 2020

Related U.S. Application Data

(63) Continuation of application No. PCT/US2018/055502, filed on Oct. 11, 2018.

(60) Provisional application No. 62/571,760, filed on Oct. 12, 2017, provisional application No. 62/615,353, filed on Jan. 9, 2018, provisional application No. 62/678,889, filed on May 31, 2018.

(51) Int. Cl.
*C07D 407/14* (2006.01)
*C07D 401/04* (2006.01)
*C07D 401/14* (2006.01)

(52) U.S. Cl.
CPC ......... *C07D 407/14* (2013.01); *C07D 401/04* (2013.01); *C07D 401/14* (2013.01)

(58) Field of Classification Search
CPC .............................. C07D 401/14; C07D 491/10
See application file for complete search history.

(56) References Cited

U.S. PATENT DOCUMENTS

| | | | |
|---|---|---|---|
| 2,572,728 A | 10/1951 | Hultquist | |
| 2,636,882 A | 4/1953 | Dunlop et al. | |
| 3,701,779 A | 10/1972 | Donninger et al. | |
| 4,687,848 A | 8/1987 | Brunnmueller et al. | |
| 5,262,564 A | 11/1993 | Kun et al. | |
| 6,921,762 B2 | 7/2005 | Cai | |
| 7,863,288 B2 | 1/2011 | Ibrahim et al. | |
| 8,324,200 B2 | 12/2012 | Li et al. | |
| 8,703,770 B2 | 4/2014 | Coleman et al. | |
| 9,169,261 B2 | 10/2015 | Fan et al. | |
| 9,394,368 B2 | 7/2016 | Brogdon et al. | |
| 10,590,090 B2 | 3/2020 | Jogalekar et al. | |
| 2004/0213795 A1 | 10/2004 | Collins et al. | |
| 2004/0220189 A1 | 11/2004 | Sun et al. | |
| 2006/0189664 A1 | 8/2006 | Barth et al. | |
| 2008/0176309 A1 | 7/2008 | Wu et al. | |
| 2009/0325973 A1* | 12/2009 | Watterson | A61P 31/04 514/252.02 |
| 2010/0190980 A1 | 7/2010 | Umemiya et al. | |
| 2011/0257184 A1 | 10/2011 | Qu et al. | |
| 2012/0034186 A1 | 2/2012 | Wu et al. | |
| 2012/0065205 A1* | 3/2012 | Mercer | C07D 401/04 514/235.8 |
| 2012/0266264 A1 | 10/2012 | Lee | |
| 2012/0330012 A1 | 12/2012 | Frank et al. | |
| 2013/0005949 A1 | 1/2013 | Fertig et al. | |
| 2014/0154179 A1 | 6/2014 | Fan et al. | |
| 2016/0031976 A1 | 2/2016 | Seubert et al. | |
| 2017/0042881 A1 | 2/2017 | Fagin et al. | |
| 2018/0200381 A1 | 7/2018 | Kannan | |
| 2019/0210977 A1 | 7/2019 | Jogalekar et al. | |
| 2019/0290649 A1* | 9/2019 | Xie | C07D 401/04 |
| 2020/0017511 A1 | 1/2020 | Blank et al. | |
| 2020/0017517 A1 | 1/2020 | Gill et al. | |
| 2020/0108071 A1 | 4/2020 | Chin et al. | |
| 2020/0368238 A1 | 11/2020 | Nichols et al. | |
| 2020/0407372 A1 | 12/2020 | Koltun et al. | |
| 2021/0053989 A1 | 2/2021 | Zou | |
| 2021/0101870 A1 | 4/2021 | Koltun et al. | |
| 2021/0154190 A1 | 5/2021 | Wildes | |
| 2022/0031695 A1 | 2/2022 | Pitzen et al. | |
| 2022/0073521 A1 | 3/2022 | Zou et al. | |
| 2022/0127271 A1 | 4/2022 | Wan et al. | |

FOREIGN PATENT DOCUMENTS

| | | |
|---|---|---|
| CN | 103181918 A | 7/2013 |
| CN | 103554038 | 2/2014 |
| CN | 105916845 A | 8/2016 |

(Continued)

OTHER PUBLICATIONS

U.S. Appl. No. 62/646,107, filed Mar. 21, 2018 to Xie et al.*

(Continued)

*Primary Examiner* — Erich A Leeser

(74) *Attorney, Agent, or Firm* — Cooley LLP

(57) ABSTRACT

The present disclosure is directed to inhibitors of SHP2 and their use in the treatment of disease. Also disclosed are pharmaceutical compositions comprising the same.

6 Claims, No Drawings

(56) References Cited

FOREIGN PATENT DOCUMENTS

| | | |
|---|---|---|
| CN | 110156786 A | 8/2019 |
| EA | 201691442 A1 | 12/2016 |
| EP | 0 088 593 A2 | 9/1983 |
| EP | 0 579 835 A1 | 1/1994 |
| GB | 1459571 A | 12/1976 |
| JP | S5762269 A | 4/1982 |
| JP | H02-049775 A | 2/1990 |
| JP | H04-112877 A | 4/1992 |
| JP | H09510987 A | 11/1997 |
| JP | 2007277097 A | 10/2007 |
| JP | 2007530434 A | 11/2007 |
| JP | 2010520238 A | 6/2010 |
| JP | 2013502424 A | 1/2013 |
| JP | 2013522222 A | 6/2013 |
| JP | 2013526526 A | 6/2013 |
| JP | 2013531025 A | 8/2013 |
| JP | 2017502993 A | 1/2017 |
| JP | 2017502994 A | 1/2017 |
| JP | 2017503000 A | 1/2017 |
| JP | 2017522346 A | 9/2019 |
| WO | WO 93/09664 | 5/1993 |
| WO | WO 97/29109 A1 | 8/1997 |
| WO | WO 98/56376 | 12/1998 |
| WO | WO 01/16097 A1 | 3/2001 |
| WO | WO 2001060806 A2 | 8/2001 |
| WO | WO 03/029422 A2 | 4/2003 |
| WO | WO 2003045924 A1 | 6/2003 |
| WO | WO 03/082191 A2 | 10/2003 |
| WO | WO 2004/024719 A1 | 3/2004 |
| WO | WO 2004099201 A1 | 11/2004 |
| WO | WO 2004/111034 A1 | 12/2004 |
| WO | WO 2005028480 A2 | 3/2005 |
| WO | WO 2005035532 A1 | 4/2005 |
| WO | WO 2005/040151 A1 | 5/2005 |
| WO | WO 2005/000817 A2 | 6/2005 |
| WO | WO 2005/106286 A1 | 11/2005 |
| WO | WO 2006/002284 | 1/2006 |
| WO | WO 2006071759 A2 | 7/2006 |
| WO | WO 2006/113704 A1 | 10/2006 |
| WO | WO 2007/048067 A2 | 4/2007 |
| WO | WO 2007/106142 A2 | 9/2007 |
| WO | WO 2007/131991 A1 | 11/2007 |
| WO | WO 2007/145921 A1 | 12/2007 |
| WO | WO 2007/138072 A2 | 2/2008 |
| WO | WO 2007/138072 A3 | 2/2008 |
| WO | WO 2008/122615 A1 | 10/2008 |
| WO | WO 2008/138842 A1 | 11/2008 |
| WO | WO 2008/138843 A1 | 11/2008 |
| WO | WO 2009/020642 A1 | 2/2009 |
| WO | WO-2009025823 A1 | 2/2009 |
| WO | WO 2010/011666 A2 | 1/2010 |
| WO | WO 2011/022440 A2 | 2/2011 |
| WO | WO-2011112766 A2 | 9/2011 |
| WO | WO 2011154327 A1 | 12/2011 |
| WO | WO 2012/055942 A1 | 5/2012 |
| WO | WO 2012/116237 A2 | 8/2012 |
| WO | WO 2013/105063 A1 | 7/2013 |
| WO | WO 2014023385 A1 | 2/2014 |
| WO | WO 2014/072881 A1 | 5/2014 |
| WO | WO 2014/113584 | 7/2014 |
| WO | WO 2014/121885 A1 | 8/2014 |
| WO | WO 2015/107493 A1 | 7/2015 |
| WO | WO 2015/107494 A1 | 7/2015 |
| WO | WO 2015/107495 A1 | 7/2015 |
| WO | WO 2016/007731 A1 | 1/2016 |
| WO | WO-2016081290 A1 | 5/2016 |
| WO | WO 2016/100116 A1 | 6/2016 |
| WO | WO 2016/103155 A1 | 6/2016 |
| WO | WO 2016/112295 A1 | 7/2016 |
| WO | WO-2016125169 A1 | 8/2016 |
| WO | WO 2016/161282 A1 | 10/2016 |
| WO | WO 2016/203404 A1 | 12/2016 |
| WO | WO 2016/203405 A1 | 12/2016 |
| WO | WO 2016/203406 A1 | 12/2016 |
| WO | WO 2017/059207 A1 | 4/2017 |
| WO | WO 2017/156397 A1 | 9/2017 |
| WO | WO-2017162524 A1 | 9/2017 |
| WO | WO 2017/211303 A1 | 12/2017 |
| WO | WO 2017/216706 A1 | 12/2017 |
| WO | WO 2018/013597 A1 | 1/2018 |
| WO | WO 2018/057884 A1 | 3/2018 |
| WO | WO 2018/081091 A1 | 5/2018 |
| WO | WO 2018/130928 A1 | 7/2018 |
| WO | WO 2018/136264 A1 | 7/2018 |
| WO | WO 2018/136264 A1 | 7/2018 |
| WO | WO 2018/136265 A1 | 7/2018 |
| WO | WO 2018/172984 A1 | 9/2018 |
| WO | WO 2018/187401 A1 | 10/2018 |
| WO | WO 2018/187423 A1 | 10/2018 |
| WO | WO 2018/218133 A1 | 11/2018 |
| WO | WO 2019/051084 A1 | 3/2019 |
| WO | WO 2019/075265 A1 | 4/2019 |
| WO | WO 2019/118909 A1 | 6/2019 |
| WO | WO 2019/199792 A1 | 10/2019 |
| WO | WO 2019/212990 A1 | 11/2019 |
| WO | WO 2019/212991 A1 | 11/2019 |
| WO | WO 2020/055761 A1 | 3/2020 |
| WO | WO-2020061101 A1 * | 3/2020 ......... A61K 31/5383 |
| WO | WO 2020/106647 A2 | 5/2020 |
| WO | WO-2020094104 A1 | 5/2020 |
| WO | WO-2020/132597 A1 | 6/2020 |
| WO | WO-2020108590 A1 | 6/2020 |
| WO | WO 2021/091967 A | 5/2021 |

OTHER PUBLICATIONS

3-Amino-6-phenyl-4-trifluoromethylpyridine, C12H9F3N2, PubChem CID 129781129, retrieved from https://pubchem.ncbi.nlm.nih.gov/compound/129781129 on Oct. 20, 2021. (8 pages).

Anonymous: "RMC-4630," Jul. 20, 2018 (Jul. 20, 2018), pp. 1-1, Retrieved from the Internet: URL: https://integrity.clarivate.com/integrity/xmlxsl/pk_prod_list.exec_form_pro_pr.

Banker et al., Modern Pharmaceutics, Third Edition, Revised and Expanded by, Marcel Dekker, Inc. pp. 451 and 596, 1976. (3 pages).

Belanger, David B. et al., "Discovery of imidazo [1,2-a] pyrazine-based Aurora kinase inhibitors," Bioorganic & medicinal chemistry letters 20.17 (2010): 5170-5174.

Bhatia et al., A Review on Bioisosterism: A Rational Approach for Drug Design and Molecular Modification, Pharmacologyonline.

Database Registry, Compound with CAS Registry No. 1119718-06-7-1,4-Dioxa-8-azaspiro[4.5]decane, 8-[5-(6,7-dimethoxy-4-cinnolinyl)-3-methyl-2-pyridinyl], Mar. 12, 2009.

Database Registry, Compound with CAS Registry No. 1384576-77-5, 1,4-Dioxa-8-azaspiro[4.5]decane, 8-[6-(3-fluorophenyl)-4-methyl-3-pyridazinyl], Jul. 27, 2012.

Ellsworth et al., "Discovery of pyrazine carboxamide CBI antagonists: The introduction of a hydroxyl group improves the pharmaceutical properties and in vivo efficacy of the series," Bioorganic & Medicinal Chemistry Letters, vol. 17, No. 14, Jul. 1, 2007, pp. 3978-3982.

Fedele et al., "SHP2 Inhibition Prevents Adaptive Resistance to MEK inhibitors in Multiple Cancer Models," Cancer Discov. Oct. 2018; 8(10): 1237-1249.

Hydrates, products of the addition of water (hydration) to molecules, atoms, or ions. M. b. gaseous, liquid, and solid; the last called, crystal hydrates. XUMUK, Wayback internet archive machine, Oct. 27, 2007. (machine translated from Russian) [retrieved Sep. 3, 2021] Retrieved from the Internet: <URL: https://xumuk.ru/encyklopedia/1022.html>.

International Search Report dated Sep. 2, 2019, for International Application No. PCT/US2019/026543, 9 pages.

International Preliminary Report on Patentability dated Oct. 13, 2020, for International Application No. PCT/US2019/026543, 15 pages.

Jiang, et al., Optimal therapeutic positioning of a seective bi-steric inhibitor of MTORC1 in geneticaly defined cancers, European Journal of Cancer, Oct. 1, 2020, 2 pages, vol. 138.

(56) References Cited

OTHER PUBLICATIONS

Jordan, "Tamoxifen: A Most Unlikely Pioneering Medicine," Nature Reviews: Drug Discovery, vol. 2, Mar. 2003, 205-213.
Larochelle et al. "Structural reorganization of SHP2 by oncogenic mutations and implications for oncoprotein resistance to allosteric inhibition", Nature Communications, vol. 9, No. 1, Oct. 30, 2018, 10 pages.
Larochelle et al., "Structural and Functional Consequences of Three Cancer-Associated Mutations of the Oncogenic Phosphatase SHP2," Biochemistry, vol. 55, No. 15, Apr. 11, 2016, pp. 2269-2277.
Masuda H. et al., "Synthesis of Alkoxy-, (Alkylthio)-, Phenoxy-, and (Phenylthio)pyrazines and their Olfactive Properties," J. Agric. Food Chem., 1986, 34(2), pp. 377-381.
Monson et al., "The reactions of some ketones with hexamethylphosphoric triamide a novel synthesis of 3,5-dialkyl-2,6-diphenylpyridines," Tetrahedron 31:1145-1147, 1975.
Nichols et al., "Efficacy of SHP2 phosphatase inhibition in cancers with nucleotide-cycling oncogenic RAS, RAS-GTP dependent oncogenic BRAF and NF1 loss," bioRxiv preprint first posted online Sep. 14, 2017, 16 pages.
Patani et al., "Bioisosterism: A Rational Approach in Drug Design," Chemical Reviews, 1996, 96, 3147-3176.
Sayer, James Richard, "The Synthesis of Imidazo [1,2-a] pyrazines as Inhibitors of the VirB11 ATPase and their Incorporation into Bivalent Compounds," Diss. UCL (University College London), 2013, 396 pages.
Sun et al., "Selective inhibition of leukemia-associated SHP2E69K mutant by the allosteric SHP2 inhibitor SHP099," Leukemia, Nature Publishing Group. UK, London, vol. 32, No. 5, Jan. 30, 2018, 4 pages.
Vernier et al., "Thioether benzenesulfonamide inhibitors of carbonic anhydrases II and IV: structure-based drug design, synthesis, and biological evaluation," Bioorganic & Medicinal Chemistry, vol. 18, Issue 9, May 1, 2010, pp. 3307-3319.
Vippagunta et al., "Crystalline solids," Advanced Drug Delivery Reviews 48, Mar. 26, 2001.
Wolff, "Burger's Medicinal Chemistry and Drug Discovery," Fifth Edition, vol. 1: Principles and Practice, New York: John Wiley & Sons, 1994, 975-977.
Wustrow D.J. et al., "Aminopyrazine CB1 receptor inverse agonists," Bioorganic & Medicinal Chemistry Letters, vol. 18, No. 11, 2008, p. 3376-3381.
Xiao et al., "Myeloid-restricted ablation of Shp2 restrains melanoma growth by amplifying the reciprocal promotion of CXCL9 and IFN-γ production in tumor microenvironment," Oncogene, May 7, 2018, 13 pages.
Yamanishi Y. et al., "Syntheses of trimethylpyrazines and their antibacterial properties," Yakugaku Zasshi, 1967, 87(1), pp. 105-107.
Zhao et al., "SHP2 inhibition triggers anti-tumor immunity and synergizes with PD-1 blockade," Acta Pharmaceutica Sinica B 2019;9(2):304-315.
International Search Report and Written Opinion dated Dec. 20, 2017, for PCT/US2017/041577, 18 pages.
International Search Report and Written Opinion dated Sep. 21, 2018, for PCT/US2018/013018, 10 pages.
International Search Report and Written Opinion dated Apr. 5, 2018, for PCT/US2018/013023, 13 pages.
International Search Report and Written Opinion dated Jan. 24, 2019, for PCT/US2018/055502, 16 pages.
International Search Report and Written Opinion dated Dec. 12, 2018, for PCT/US2018/049744, 13 pages.
International Search Report and Written Opinion dated Feb. 20, 2019, for PCT/US2018/065817, 11 pages.
Chen et al., "Allosteric inhibition of SHP2 phosphatase inhibits cancers driven by receptor tyrosine kinases," Nature 2016, 535, 148-152.
Chen et al., "Identification of demethylincisterol A3 as a selective inhibitor of protein tyrosine phosphatase Shp2," Eur J Pharmacol. Jan. 15, 2017;795:124-133.
Fortanet et al., "Allosteric Inhibition of SHP2: Identification of a Potent, Selective, and Orally Efficacious Phosphatase Inhibitor," J. Med. Chem. 2016, 59, 7773-7782.
Larochelle et al., "Identification of an allosteric benzothiazolopyrimidone inhibitor of the oncogenic protein tyrosine phosphatase SHP2," Bioorg. Med. Chem. 2017, 17, 31394-31399.
Meurer et al., "Synthesis and SAR of 5,6-diarylpyridines as human CB1 inverse agonists," Bioorg Med Chem Lett. Feb. 1, 2005;15(3):645-51.
Mohi et al., "The role ofShp2 (PTPN11) in cancer," Curr Opin Genet Dev. Feb. 2007;17(1):23-30.
Nichols et al., "RAS nucleotide cycling underlies the SHP2 phosphatase dependence of mutant BRAF-, NF1- and RAS-driven cancers," Nat Cell Biol. Sep. 2018;20(9):1064-1073.
Ruess et al., "Mutant KRAS-driven cancers depend on PTPN11/SHP2 phosphatase," Nat Med. Jul. 2018;24(7):954-960.
Xie et al., "Allosteric Inhibitors of SHP2 with Therapeutic Potential for Cancer Treatment," J. Med. Chem. 2017, 60, 10205-10219.
Database Registry [Online] Chemical Abstracts Service, Columbus, Ohio, US; Apr. 27, 2011 (Apr. 27, 2011), XP002787392, retrieved from STN Database accession No. 1286273-60-6 compound with CAS registry No. 1286273-60-6.
Database Registry [Online] Chemical Abstracts Service, Columbus, Ohio, US; Nov. 9, 2007 (Nov. 9, 2007), XP002787393, retrieved from stn Database accession No. 952723-55-6 compound with CAS registry No. 952723-55-6.
Database Registry [Online] Chemical Abstracts Service, Columbus, Ohio, US; Jan. 22, 2015 (Jan. 22, 2015), XP002787394, retrieved from stn Database accession No. 1643677-14-8 compound with CAS registry No. 1643677-14-8.
Database Registry [Online] Chemical Abstracts Service, Columbus, Ohio, US; Nov. 16, 1984 (Nov. 16, 1984 ), XP002787395, retrieved from stn Database accession No. 86663-20-9 compound with CAS registry No. 86663-20-9.
Database Registry [Online] Chemical Abstracts Service, Columbus, Ohio, US; Dec. 18, 1984 (Dec. 18, 1984), XP002787396, retrieved from stn Database accession No. 93034-72-1 compound with CAS registry No. 93034-72-1.
Database Registry [Online] Chemical Abstracts Service, Columbus, Ohio, US; Nov. 16, 1984 (Nov. 16, 1984), XP002787397, retrieved from stn Database accession No. 68559-45-5 compound with CAS registry No. 68559-45-5.
Database Registry [Online] Chemical Abstracts Service, Columbus, Ohio, US; Nov. 23, 2004 (Nov. 23, 2004), XP002787398, retrieved from stn Database accession No. 786652-86-6 compound with CAS registry No. 786652-86-6.
Database Registry [Online] Chemical Abstracts Service, Columbus, Ohio, US; Nov. 23, 2004 (Nov. 23, 2004), XP002787399, retrieved from stn Database accession No. 786652-83-3 compound with CAS registry No. 786652-83-3.
Database Registry [Online] Chemical Abstracts Service, Columbus, Ohio, US; Apr. 6, 1990 (Apr. 6, 1990), XP002787400, Database accession No. 126317-60-0 compound with CAS registry No. 126317-60-0.
Database Registry [Online] Chemical Abstracts Service, Columbus, Ohio, US; May 31, 2006 (May 31, 2006), XP002787401, retrieved from stn Database accession No. 886208-65-7 compound with CAS registry No. 886208-65-7.
Database Registry [Online] Chemical Abstracts Service, Columbus, Ohio, US; Aug. 27, 2010 (Aug. 27, 2010), XP002787406, retrieved from stn Database accession No. 1239320-06-9 compound with CAS registry No. 1239320-06-9.
Database Registry, Compound with CAS Registry No. 78246-19-2. 3-Methyl-5-(2-methylpropyl)-2-(phenylthio)pyrazine. Nov. 16, 1984 Citation is not enclosed due to copyright restrictions.
Database Registry, Compound with CAS Registry No. 15033-82-6. 4-[(3,5,6-Trimethyl-2-pyrazinyl)sulfonyl]benzenamine. Nov. 16, 1984 Citation is not enclosed due to copyright restrictions.
Belton, et al., A Novel N → S Oxygen Migration in 2,1,3-Benzoxadiazole Systems, Proceedings of the Royal Irish Academy. Section B: Biological, Geological, and Chemical Science, Royal Irish Academy, 1974, pp. 185-192, vol. 74.

(56) References Cited

OTHER PUBLICATIONS

Boamah, et al., Pyridazines. XXXVII†‡. Novel triazanaphthalene derivatives via intramolecular cyclization reactions of vic-disubstituted pyridazines, Journal of Heterocyclic Chemistry, 1988, pp. 879-883, vol. 25, No. 3.
CAS Registry No. 1349160-17-3; STN Entry Date Dec. 5, 2011; 5-(2-Chloro-4-methoxyphenyl)-3,6-diethyl-N-(1-ethylbutyl)-2-pyrazinamine.
CAS Registry No. 1349131-06-1; STN Entry Date Dec. 5, 2011; 3,6-Diethyl-N-(1-ethylpropyl)-5-[6-(1-methylethyl)-2-[(2-methylpropyl)amino]-3-pyridinyl]-2-pyrazinamine.
CAS Registry No. 1350134-68-7; STN Entry Date Dec. 7, 2011; N-[(3S,4S)-4-Butoxytetrahydro-3-furanyl]-5-(2-chloro-4-methoxyphenyl)-3,6-diethyl-2-pyrazinamine.
CAS Registry No. 1027540-93-7; STN Entry Date Jun. 12, 2008; 5-(2,4-Dichlorophenyl)-N-(4-ethoxy-1-methyl-3-pyrrolidinyl)-3,6-diethyl-2-pyrazinamine.
CAS Registry No. 1026750-06-0; STN Entry Date Jun. 9, 2008; 5-[2-(Cyclohexyloxy)-6-methyl-4-pyrimidinyl]-2,3-dihydro-2-[3-methyl-5-(4-methyl-1-piperazinyl)-2-pyrazinyl]-2-thiazolamine.
CAS Registry No. 777880-58-7 Entry date Nov. 10, 2004, 2,1,3-Benzoxadiazole, 4-(1-piperidinyl)-7-(1-piperidinylsulfonyl)—(CA Index Name).
CAS Registry No. 777873-58-2, Entry date Nov. 10, 2004, 2,1,3-Benzoxadiazole, 4-(4-methyl-1-piperidinyl)-7-[(4-methyl-1-piperidinyl)sulfonyl]—(CA Index Name).
CAS Registry No. 777873-55-9, Entry date Nov. 10, 2004, 2,1,3-Benzoxadiazole, 4-(3-methyl-1-piperidinyl)-7-[(3-methyl-1-piperidinyl)sulfonyl]—(CA Index Name).
CAS Registry No. 1918848-03-9, Entry date May 26, 2016, 4-Piperidinamine, 1-[2-(1-methylethyl)pyrazolo[1,5-a]pyrazin-4-yl]—(CA Index Name).
CAS Registry No. 1918847-95-6, Entry date May 26, 2016, 4-Piperidinamine, 1-[2-(1,1-dimethylethyl)pyrazolo[1,5-a]pyrazin-4-yl]—(CA Index Name).
Dardaei, et al., SHP2 inhibition restores sensitivity in ALK-rearranged non-small-cell lung cancer resistant to ALK inhibitors, Nature Medicine, Mar. 5, 2018, pp. 512-517, vol. 24, No. 4.
Dardaei, et al., Supplemental Material, SHP2 inhibition restores sensitivity in ALK-rearranged non-small-cell lung cancer resistant to ALK inhibitors, Nature Medicine, Mar. 5, 2018, pp. 1-58, vol. 24.
Database Registry, RN 1629858-36-1, entered STN Oct. 23, 2014.
Database Registry, RN 1028262-30-7, entered STN Jun. 15, 2008.
Database Registry, RN 1027952-21-1, entered STN Jun. 13, 2008.
Database Registry, RN 1026418-24-5, entered STN Jun. 8, 2008.
Database Registry, RN 1026270-53-0, entered STN Jun. 8, 2008.
Database Registry, RN 1026250-49-6, entered STN Jun. 8, 2008.
Database Registry, RN 1334203-33-6, entered STN Sep. 30, 2011.
Database Registry, RN 1334203-32-5, entered STN Sep. 30, 2011.
Database Registry, RN 900624-41-1, entered STN Aug. 11, 2006.
Database Registry, RN 893813-11-1, entered STN Jul. 17, 2006.
Database Registry, RN 893813-68-2, entered STN Jul. 17, 2006.
Database Registry, RN 590404-14-1, entered STN Sep. 22, 2003.
Database Registry, RN 1860803-32-2, entered STN Feb. 5, 2016.
European Patent Office, European Office Action for European Application No. 18701883.3, dated Sep. 15, 2021, 6 pages.
European Patent Office, European Office Action for European Application No. 18701883.3, dated Mar. 25, 2022, 4 pages.
Davare, et al., Foretinib is a potent inhibitor of oncogenic ROS1 fusion proteins, PNAS, Nov. 11, 2013, pp. 19519-19524, vol. 110, No. 48.
Giori et al., "Synthesis of 6,7-Disubstituted Pteridine-2,4-Diones," Heterocycles, vol. 32, No. 1, 1991, 6 pages.
Huang, et al., Discovery of First-in-Class, Potent, and Orally Bioavailable Embryonic Ectoderm Development (EED) Inhibitor with Robust Anticancer Efficacy, J. Med. Chem., Jan. 16, 2017, pp. 2215-2226, vol. 60, No. 6.
Leroy et al., Di-tert-butyl (methyl) phosphonium tetrafluoroborate, e-EROS Encyclopedia of Reagents for Organic Synthesis, Dec. 31, 2015, pp. 1-7.
Neel, et al., Differential Subcellular Localization Regulates Oncogenic Signaling by ROS1 Kinase Fusion Proteins, Cancer Res, Dec. 11, 2018, pp. 546-556, vol. 79, No. 3.
Ozawa et al., The importance of CH/phydrogen bonds in rational drug design: An abinitio fragment molecular orbital study to leukocyte-specific protein tyrosine (LCK) kinase, Dec. 31, 2008, Bioorganic & Medicinal Chemistry, pp. 10311-10318, vol. 16.
Rauen, et al., The RASopathies, Annu Rev Genomics Hum Genet. 2013, pp. 355-369, vol. 14.
Voena, et al., The Tyrosine Phosphatase Shp2 Interacts with NPM-ALK and Regulates Anaplastic Lymphoma Cell Growth and Migration, Cancer Res, Apr. 24, 2007, pp. 4278-4286, vol. 67, No. 9.
Wang et al., Palladium-Catalyzed Direct Heck Arylation of Dual TT-Deficient/TT-Excessive Heteroaromatics. Synthesis of C-5 Arylated lmidazo[1,5-a]pyrazin, Organic Letters, Jun. 25, 2008, pp. 2215-2226, vol. 10, No. 14.
Yap, et al, The NF1 gene revisited—from bench to bedside, Oncotarget, Aug. 2014, pp. 5873-5892, vol. 5, No. 15.
Zou, et al., PF-06463922 is a potent and selective next-generation ROS1/ALK inhibitor capable of blocking crizotinib-resistant ROS1 mutations, PNAS, Mar. 2, 2015, pp. 3493-3498, vol. 112, No. 11.
Mainardi, et al., SHP2 is required for growth of KRAS-mutant non-small-cell lung cancer in vivo, Nature Medicine, 2018, pp. 961-967, vol. 24.
Adam et al., "Concise synthesis of 1H-pyrazin-2-ones and 2-aminopyrazines" Synlett (11): 2004 2031-2033 compounds 6a, 6c and 6d.
Akhapkina. V.I et al., "Fundamentals of modulatory concept and classification of modulatory drugs," RMZh, N19, 2012, pp. 933-951.
Amato, C. et al., "Modulation of a proteolytic enzyme activity by means of photochromic inhibitor", Journal of Photochemistry and Photobiology B: Biology, 1995, vol. 28(1), p. 71-75.
Belikov, V.G ,"Pharmaceutical Chemistry. Chapter 2.6 Relationship between the chemical structure, properties of substances and their effect on the body-M," MEDpress-inform, 2007, pp. 27-29, and English translation, 14 pages.
CAS Registry No. 1119717-53-1, Entry date Mar. 12, 2009.
CAS Registry No. 174531-55-6, Entry date Mar. 26, 1996.
CAS Registry No. 3657-73-6, Entry date Nov. 16, 1984.
Database Registry, RN 1957154-25-4, 1956595-47-3, entered STN Jul. 21, 2016.
Database Registry, RN 1949800-28-5, entered STN Jul. 11, 2016.
Database Registry, RN 1952095-25-8, entered STN Jul. 14, 2016.
Database Registry, RN 1953046-94-0, 1952680-38, entered STN Jul. 15, 2016.
Database Registry, (STN)[online] online], [date of search Nov. 10, 2021], May 26, 2016, CAS Registry No. 1918768-32-7.
Dayakar et al., "Synthesis and antimycobacterial activity of 1 H-1,2,3-triazolylisonicotinohydrazi," Indian Journal of Chemistry, Section B: Organic Chemistry Including Medicinal Chemistry 55B (7), (2016), 882-887 intermediates 9c to 9f.
Fialkov Y., "Solvent as a means of controlling a chemical process", Publishing house "Chemistry", 1990, p. 240.
Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/rn_mater/docs/osnovi_med_pomoshi.pdf?ysclid=I5wi7xgplo450927514.
Krosig, U. et al., "Expanding the Genetic Alphabet: Pyrazine Nucleosides That Support a Donor-Donor-Acceptor Hydrogen-Bonding Pattern," Helv. Chim. Acta 2004, v.87, pp. 1299-1324.
Li, Hong Lian et al., "Exploring the effect of D61G mutation on SHP2 cause gain of function activity by a molecular dynamics study," J. Biomol. Struct. Dyn., Nov. 24, 2017, vol. 36, No. 14, pp. 3856-3868.
Mehta, V. et al., "Microwave-Assisted Palladium-Catalyzed Phosphonium Coupling of 2(1H)-Pyrazinones," J. Org. Chem. 2010, 75, 3, 976-979.
Perez et al., "Palladium-Catalyzed C,N-Cross Coupling Reactions of 3-Halo-2-aminopyridines," Organic Letters 13 (8): 2011; 1984-1987 compound 5 of Figure 2; compounds 12 and 13 of Scheme 2.

(56) References Cited

OTHER PUBLICATIONS

Pisaneschi, F. et al., "The 3S Enantiomer Drives Enolase Inhibitory Activity in SF2312 and its Analogues", Molecules, 2019, vol. 24(13), 2510, p. 1-18.
Ran et al., "Sticking it to Cancer with Molecular Glue for SHP2" Cancer Cell. Aug. 8, 2016;30(2):194-196.
Sansfacon et al., "SHP-2 phosphatase contributes to KRAS-driven intestinal oncogenesis but prevents colitis-associated cancer development," Oncotarget. Oct. 4, 2016;7(40):65676-65695.
Tol, J. et al., "Chemotherapy, bevacizumab, and cetuximab in metastatic colorectal cancer," N Engl J Med, Feb. 5, 2009, vol. 360(6), pp. 563-572.
Yu, H. A. et al., "A phase 1/2 trial of ruxolitinib and erlotinib in patients with EGFR-mutant lung adenocarcinomas with acquired resistance to erlotinib," Journal of Thoracic Oncology, 2017, vol. 12(1), pp. 102-109.
Zefirova, On et al., "On the Origin and Development if the Concept of Bioisoterism," Vestn Mosk Un-Ta Ser 2 Chemistry, 2002, vol. 43(4), pp. 251-256.
Database Registry, RN 893806-50-3, entered STN Jul. 17, 2006.
Database Registry, RN 893807-90-4, entered STN Jul. 17, 2006.
Database Registry, RN 893808-63-4, entered STN Jul. 17, 2006.
Database Registry, RN 893810-11-2, entered STN Jul. 17, 2006.
9-(4-chlorophenyl)-5-(4-morpholinyl)tetrazolo[1,5-c]-thieno[3,2-e]pyrimidine, entered STN Jul. 17, 2006.
9-(4-chlorophenyl)-5-(4-morpholinyl)thieno[3,2-e]-1,2,4-triazolo[4,3-c]pyrimidineentered STN Jul. 17, 2006, 1 page.
9-phenyl-5-(1-pyrrolidinyl)tetrazolo[1,5-c]thieno[3,2-e]pyrimidine, entered STN Jul. 17, 2006, 1 page.
9-phenyl-5-(1-pyrrolidinyl)thieno[3,2-e]-1,2,4-triazolo[4,3-c]pyrimidine, entered STN Jul. 17, 2006, 1 page.
Database Registry, RN 893294-18-3, entered STN Jul. 17, 2006, 1 page.
Database Registry, RN 893792-24-0, entered STN Jul. 17, 2006, 1 page.
Database Registry, RN 893792-68-2, entered STN Jul. 17, 2006, 1 page.
Database Registry, RN 893794-10-0, entered STN Jul. 17, 2006, 1 page.
Database Registry, RN 893795-14-7, entered STN Jul. 17, 2006, 1 page.
Database Registry, RN 893796-38-8, entered STN Jul. 17, 2006, 1 page.
Database Registry, RN 893796-42-4, entered STN Jul. 17, 2006, 1 page.
Database Registry, RN 893797-57-4, entered STN Jul. 17, 2006, 1 page.
Database Registry, RN 893797-61-0, entered STN Jul. 17, 2006, 1 page.
Database Registry, RN 893799-39-8, entered STN Jul. 17, 2006, 1 page.
Database Registry, RN 893799-43-4, entered STN Jul. 17, 2006, 1 page.
Database Registry, RN 893799-47-8, entered STN Jul. 17, 2006, 1 page.
Database Registry, RN 893801-34-8, entered STN Jul. 17, 2006, 1 page.
Database Registry, RN 893803-59-3, entered STN Jul. 17, 2006, 1 page.

* cited by examiner

PYRIDINE, PYRAZINE, AND TRIAZINE COMPOUNDS AS ALLOSTERIC SHP2 INHIBITORS

CROSS REFERENCE TO RELATED APPLICATIONS

This application is a continuation of International Patent Application No. PCT/US2018/055502, filed Oct. 11, 2018, which claims the benefit of U.S. Provisional Application No. 62/571,760, filed Oct. 12, 2017; U.S. Provisional Application No. 62/615,353, filed Jan. 9, 2018; and U.S. Provisional Application No. 62/678,889, filed May 31, 2018; the contents of each of which are incorporated herein by reference in their entireties.

FIELD OF THE DISCLOSURE

The present disclosure relates to inhibitors of protein tyrosine phosphatase SHP2 useful in the treatment of diseases or disorders. Specifically, this disclosure is concerned with compounds and compositions inhibiting SHP2, methods of treating diseases associated with SHP2, and methods of synthesizing these compounds.

BACKGROUND OF THE DISCLOSURE

SH2 domain-containing protein tyrosine phosphatase-2 (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, auto-inhibited conformation stabilized by a binding network involving residues from both the N—SH2 and PTP domains. Stimulation by, for example, cytokines or growth factors leads to exposure of the catalytic site resulting in enzymatic activation of SHP2.

Mutations in the the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present disclosure fulfill the need for small molecules to that inhibit the activity of SHP2.

SUMMARY OF THE DISCLOSURE

The present disclosure relates to compounds capable of inhibiting the activity of SHP2. The disclosure further provides a process for the preparation of compounds disclosed herein, pharmaceutical preparations comprising such compounds and methods of using such compounds and compositions in the management of diseases or disorders associated with the aberrant activity of SHP2.

One aspect of the disclosure relates to compounds of Formula Ia:

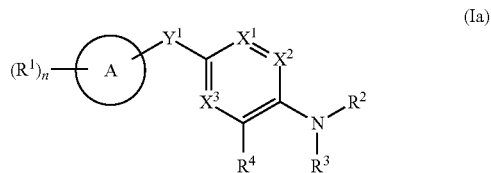

(Ia)

and pharmaceutically acceptable salts, prodrugs, solvates, hydrates, tautomers, and isomers thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;
$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;
$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or
$R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;
$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —$NHS(O)_2R^5$, —$NHS(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —NH$_2$, or halogen;

$R^5$ and $R^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

$R^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

One aspect of the disclosure relates to compounds of Formula I:

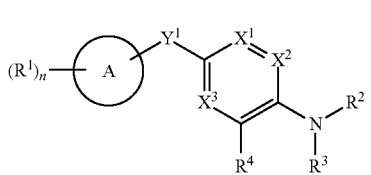

(I)

and pharmaceutically acceptable salts, prodrugs, solvates, hydrates, tautomers, and isomers thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond, A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, or —NR$^5$C(O)R$^6$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ and $R^3$ are independently selected from the group consisting of —H, -D, —OH, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

$R^4$ is —H, -D, —C$_1$-C$_6$alkyl, —C$_1$-C$_6$haloalkyl, —C$_1$-C$_6$hydroxyalkyl —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

$R^5$ and $R^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

$R^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

One aspect of the disclosure relates to compounds of Formula IIa:

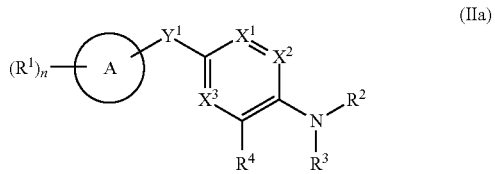

(IIa)

and pharmaceutically acceptable salts, prodrugs, solvates, hydrates, tautomers, and isomers thereof, wherein:

$X^1$ is N or CH;
$X^2$ is N or CH;
$X^3$ is N or CH;
wherein at least one of $X^1$, $X^2$, or $X^3$ is N;
$Y^1$ is a direct bond;
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O) $R^5$, —NHC(O)$NHR^5$, —$NHS(O)_2R^5$, —$NHS(O)_2NHR^5$, —$S(O)_2OH$, —$C(O)OR^5$, —$NH(CH_2)_nOH$, —C(O)NH $(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —R, —$OR^5$, —$NR^5R^6$, —$SR^5$, —$S(O)_2NR^5R^6$, —$S(O)_2R^5$, —$NR^5S(O)_2$ $NR^5R^6$, —$NR^5S(O)_2R^6$, —$S(O)NR^5R^6$, —$S(O)R^5$, —$NR^5S$ $(O)NR^5R^6$, —$NR^5S(O)R^6$, —$C(O)NR^5R^6$—, —$NR^5R^6C$ (O)—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

One aspect of the disclosure relates to compounds of Formula IIb:

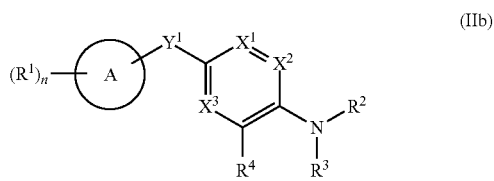

(IIb)

and pharmaceutically acceptable salts, prodrugs, solvates, hydrates, tautomers, and isomers thereof, wherein:

$X^1$ is N or CH;
$X^2$ is N or CH;
$X^3$ is N or CH;
wherein at least one of $X^1$, $X^2$, or $X^3$ is N;
$Y^1$ is —S—;
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2$ $R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2$ $NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)$ $R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —COOR$^b$, —CONHR$^b$, —CONH(CH$_2$)$_n$COOR$^b$, —NHCOOR$^b$, —CF$_3$, —CHF$_2$, —CH$_2$F, or =O;

R$^4$ is —H, -D, —C$_1$-C$_6$alkyl, —C$_1$-C$_6$haloalkyl, —C$_1$-C$_6$hydroxyalkyl —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

R$^5$ and R$^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

One aspect of the disclosure relates to compounds of Formula III:

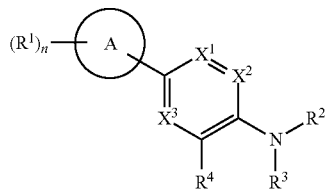

(III)

and pharmaceutically acceptable salts, prodrugs, solvates, hydrates, tautomers, and isomers thereof, wherein:

X$^1$ is N or CH;
X$^2$ is N or CH;
X$^3$ is N or CH;
wherein at least one of X$^1$, X$^2$, or X$^3$ is N;
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, or —NR$^5$C(O)R$^6$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ and R$^3$ are independently selected from the group consisting of —H, -D, —OH, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^2$ to form a 3- to 12-membered monocyclic or polycyclic heterocycle, or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

R$^4$ is —H, -D, or —C$_1$-C$_6$alkyl, wherein each alkyl is optionally substituted with one or more —OH, —NH$_2$, halogen, or oxo;

R$^5$ and R$^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

One aspect of the disclosure relates to compounds of Formula IV:

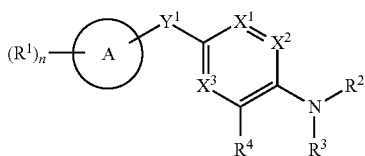

and pharmaceutically acceptable salts, prodrugs, solvates, hydrates, tautomers, and isomers thereof, wherein:
$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;
$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;
$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or
$R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;
$R^4$ is —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —C(O)$OR^5$, —$NH(CH_2)_nOH$, —C(O)NH$(CH_2)_nOH$, —C(O)NH$(CH_2)_nR^b$, —C(O)$R^b$, —$NH_2$, —OH, —CN, —C(O)$NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;
$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;
$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;
$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)$NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and
n is independently 0, 1, 2, 3, 4, 5, 6, 7, 8, 9, or 10.
One aspect of the disclosure relates to compounds of Formula V:

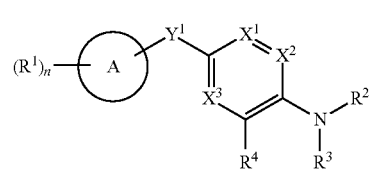

and pharmaceutically acceptable salts, prodrugs, solvates, hydrates, tautomers, and isomers thereof, wherein:
$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;
$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² and R³ are independently selected from the group consisting of —H, -D, —OH, —C₁-C₆alkyl, a 3- to 12-membered monocyclic or polycyclic heterocycle, a 5- to 12-membered spiroheterocycle, C₃-C₈cycloalkyl, —(CH₂)ₙ—Rᵇ, or —(CH₂)ₙC(O)NR⁵R⁶, wherein each alkyl, heterocycle, or cycloalkyl is optionally substituted with one or more —C₁-C₆alkyl, —OH, —NH₂, —ORᵇ, —NHRᵇ, —(CH₂)ₙOH, heterocyclyl, or spiroheterocyclyl; or R³ can combine with R² to form a 3- to 12-membered monocyclic or polycyclic heterocycle, or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, optionally substituted heteroaryl, optionally substituted heterocyclyl, —(CH₂)ₙNH₂, —(CH₂)ₙOH, —COORᵇ, —CONHRᵇ, —CONH(CH₂)ₙCOORᵇ, —NHCOORᵇ, —O—C(O)—NR⁵R⁶, —CF₃, —CHF₂, —CH₂F, or =O; wherein the heteroaryl and heterocyclyl are optionally substituted with —CN;

R⁴ is-C₁-C₆alkyl, wherein each alkyl is optionally substituted with one or more —OH, —NH₂, halogen, or oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

Rᵇ is independently —H, -D, —C₁-C₆alkyl, —C₁-C₆cycloalkyl, —C₂-C₆alkenyl, —(CH₂)ₙ-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH₂)ₙ OH, —C₁-C₆alkyl, CF₃, CHF₂, or CH₂F; and n is independently 0, 1, 2, 3, 4, 5, 6, 7, 8, 9, or 10.

One aspect of the disclosure relates to compounds of Formula VI:

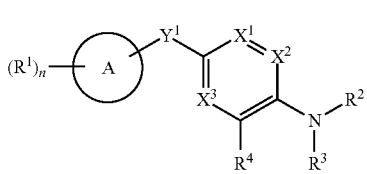

(VI)

and pharmaceutically acceptable salts, prodrugs, solvates, hydrates, tautomers, and isomers thereof, wherein:

X¹ is N or CH;
X² is N or CH;
X³ is N or CH;

wherein at least one of X¹, X², or X³ is N;

Y¹ is —S— or a direct bond,

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, —NR⁵C(O)R⁶, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ can combine with R² to form a 3- to 12-membered monocyclic or polycyclic heterocycle, or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, optionally substituted heteroaryl, optionally substituted heterocyclyl, —(CH₂)ₙNH₂, —(CH₂)ₙOH, —COORᵇ, —CONHRᵇ, —CONH(CH₂)ₙCOORᵇ, —NHCOORᵇ, —O—C(O)—NR⁵R⁶, —CF₃, —CHF₂, —CH₂F, or =O; wherein the heteroaryl and heterocyclyl are optionally substituted with —CN;

R⁴ is-C₁-C₆alkyl, wherein each alkyl is optionally substituted with one or more —OH, —NH₂, halogen, or oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

Rᵇ is independently —H, -D, —C₁-C₆alkyl, —C₁-C₆cycloalkyl, —C₂-C₆alkenyl, —(CH₂)ₙ-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH₂)ₙ OH, —C₁-C₆alkyl, CF₃, CHF₂, or CH₂F; and n is independently 0, 1, 2, 3, 4, 5, 6, 7, 8, 9, or 10.

Another aspect of the disclosure relates to methods of treating a disease associated with SHP2 modulation in a subject in need thereof, comprising administering to the subject an effective amount of one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof).

Another aspect of the disclosure relates to methods of inhibiting SHP2. The method comprises administering to a patient in need thereof, an effective amount of one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof).

Another aspect of the disclosure is directed to pharmaceutical compositions comprising one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), and a pharmaceutically acceptable carrier. The pharmaceutically acceptable carrier can further comprise an excipient, diluent, or surfactant. The pharmaceutical composition can be effective for treating a disease associated with SHP2 modulation in a subject in need thereof.

Another aspect of the disclosure relates to methods of treating a disease associated with SHP2 modulation in a subject in need thereof, comprising administering to the subject an effective amount of a pharmaceutical composition comprising one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof).

Another aspect of the disclosure relates to methods of inhibiting SHP2 comprising administering to a patient in need thereof, an effective amount of a pharmaceutical composition comprising one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof).

Another aspect of the disclosure relates to one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), for use in treating or preventing a disease associated with SHP2 modulation. One aspect of the disclosure relates to pharmaceutical compositions comprising one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), and a pharmaceutically acceptable carrier, for use in treating of preventing a disease associated with SHP2 modulation.

Another aspect of the disclosure relates to the use of one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), in the manufacture of a medicament for treating or preventing a disease associated with SHP2 modulation. Another aspect of the disclosure relates to the use of pharmaceutical compositions comprising one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), and a pharmaceutically acceptable carrier, in the manufacture of a medicament for treating or preventing a disease associated with SHP2 modulation.

Another aspect of the disclosure relates to one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), for use as a medicament. Another aspect of the disclosure relates to pharmaceutical compositions comprising one or more compounds disclosed herein (e.g., compounds of Formula Ia, I, IIa, IIb, III, IV, V, or VI, and pharmaceutically acceptable salts, prodrugs, solvates, hydrates, tautomers, or isomers thereof), for use as a medicament. In some embodiments, the medicament is used for treating or preventing a disease associated with SHP2 modulation.

The present disclosure also provides compounds and pharmaceutical compositions that are useful in inhibiting SHP2.

DETAILED DESCRIPTION OF THE DISCLOSURE

In a first aspect, compounds of Formula Ia are described:

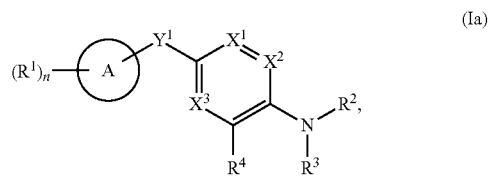

(Ia)

and pharmaceutically acceptable salts, prodrugs, solvates, hydrates, tautomers, and isomers thereof, wherein A, $Y^1$, $R^1$, $R^2$, $R^3$, $R^4$, $X^1$, $X^2$, $X^3$, and n are described as above.

In a another aspect, compounds of Formula I are described:

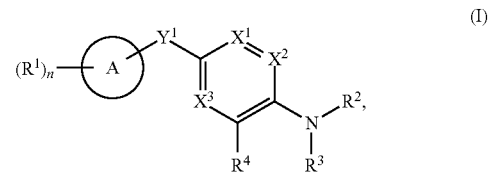

(I)

and pharmaceutically acceptable salts, prodrugs, solvates, hydrates, tautomers, and isomers thereof, wherein A, $Y^1$, $R^1$, $R^2$, $R^3$, $R^4$, $X^1$, $X^2$, $X^3$, and n are described as above.

In another aspect, compounds of Formula IIa are described:

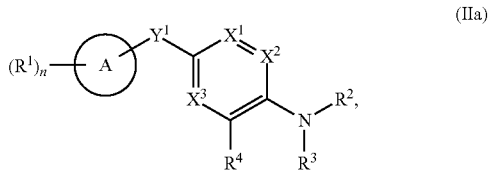

(IIa)

and pharmaceutically acceptable salts, prodrugs, solvates, hydrates, tautomers, and isomers thereof, wherein A, $Y^1$, $R^1$, $R^2$, $R^3$, $R^4$, $X^1$, $X^2$, $X^3$, and n are described as above.

In another aspect, compounds of Formula IIb are described:

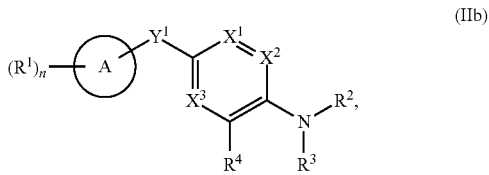

(IIb)

and pharmaceutically acceptable salts, prodrugs, solvates, hydrates, tautomers, and isomers thereof, wherein A, $Y^1$, $R^1$, $R^2$, $R^3$, $R^4$, $X^1$, $X^2$, $X^3$, and n are described as above.

In another aspect, compounds of Formula III are described:

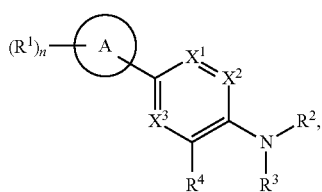

(III)

and pharmaceutically acceptable salts, prodrugs, solvates, hydrates, tautomers, and isomers thereof, wherein A, $R^1$, $R^2$, $R^3$, $R^4$, $X^1$, $X^2$, $X^3$, and n are described as above.

In another aspect, compounds of Formula IV are described:

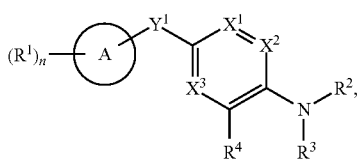

(IV)

and pharmaceutically acceptable salts, prodrugs, solvates, hydrates, tautomers, and isomers thereof, wherein A, $R^1$, $R^2$, $R^3$, $R^4$, $X^1$, $X^2$, $X^3$, and n are described as above.

In another aspect, compounds of Formula V are described:

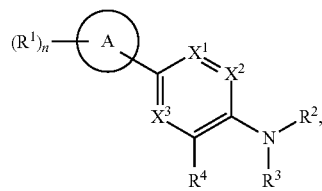

(V)

and pharmaceutically acceptable salts, prodrugs, solvates, hydrates, tautomers, and isomers thereof, wherein A, $R^1$, $R^2$, $R^3$, $R^4$, $X^1$, $X^2$, $X^3$, and n are described as above.

In another aspect, compounds of Formula VI are described:

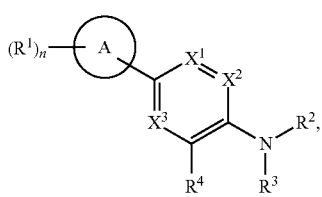

(VI)

and pharmaceutically acceptable salts, prodrugs, solvates, hydrates, tautomers, and isomers thereof, wherein A, $R^1$, $R^2$, $R^3$, $R^4$, $X^1$, $X^2$, $X^3$, and n are described as above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

Terms

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

The term "alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon carbon double bond and which may be straight or branched having about 2 to about 6 carbon atoms in the chain. Certain alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon carbon triple bond and which may be straight or branched having about 2 to about 6 carbon atoms in the chain. Certain alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" refers to a single saturated or partially unsaturated all carbon ring having 3 to 20 annular carbon atoms (i.e., $C_3$-$C_{20}$ cycloalkyl), for example from 3 to 12 annular atoms, for example from 3 to 10 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocycles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The term "aryl" as used herein refers to a single all carbon aromatic ring or a multiple condensed all carbon ring system wherein at least one of the rings is aromatic. For example, in certain embodiments, an aryl group has 6 to 20 annular carbon atoms, 6 to 14 annular carbon atoms, or 6 to 12 annular carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, Spiro and bridged bonds when allowed by valency requirements. It is also to be understood that when reference is made to a certain atom-range membered aryl (e.g., 6-12 membered aryl), the atom range is for the total ring (annular) atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like The aryl group may be optionally substituted by one or more substituents, e.g., 1 to 5 substituents, at any point of attachment. Exemplary substituents include, but are not limited to, —H, halogen, —O—$C_1$-$C_6$alkyl, —$C_1$-$C_6$alkyl, —O$C_2$-$C_6$alkenyl, —O$C_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 annular carbon atoms and about 1-4 annular heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycloalkyls, (to form for example a 1,2,3,4-tetrahydronaphthyridinyl such as 1,2,3,4-tetrahydro-1,8-naphthyridinyl), cycloalkyls (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 annular carbon atoms and about 1-6 annular heteroatoms. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, Spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The terms "heterocycloalkyl", "heterocycle", or "heterocyclyl" as used herein refers to a single saturated or partially unsaturated non-aromatic ring or a non-aromatic multiple ring system that has at least one heteroatom in the ring (at least one annular heteroatom selected from oxygen, nitrogen, and sulfur). Unless otherwise specified, a heterocycloalkyl group has from 3 to about 20 annular atoms, for example from 5 to 20 annular atoms, for example from 5 to 14 annular atoms, for example from 5 to 10 annular atoms, for example from 3 to 12 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The term also includes single saturated or partially unsaturated rings (e.g., 5, 6, 7, 8, 9, or 10-membered rings) having from about 4 to 9 annular carbon atoms and from about 1 to 3 annular heteroatoms selected from the group consisting of oxygen, nitrogen and sulfur in the ring. The rings of the multiple condensed ring system can be connected to each other via fused, spiro and bridged bonds when allowed by valency requirements. "Heterocyclyl" also includes radicals where heterocycle radicals are fused with a saturated, partially unsaturated ring, or aromatic carbocyclic or heterocyclic ring. Heterocycloalkyl groups include, but are not limited to, azetidine, aziridine, imidazolidine, imino-oxoimidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, quinuclidine, N-bromopyrrolidine, N-chloropiperidine, and the like.

The terms "spirocycle" or "spirocyclic" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$spirocycle is a spirocycle containing between 5 and 12 carbon atoms. In some embodiments, a $C_5$-$C_{12}$ spirocycle is a spirocycle containing from 5 to 12 carbon atoms. One or more of the carbon atoms can be substituted with a heteroatom.

The term "spirocyclic heterocycle," "spiroheterocyclyl," or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P. In some embodiments, a spirocyclic heterocycle can contain from 5 to 12 atoms, at least one of which is a heteroatom selected from N, O, S and P.

The term "halo" or "halogen" means a fluoro, chloro, bromo, or iodo group.

The term "carbonyl" refers to a functional group comprising a carbon atom double-bonded to an oxygen atom. It can be abbreviated herein as "oxo," as C(O), or as C=O.

The disclosure also includes pharmaceutical compositions comprising an effective amount of one or more disclosed compounds and a pharmaceutically acceptable carrier. As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals.

The disclosure includes pharmaceutically acceptable salts of the compounds described herein. Representative "pharmaceutically acceptable salts" include, but are not limited to, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" also includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the disclosure.

The disclosure includes prodrugs of the compounds described herein. The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The disclosure includes solvates of the compounds described herein. The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The disclosure includes isomers of the compounds described herein. The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of the present disclosure may have one or more asymmetric carbon atom and may occur as racemates, racemic mixtures and as individual enantiomers or diastereomers.

The term "stereoisomers" refers to the set of compounds which have the same number and type of atoms and share the same bond connectivity between those atoms, but differ in three dimensional structure. The term "stereoisomer" refers to any member of this set of compounds. For instance, a stereoisomer may be an enantiomer or a diastereomer. The disclosure includes stereoisomers of the compounds described herein.

In addition, the present disclosure embraces all geometric and positional isomers. For example, if a compound of the present disclosure incorporates a double bond or a fused ring, both the cis- and trans-forms, as well as mixtures, are embraced within the scope of the disclosure. If the compound contains a double bond, the substituent may be in the E or Z configuration. If the compound contains a disubstituted cycloalkyl, the cycloalkyl substituent may have a cis or trans configuration.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers. The disclosure includes enantiomers of the compounds described herein. Each compound herein disclosed includes all the enantiomers that conform to the general structure of the compound. The compounds may be in a racemic or enantiomerically pure form, or any other form in terms of stereochemistry. In some embodiments the compounds are the (S)-enantiomer. In other embodiments the compounds are the (R)-enantiomer. In yet other embodiments, the compounds are the (+) or (−) enantiomers In some embodiments, compounds and compositions of the disclosure may be enriched to provide predominantly one enantiomer of a compound described herein. An enantiomerically enriched mixture may comprise, for example, at least 60 mol percent of one enantiomer, or more preferably at least 75, 80, 85, 90, 95, 96, 97, 98, 99, 99.5 or even 100 mol percent. In some embodiments, the compound described herein enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2 mol percent of the second enantiomer.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. The disclosure includes diastereomers of the compounds described herein.

In some embodiments, the compounds and compositions of the disclosure may be enriched to provide predominantly one diastereomer of a compound disclosed herein. A diastereomerically enriched mixture may comprise, for example, at least 60 mol percent of one diastereomer, or more preferably at least 75, 85, 95, 96, 97, 98, 99, or even 100 mol percent.

The compounds described herein further include all pharmaceutically acceptable isotopically labeled compounds. An "isotopically" or "radio-labeled" compound is a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, are useful in drug and/or substrate tissue distribution studies. The radioactive isotopes tritium, i.e., $^{3}H$, and carbon 14, i.e., $^{14}C$, are particularly useful for this purpose in view of their ease of incorporation and ready means of detection. Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances. Suitable isotopes that may be incorporated in compounds described herein include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}C_{1}$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$, and $^{13}N$, can be useful in Positron Emission Topography (PET) studies.

An "effective amount" when used in connection with a compound is an amount effective for treating or preventing a disease in a subject as described herein.

The term "carrier," as used in this disclosure, encompasses excipients and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "prevent" or "preventing" with regard to a subject refers to keeping a disease or disorder from afflicting the subject. Preventing includes prophylactic treatment. For instance, preventing can include administering to the subject one or more compounds disclosed herein before a subject is afflicted with a disease and the administration will keep the subject from being afflicted with the disease.

The term "disorder" is used in this disclosure to mean, and is used interchangeably with, the terms disease, condition, or illness, unless otherwise indicated.

The term "administer," "administering," or "administration" as used in this disclosure refers to either directly administering one or more disclosed compounds or a pharmaceutically acceptable salt of one or more disclosed compounds or a composition comprising one or more disclosed compounds to a subject, or administering a prodrug derivative or analog of the compound or a pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

Compounds of the Disclosure

The present disclosure provides compounds of Formula Ia:

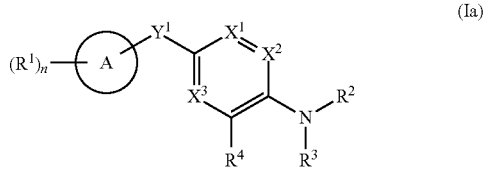

(Ia)

and pharmaceutically acceptable salts, prodrugs, solvates, hydrates, tautomers, and isomers thereof, wherein:

$X^1$ is N or CH;

$X^2$ is N or CH;

$X^3$ is N or CH;

wherein at least one of $X^1$, $X^2$, or $X^3$ is N;

$Y^1$ is —S— or a direct bond,

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)R, —NHC(O)$NHR^5$, —$NHS(O)_2R^5$, —$NHS(O)_2NHR^5$, —$S(O)_2OH$, —$C(O)OR^5$, —$NH(CH_2)_nOH$, —C(O)NH$(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —NR⁵R⁶C(O)—, heterocycle, aryl, heteroaryl, —(CH₂)ₙ OH, —C₁-C₆alkyl, CF₃, CHF₂, or CH₂F; and n is independently 0, 1, 2, 3, 4, 5, 6, 7, 8, 9, or 10.

The present disclosure provides compounds of Formula I,

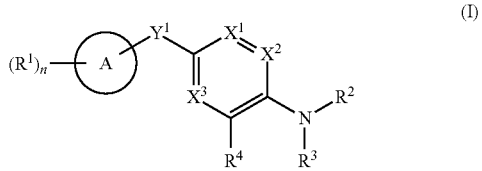

(I)

and pharmaceutically acceptable salts, prodrugs, solvates, hydrates, tautomers, and isomers thereof, wherein:

$X^1$ is N or CH;

$X^2$ is N or CH;

$X^3$ is N or CH;

wherein at least one of $X^1$, $X^2$, or $X^3$ is N;

$Y^1$ is —S— or a direct bond,

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, or —NR⁵C(O)R⁶, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

$R^2$ and $R^3$ are independently selected from the group consisting of —H, -D, —OH, —C₁-C₆alkyl, a 3- to 12-membered monocyclic or polycyclic heterocycle, a 5- to 12-membered spiroheterocycle, C₃-C₈cycloalkyl, or —(CH₂)ₙ—R^b, wherein each alkyl, heterocycle, or cycloalkyl is optionally substituted with one or more —C₁-C₆alkyl, —OH, —NH₂, —OR^b, —NHR^b, —(CH₂)ₙOH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —C₁-C₆alkyl, halogen, —OH, —OR^b, —NH₂, —NHR^b, heteroaryl, heterocyclyl, —(CH₂)ₙNH₂, —(CH₂)ₙOH, —COOR^b, —CONHR^b, —CONH(CH₂)ₙCOOR^b, —NHCOOR^b, —CF₃, —CHF₂, —CH₂F, or =O;

$R^4$ is —H, -D, —C₁-C₆alkyl, —C₁-C₆haloalkyl, —C₁-C₆hydroxyalkyl —CF₂OH, —CHFOH, —NH—NHR⁵, —NH—OR⁵, —O—NR⁵R⁶, —NHR⁵, —OR⁵, —NHC(O)R, —NHC(O)NHR⁵, —NHS(O)₂R⁵, —NHS(O)₂NHR⁵, —S(O)₂OH, —C(O)OR⁵, —NH(CH₂)ₙOH, —C(O)NH(CH₂)ₙOH, —C(O)NH(CH₂)ₙR^b, —C(O)R^b, —NH₂, —OH, —CN, —C(O)NR⁵R⁶, —S(O)₂NR⁵R⁶, C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH₂, —OR^b, halogen, or oxo; wherein each aryl or heteroaryl is optionally substituted with one or more —OH, —NH₂, or halogen;

$R^5$ and $R^6$ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, and —CN;

$R^7$ and $R^8$ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

$R^b$ is independently —H, -D, —C₁-C₆alkyl, —C₁-C₆cycloalkyl, —C₂-C₆alkenyl, —(CH₂)ₙ-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH₂)ₙ OH, —C₁-C₆alkyl, CF₃, CHF₂, or CH₂F; and n is independently 0, 1, 2, 3, 4, 5, 6, 7, 8, 9, or 10.

The present disclosure provides compounds of Formula IIa,

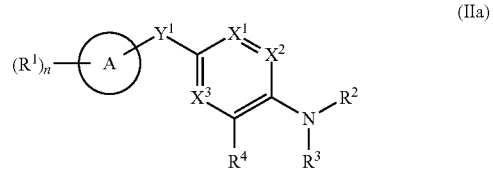

(IIa)

and pharmaceutically acceptable salts, prodrugs, solvates, hydrates, tautomers, and isomers thereof, wherein:

$X^1$ is N or CH;

$X^2$ is N or CH;

$X^3$ is N or CH;

wherein at least one of $X^1$, $X^2$, or $X^3$ is N;

$Y^1$ is a direct bond;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, or —NR⁵C(O)R⁶, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

$R^2$ and $R^3$ are independently selected from the group consisting of —H, -D, —OH, —C₁-C₆alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n OH$, —$COOR^b$, —$CONHR^b$, —$CONH(CH_2)_n COOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)R, —NHC(O)$NHR^5$, —$NHS(O)_2R^5$, —$NHS(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

The present disclosure provides compounds of Formula IIb,

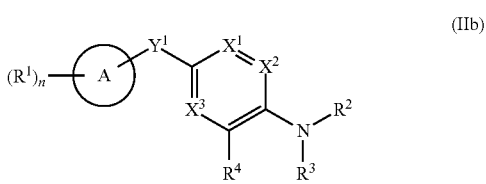

(IIb)

and pharmaceutically acceptable salts, prodrugs, solvates, hydrates, tautomers, and isomers thereof, wherein:

$X^1$ is N or CH;

$X^2$ is N or CH;

$X^3$ is N or CH;

wherein at least one of $X^1$, $X^2$, or $X^3$ is N;

$Y^1$ is —S—;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n OH$, —$COOR^b$, —$CONHR^b$, —$CONH(CH_2)_n COOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)R, —NHC(O)$NHR^5$, —$NHS(O)_2R^5$, —$NHS(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —NO₂, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

The present disclosure provides compounds of Formula IV:

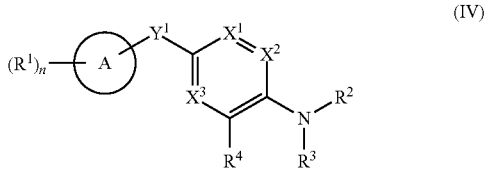

(IV)

and pharmaceutically acceptable salts, prodrugs, solvates, hydrates, tautomers, and isomers thereof, wherein:

$X^1$ is N or CH;

$X^2$ is N or CH;

$X^3$ is N or CH;

wherein at least one of $X^1$, $X^2$, or $X^3$ is N;

$Y^1$ is —S— or a direct bond,

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —NO₂, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO₂, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, heterocycle, or cycloalkyl is optionally substituted with one or more —$C_1$-$C_6$alkyl, —OH, —NH₂, —$OR^b$, —$NHR^b$, —$(CH_2)_nOH$, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —NH₂, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN; $R^4$ is —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —NHS(O)₂$NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —NH₂, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH₂, —$OR^b$, halogen, or oxo; wherein each aryl or heteroaryl is optionally substituted with one or more —OH, —NH₂, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —NO₂, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —NO₂, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

As described above for Formula Ia, I, and IV, $Y^1$ is —S— or a direct bond. In certain embodiments, $Y^1$ is —S—. In certain embodiments, $Y^1$ is a direct bond.

As described above, $X^1$ is N or CH. In certain embodiments, $X^1$ is N. In certain embodiments, $X^1$ is CH.

As described above, $X^2$ is N or CH. In certain embodiments, $X^2$ is N. In certain embodiments, $X^2$ is CH.

As described above, $X^3$ is N or CH. In certain embodiments, $X^3$ is N. In certain embodiments, $X^3$ is CH.

As described above, at least one of $X^1$, $X^2$, or $X^3$ is N. In certain embodiments, $X^1$ is N. In certain embodiments, $X^2$ is N. In certain embodiments, $X^3$ is N. In certain embodiments, $X^1$ is N and $X^2$ is N. In certain embodiments, $X^1$ is N and $X^3$ is N. In certain embodiments, $X^2$ is N and $X^3$ is N. In certain embodiments, $X^1$ is N; $X^2$ is N; and $X^3$ is N.

As described above, A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl.

In certain embodiments, A is 5- to 12-membered monocyclic or polycyclic cycloalkyl. In certain embodiments, A is 5- to 12-membered monocyclic or polycyclic heterocycloalkyl. In certain embodiments, A is 5- to 12-membered monocyclic or polycyclic aryl. In certain embodiments, A is 5- to 12-membered monocyclic or polycyclic heteroaryl.

In certain embodiments, A is a monocyclic heteroaryl. In certain embodiments, A is a monocyclic aryl. In certain embodiments, A is a polycyclic heteroaryl. In certain embodiments, A is a polycyclic heterocycloalkyl.

In certain embodiments, A is selected from:

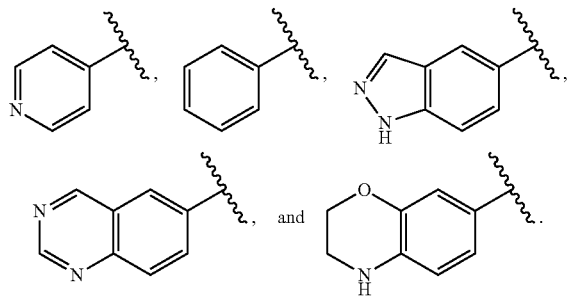 [SMILES: *c1ccncc1 ; *c1ccccc1 ; *c1ccc2[nH]ncc2c1 ; *c1ccc2ncncc2c1 ; *c1ccc2c(c1)OCCN2]

In certain embodiments, A is selected from:

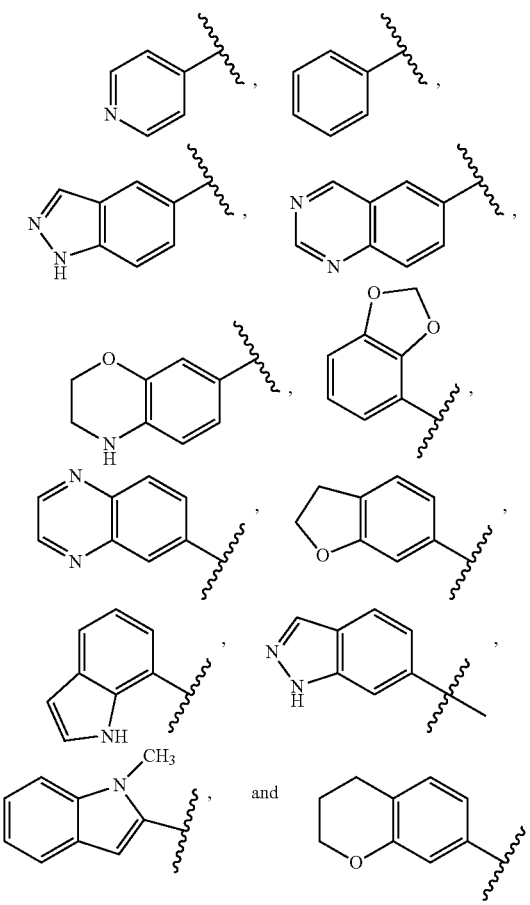

As described above for formula I, IIa, and IIb, $R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl.

In certain embodiments, each $R^1$ is selected from the group consisting of —H, halogen, —$C_1$-$C_6$alkyl, and —$NR^5R^6$. In certain embodiments, $R^5$ and $R^6$ are H.

As described above for formula Ia and IV, $R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —SR, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl. In certain embodiments, each $R^1$ is an optionally substituted 3- to 12-membered monocyclic or polycyclic heterocycle. In certain embodiments, each $R^1$ is 3- to 12-membered monocyclic or polycyclic heterocycle substituted with heterocycle or —$S(O)_2R^5$. In certain embodiments, each $R^1$ is selected from the group consisting of halogen, —$C_1$-$C_6$alkyl, —$OR^6$, —CN, —$C(O)NR^5R^6$, and —$NR^5R^6$. In certain embodiments, $R^5$ and $R^6$ are H.

As described above, n is independently 0, 1, 2, 3, 4, 5, 6, 7, 8, 9, or 10.

As described above, $R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN. In certain embodiments, $R^5$ and $R^6$ are H.

In certain embodiments, A (shown with $R^1$) are selected from:

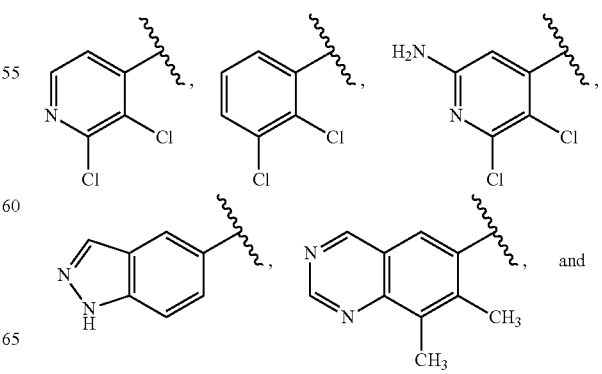

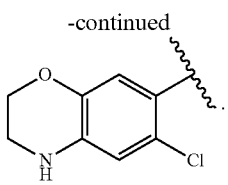

As described above for formula Ia, I, IIa, and IIb, $R^4$ is —H, -D, —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —S(O)$_2$OH, —C(O)$OR^5$, —NH(CH$_2$)$_n$OH, —C(O)NH(CH$_2$)$_n$OH, —C(O)NH(CH$_2$)$_n$R, —C(O)$R^b$, —$NH_2$, —OH, —CN, —C(O)$NR^5R^6$, —S(O)$_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen.

In certain embodiments, $R^4$ is —H, -D, or —$C_1$-$C_6$alkyl, wherein each alkyl is optionally substituted with one or more —OH, —$NH_2$, halogen, or oxo. In certain embodiments, $R^4$ is an optionally substituted —$C_1$-$C_6$alkyl. In certain embodiments, $R^4$ is —$C_1$-$C_6$alkyl substituted with —OH. In certain embodiments, $R^4$ is-$CH_2$—OH. In certain embodiments, $R^4$ is —$C_1$-$C_6$alkyl substituted with one or more halogen. In certain embodiments, $R^4$ is —$C_1$-$C_6$alkyl substituted with one or more fluoro. In certain embodiments, $R^4$ is —$CHF_2$.

As described above for formula IV, $R^4$ is —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —S(O)$_2$OH, —C(O)$OR^5$, —NH(CH$_2$)$_n$OH, —C(O)NH(CH$_2$)$_n$OH, —C(O)NH(CH$_2$)$_n$R, —C(O)R, —$NH_2$, —OH, —CN, —C(O)$NR^5R^6$, —S(O)$_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen. In certain embodiments, $R^4$ is an optionally substituted —$C_1$-$C_6$alkyl. In certain embodiments, $R^4$ is —$C_1$-$C_6$alkyl substituted with —OH. In certain embodiments, $R^4$ is-$CH_2$—OH. In certain embodiments, $R^4$ is —$C_1$-$C_6$alkyl substituted with one or more halogen. In certain embodiments, $R^4$ is —$C_1$-$C_6$alkyl substituted with one or more fluoro. In certain embodiments, $R^4$ is —$CHF_2$.

As described above, $R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —(CH$_2$)$_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —(CH$_2$)$_n$OH, heterocyclyl, or spiroheterocyclyl. In certain embodiments, $R^2$ or $R^3$ is —(CH$_2$)$_n$C(O)$NR^5R^6$.

As described above, $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —(CH$_2$)$_n$NH$_2$, —(CH$_2$)$_n$OH, —COO$R^b$, —CONH$R^b$, —CONH(CH$_2$)$_n$COO$R^b$, —NHCOO$R^b$, —$CF_3$, —$CHF_2$, —$CH_2F$, or =O. In certain embodiments, $R^3$ can combine with $R^2$ to form an optionally substituted heteroaryl or an optionally substituted heterocyclyl, wherein wherein the heteroaryl and heterocyclyl are optionally substituted with —CN.

In certain embodiments, $R^3$ can combine with $R^2$ to form a 3- to 12-membered optionally substituted monocyclic heterocycle. In certain embodiments, $R^3$ can combine with $R^2$ to form a 3- to 12-membered optionally substituted polycyclic heterocycle. In certain embodiments, $R^3$ can combine with $R^2$ to form a 5- to 12-membered optionally substituted spiroheterocycle.

In certain embodiments, $R^3$ can combine with $R^2$ to form 3- to 12-membered monocyclic or polycyclic heterocycle, wherein the heterocycle is optionally substituted with more —$C_1$-$C_6$alkyl, halogen, —OH, —$OR^b$, —$NH_2$, —NR, heteroaryl, heterocyclyl, —(CH$_2$)$_n$NH$_2$, —(CH$_2$)$_n$OH, —COO$R^b$, —CONH$R^b$, —CONH(CH$_2$)$_n$COO$R^b$, —NHCOO$R^b$, —$CF_3$, —$CHF_2$, —$CH_2F$, or =O.

In certain embodiments, $R^3$ can combine with $R^2$ to form 3- to 12-membered monocyclic or polycyclic heterocycle, wherein the heterocycle is optionally substituted with —$C_1$-$C_6$alkyl, —$OR^b$, or —$NH_2$.

In certain embodiments, $R^3$ can combine with $R^2$ to form a 5- to 12-membered spiroheterocycle, wherein the spiroheterocycle is optionally substituted with more —$C_1$-$C_6$alkyl, halogen, —OH, —$OR^b$, —$NH_2$, —$NHR^b$, heteroaryl, heterocyclyl, —(CH$_2$)$_n$NH$_2$, —(CH$_2$)$_n$OH, —COO$R^b$, —CONH$R^b$, —CONH(CH$_2$)$_n$COO$R^b$, —NHCOO$R^b$, —$CF_3$, —$CHF_2$, —$CH_2F$, or =O.

In certain embodiments, $R^3$ can combine with $R^2$ to form 5- to 12-membered spiroheterocycle, wherein the spirocycle is optionally substituted with —$C_1$-$C_6$alkyl, —$OR^b$, or —$NH_2$.

In certain embodiments, $R^3$ can combine with $R^2$ to form a moiety selected from:

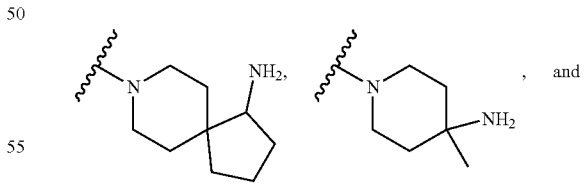

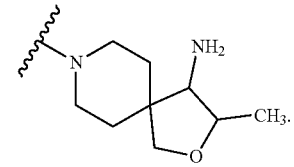

In certain embodiments, R³ can combine with R² to form a moiety selected from:

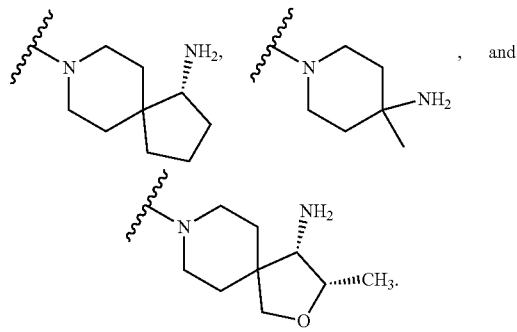

The present disclosure provides compounds of Formula III,

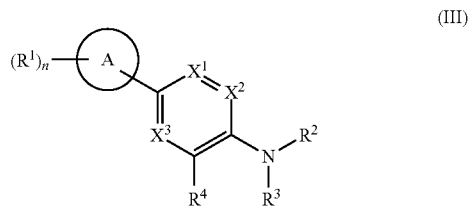

and pharmaceutically acceptable salts, prodrugs, solvates, hydrates, tautomers, and isomers thereof, wherein:

$X^1$ is N or CH;
$X^2$ is N or CH;
$X^3$ is N or CH;
wherein at least one of $X^1$, $X^2$, or $X^3$ is N;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, or —NR⁵C(O)R⁶, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² and R³ are independently selected from the group consisting of —H, -D, —OH, —C₁-C₆alkyl, a 3- to 12-membered monocyclic or polycyclic heterocycle, a 5- to 12-membered spiroheterocycle, C₃-C₈cycloalkyl, or —(CH₂)ₙ—R^b, wherein each alkyl, heterocycle, or cycloalkyl is optionally substituted with one or more —C₁-C₆alkyl, —OH, —NH₂, —OR^b, —NHR^b, —(CH₂)ₙOH, heterocyclyl, or spiroheterocyclyl; or R³ can combine with R² to form a 3- to 12-membered monocyclic or polycyclic heterocycle, or a 5- to 12-membered spiroheterocycle, wherein each heterocycle or spiroheterocycle is optionally substituted with one or more —C₁-C₆alkyl, halogen, —OH, —OR^b, —NH₂, —NHR^b, heteroaryl, heterocyclyl, —(CH₂)ₙNH₂, —(CH₂)ₙOH, —COOR^b, —CONHR^b, —CONH(CH₂)ₙCOOR^b, —NHCOOR^b, —CF₃, —CHF₂, —CH₂F, or =O;

R⁴ is —H, -D, or —C₁-C₆alkyl, wherein each alkyl is optionally substituted with one or more —OH, —NH₂, halogen, or oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

R^b is independently —H, -D, —C₁-C₆alkyl, —C₁-C₆cycloalkyl, —C₂-C₆alkenyl, —(CH₂)ₙ-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH₂)ₙOH, —C₁-C₆alkyl, CF₃, CHF₂, or CH₂F; and n is independently 0, 1, 2, 3, 4, 5, 6, 7, 8, 9, or 10.

The present disclosure provides compounds of Formula V:

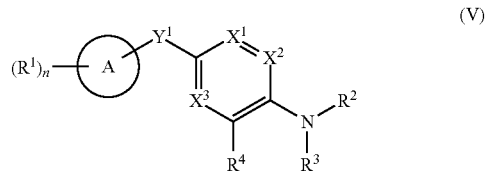

and pharmaceutically acceptable salts, prodrugs, solvates, hydrates, tautomers, and isomers thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond, A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R, —CO₂R⁵, —C(O)NR⁵R⁶, —NR⁵C(O)R⁶, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² and R³ are independently selected from the group consisting of —H, -D, —OH, —C₁-C₆alkyl, a 3- to 12-membered monocyclic or polycyclic heterocycle, a 5- to 12-membered spiroheterocycle, C₃-C₈cycloalkyl, —(CH₂)ₙ—Rᵇ, or —(CH₂)ₙC(O)NR⁵R⁶, wherein each alkyl, heterocycle, or cycloalkyl is optionally substituted with one or more —C₁-C₆alkyl, —OH, —NH₂, —ORᵇ, —NHRᵇ, —(CH₂)ₙOH, heterocyclyl, or spiroheterocyclyl; or R³ can combine with R² to form a 3- to 12-membered monocyclic or polycyclic heterocycle, or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, optionally substituted heteroaryl, optionally substituted heterocyclyl, —(CH₂)ₙNH₂, —(CH₂)ₙOH, —COORᵇ, —CONHRᵇ, —CONH(CH₂)ₙCOORᵇ, —NHCOORᵇ, —O—C(O)—NR⁵R⁶, —CF₃, —CHF₂, —CH₂F, or =O; wherein the heteroaryl and heterocyclyl are optionally substituted with —CN;

R⁴ is-C₁-C₆alkyl, wherein each alkyl is optionally substituted with one or more —OH, —NH₂, halogen, or oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

Rᵇ is independently —H, -D, —C₁-C₆alkyl, —C₁-C₆cycloalkyl, —C₂-C₆alkenyl, —(CH₂)ₙ-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH₂)ₙ OH, —C₁-C₆alkyl, CF₃, CHF₂, or CH₂F; and n is independently 0, 1, 2, 3, 4, 5, 6, 7, 8, 9, or 10

The present disclosure provides compounds of Formula VI:

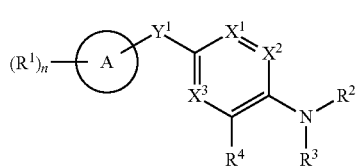

(VI)

and pharmaceutically acceptable salts, prodrugs, solvates, hydrates, tautomers, and isomers thereof, wherein:
X¹ is N or CH;
X² is N or CH;
X³ is N or CH;

wherein at least one of X¹, X², or X³ is N;

Y¹ is —S— or a direct bond,

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, —NR⁵C(O)R⁶, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ can combine with R² to form a 3- to 12-membered monocyclic or polycyclic heterocycle, or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, optionally substituted heteroaryl, optionally substituted heterocyclyl, —(CH₂)ₙNH₂, —(CH₂)ₙOH, —COORᵇ, —CONHRᵇ, —CONH(CH₂)ₙCOORᵇ, —NHCOORᵇ, —O—C(O)—NR⁵R⁶, —CF₃, —CHF₂, —CH₂F, or =O; wherein the heteroaryl and heterocyclyl are optionally substituted with —CN;

R⁴ is-C₁-C₆alkyl, wherein each alkyl is optionally substituted with one or more —OH, —NH₂, halogen, or oxo;

R⁵ and R⁶ are each independently, at each occurrence, selected from the group consisting of —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, and —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

Rᵇ is independently —H, -D, —C₁-C₆alkyl, —C₁-C₆cycloalkyl, —C₂-C₆alkenyl, —(CH₂)ₙ-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH₂)ₙ OH, —C₁-C₆alkyl, CF₃, CHF₂, or CH₂F; and n is independently 0, 1, 2, 3, 4, 5, 6, 7, 8, 9, or 10.

As described above in Formula III, V, and VI, X¹ is N or CH. In certain embodiments, X¹ is N. In certain embodiments, X¹ is CH.

As described above in Formula III, V, and VI, X² is N or CH. In certain embodiments, X² is N. In certain embodiments, X² is CH.

As described above in Formula III, V, and VI, $X^3$ is N or CH. In certain embodiments, $X^3$ is N. In certain embodiments, $X^3$ is CH.

As described above in Formula III, V, and VI, at least one of $X^1$, $X^2$, or $X^3$ is N. In certain embodiments, $X^1$ is N. In certain embodiments, $X^2$ is N. In certain embodiments, $X^3$ is N. In certain embodiments, $X^1$ is N and $X^2$ is N. In certain embodiments, $X^1$ is N and $X^3$ is N. In certain embodiments, $X^2$ is N and $X^3$ is N. In certain embodiments, $X^1$ is N; $X^2$ is N; and $X^3$ is N.

As described above in Formula III, V, and VI, A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl.

In certain embodiments, A is 5- to 12-membered monocyclic or polycyclic cycloalkyl. In certain embodiments, A is 5- to 12-membered monocyclic or polycyclic heterocycloalkyl. In certain embodiments, A is 5- to 12-membered monocyclic or polycyclic aryl. In certain embodiments, A is 5- to 12-membered monocyclic or polycyclic heteroaryl.

In certain embodiments, A is a monocyclic heteroaryl. In certain embodiments, A is a monocyclic aryl. In certain embodiments, A is a polycyclic heteroaryl. In certain embodiments, A is a polycyclic heterocycloalkyl.

In certain embodiments, A is selected from:

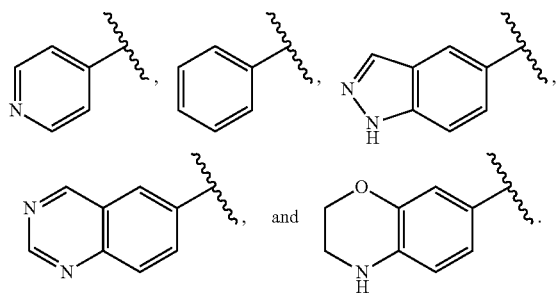

In certain embodiments, A is selected from:

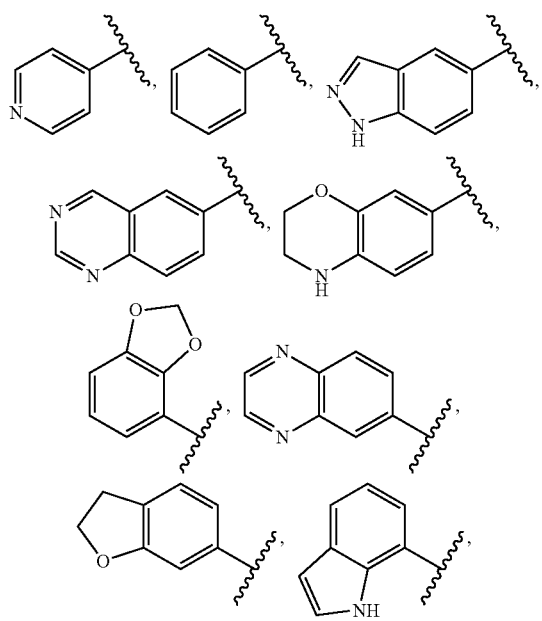

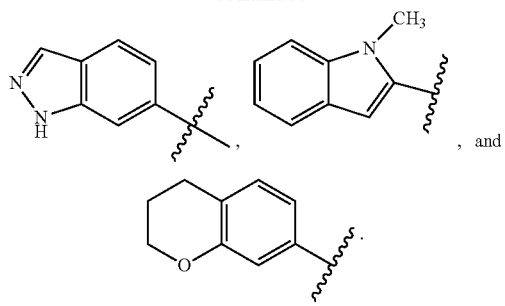

As described above in Formula III, $R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl.

In certain embodiments, each $R^1$ is selected from the group consisting of —H, halogen, —$C_1$-$C_6$alkyl, and —$NR^5R^6$. In certain embodiments, $R^5$ and $R^6$ are H.

As described above in Formula V and VI, $R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl. In certain embodiments, each $R^1$ is an optionally substituted 3- to 12-membered monocyclic or polycyclic heterocycle. In certain embodiments, each $R^1$ is 3- to 12-membered monocyclic or polycyclic heterocycle substituted with heterocycle or —$S(O)_2R^5$. In certain embodiments, each $R^1$ is selected from the group consisting of halogen, —$C_1$-$C_6$alkyl, —$OR^6$, —CN, —$C(O)NR^5R^6$, and —$NR^5R^6$. In certain embodiments, $R^5$ and $R^6$ are H.

As described above in Formula III, V, and VI, n is independently 0, 1, 2, 3, 4, 5, 6, 7, 8, 9, or 10.

As described above in Formula III, V, and VI, $R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN. In certain embodiments, $R^5$ and $R^6$ are H.

In certain embodiments, A (shown with $R^1$) are selected from:

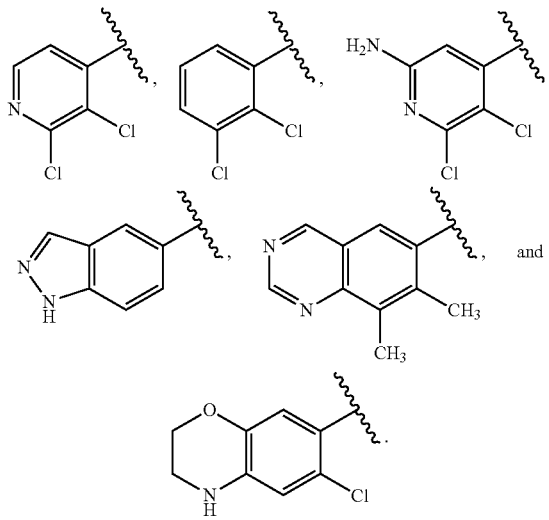

As described above in Formula III, $R^4$ is —H, -D, or —$C_1$-$C_6$alkyl, wherein each alkyl is optionally substituted with one or more —OH, —$NH_2$, halogen, or oxo. In certain embodiments, $R^4$ is an optionally substituted —$C_1$-$C_6$alkyl. In certain embodiments, $R^4$ is —$C_1$-$C_6$alkyl substituted with —OH. In certain embodiments, $R^4$ is-$CH_2$—OH. In certain embodiments, $R^4$ is —$C_1$-$C_6$alkyl substituted with one or more halogen. In certain embodiments, $R^4$ is —$C_1$-$C_6$alkyl substituted with one or more fluoro. In certain embodiments, $R^4$ is —$CHF_2$.

As described above in Formula V and VI, $R^4$ is-$C_1$-$C_6$alkyl, wherein each alkyl is optionally substituted with one or more —OH, —$NH_2$, halogen, or oxo. In certain embodiments, $R^4$ is —$C_1$-$C_6$alkyl substituted with —OH. In certain embodiments, $R^4$ is-$CH_2$—OH. In certain embodiments, $R^4$ is —$C_1$-$C_6$alkyl substituted with one or more halogen. In certain embodiments, $R^4$ is —$C_1$-$C_6$alkyl substituted with one or more fluoro. In certain embodiments, $R^4$ is —$CHF_2$.

As described above in Formula III and V, $R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl. In certain embodiments, $R^2$ or $R^3$ can be —$(CH_2)_nC(O)NR^5R^6$.

As described above in Formula III, V, and VI, $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O. In certain embodiments, $R^3$ can combine with $R^2$ to form an optionally substituted heteroaryl or an optionally substituted heterocyclyl, wherein wherein the heteroaryl and heterocyclyl are optionally substituted with —CN.

In certain embodiments, $R^3$ can combine with $R^2$ to form a 3- to 12-membered optionally substituted monocyclic heterocycle. In certain embodiments, $R^3$ can combine with $R^2$ to form a 3- to 12-membered optionally substituted polycyclic heterocycle. In certain embodiments, $R^3$ can combine with $R^2$ to form a 5- to 12-membered optionally substituted spiroheterocycle.

In certain embodiments, $R^3$ can combine with $R^2$ to form 3- to 12-membered monocyclic or polycyclic heterocycle, wherein the heterocycle is optionally substituted with more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

In certain embodiments, $R^3$ can combine with $R^2$ to form 3- to 12-membered monocyclic or polycyclic heterocycle, wherein the heterocycle is optionally substituted with —$C_1$-$C_6$alkyl, —$OR^b$, or —$NH_2$.

In certain embodiments, $R^3$ can combine with $R^2$ to form a 5- to 12-membered spiroheterocycle, wherein the spiroheterocycle is optionally substituted with more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONR^b$, —$CONH(CH_2)_nCOOR^b$, —$NHCOOR^b$, —$CF_3$, —$CHF_2$, —$CH_2F$, or =O.

In certain embodiments, $R^3$ can combine with $R^2$ to form 5- to 12-membered spiroheterocycle, wherein the spirocycle is optionally substituted with —$C_1$-$C_6$alkyl, —$OR^b$, or —$NH_2$.

In certain embodiments, $R^3$ can combine with $R^2$ to form a moiety selected from:

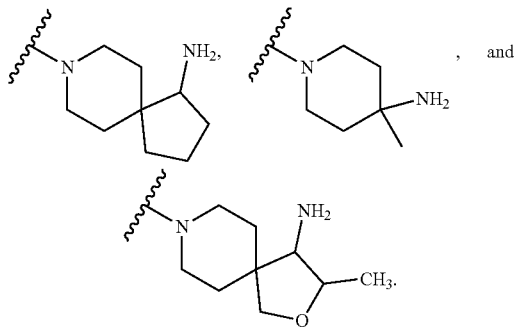

In certain embodiments, $R^3$ can combine with $R^2$ to form a moiety selected from:

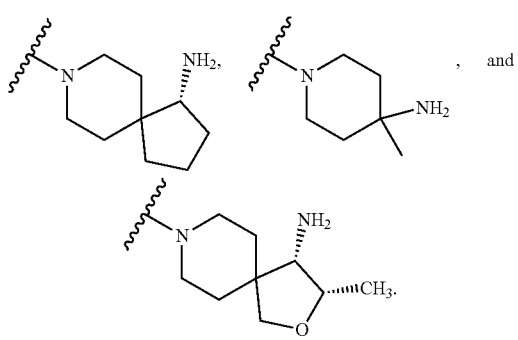

The present disclosure provides a compound of Formula Ia, I, IIa, IIb, III, IV, V, and VI having one, two, three, four, or more of the following features:

a) $X^1$ is CH; and $X^2$ and $X^3$ are N;
b) A is monocyclic or polycyclic optionally substituted heteroaryl;
c) $R^1$ is independently, at each occurrence, —H, —$C_1$-$C_6$alkyl, halogen, or —$NH_2$;
d) $R^3$ can combine with $R^2$ to form a 5- to 12-membered optionally substituted spiroheterocycle; and
e) $R^4$ is —$CH_2$—OH.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted heteroaryl;
c) $R^1$ is independently, at each occurrence, —H, —$C_1$-$C_6$alkyl, halogen, or —$NH_2$;
d) $R^3$ can combine with $R^2$ to form a form 3- to 12-membered monocyclic or polycyclic optionally substituted heterocycle; and
e) $R^4$ is —$CH_2$—OH.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted aryl;
c) $R^1$ is independently, at each occurrence, —H, —$C_1$-$C_6$alkyl, halogen, or —$NH_2$;
d) $R^3$ can combine with $R^2$ to form a 5- to 12-membered optionally substituted spiroheterocycle; and
e) $R^4$ is —$CH_2$—OH.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted aryl;
c) $R^1$ is independently, at each occurrence, —H, —$C_1$-$C_6$alkyl, halogen, or —$NH_2$;
d) $R^3$ can combine with $R^2$ to form a form 3- to 12-membered monocyclic or polycyclic optionally substituted heterocycle; and
e) $R^4$ is —$CH_2$—OH.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted heteroaryl;
c) $R^1$ is independently, at each occurrence, —H, —$C_1$-$C_6$alkyl, halogen, or —$NH_2$;
d) $R^3$ can combine with $R^2$ to form a 5- to 12-membered optionally substituted spiroheterocycle; and
e) $R^4$ is —$C_1$-$C_6$alkyl substituted with one or more halogen.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted heteroaryl;
c) $R^1$ is independently, at each occurrence, —H, —$C_1$-$C_6$alkyl, halogen, or —$NH_2$;
d) $R^3$ can combine with $R^2$ to form a form 3- to 12-membered monocyclic or polycyclic optionally substituted heterocycle; and
e) $R^4$ is —$C_1$-$C_6$alkyl substituted with one or more halogen.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted aryl;
c) $R^1$ is independently, at each occurrence, —H, —$C_1$-$C_6$alkyl, halogen, or —$NH_2$;
d) $R^3$ can combine with $R^2$ to form a 5- to 12-membered optionally substituted spiroheterocycle; and
e) $R^4$ is —$C_1$-$C_6$alkyl substituted with one or more halogen.

The present disclosure provides a compound of Formula Ia, I, IIa, IIb, III, IV, V, and VI, having one, two, three, four, or more of the following features:
a) $X^1$ is CH; and $X^2$ and $X^3$ are N;
b) A is monocyclic or polycyclic optionally substituted aryl;
c) $R^1$ is independently, at each occurrence, —H, —$C_1$-$C_6$alkyl, halogen, or —$NH_2$;
d) $R^3$ can combine with $R^2$ to form a form 3- to 12-membered monocyclic or polycyclic optionally substituted heterocycle; and
e) $R^4$ is —$C_1$-$C_6$alkyl substituted with one or more halogen.

The present disclosure provides a compound of Formula Ia, I, IIa, IIb, III, IV, V, and VI having one, two, three, four, or more of the following features:
a) $X^1$ is CH; and one of $X^2$ and $X^3$ is N;
b) A is monocyclic or polycyclic optionally substituted heteroaryl;
c) $R^1$ is independently, at each occurrence, —H, —$C_1$-$C_6$alkyl, halogen, or —$NH_2$;
d) $R^3$ can combine with $R^2$ to form a 5- to 12-membered optionally substituted spiroheterocycle; and
e) $R^4$ is —$CH_2$—OH or a —$C_1$-$C_6$alkyl substituted with one or more halogen.

The present disclosure provides a compound of Formula Ia, I, IIa, IIb, III, IV, V, and VI, having one, two, three, four, or more of the following features:
a) $X^1$ is CH; and one of $X^2$ and $X^3$ is N;
b) A is monocyclic or polycyclic optionally substituted heteroaryl;
c) $R^1$ is independently, at each occurrence, —H, —$C_1$-$C_6$alkyl, halogen, or —$NH_2$;
d) $R^3$ can combine with $R^2$ to form a form 3- to 12-membered monocyclic or polycyclic optionally substituted heterocycle; and
e) $R^4$ is —$CH_2$—OH or a —$C_1$-$C_6$alkyl substituted with one or more halogen.

The present disclosure provides a compound of Formula Ia, I, IIa, IIb, III, IV, V, and VI, having one, two, three, four, or more of the following features:
a) $X^1$ is CH; and one of $X^2$ and $X^3$ is N;
b) A is monocyclic or polycyclic optionally substituted aryl;
c) $R^1$ is independently, at each occurrence, —H, —$C_1$-$C_6$alkyl, halogen, or —$NH_2$;
d) $R^3$ can combine with $R^2$ to form a 5- to 12-membered optionally substituted spiroheterocycle; and
e) $R^4$ is —$CH_2$—OH or a —$C_1$-$C_6$alkyl substituted with one or more halogen.

The present disclosure provides a compound of Formula Ia, I, IIa, IIb, III, IV, V, and VI, having one, two, three, four, or more of the following features:

a) X¹ is CH; and one of X² and X³ is N;
b) A is monocyclic or polycyclic optionally substituted aryl;
c) R¹ is independently, at each occurrence, —H, —C₁-C₆alkyl, halogen, or —NH₂;
d) R³ can combine with R² to form a form 3- to 12-membered monocyclic or polycyclic optionally substituted heterocycle; and
e) R⁴ is —CH₂—OH or a —C₁-C₆alkyl substituted with one or more halogen.

The present disclosure provides a compound selected from:

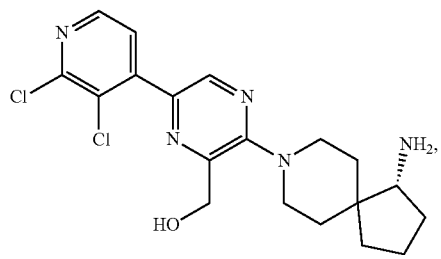
(1)

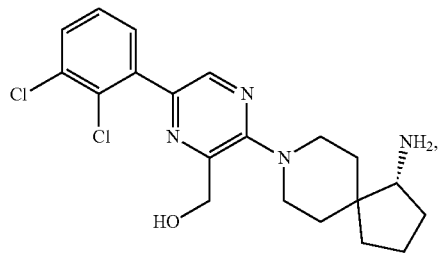
(2)

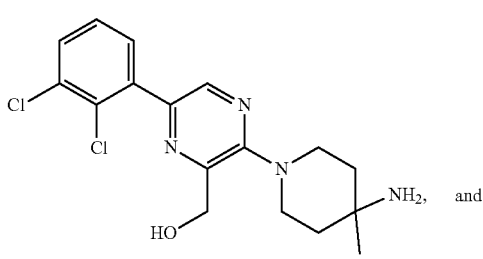
(3)

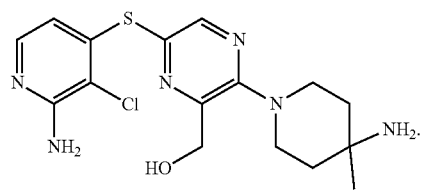
(4)

and pharmaceutically acceptable salts, prodrugs, solvates, hydrates, tautomers, or isomers thereof.

The present disclosure provides a compound selected from:

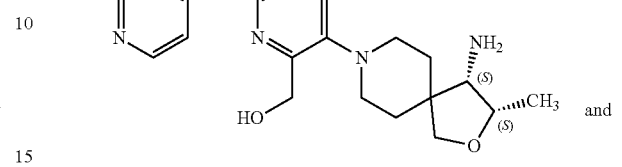
(5)

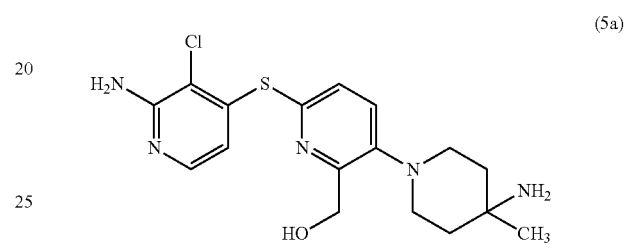
(5a)

and pharmaceutically acceptable salts, prodrugs, solvates, hydrates, tautomers, or isomers thereof.

The present disclosure provides a compound selected from:

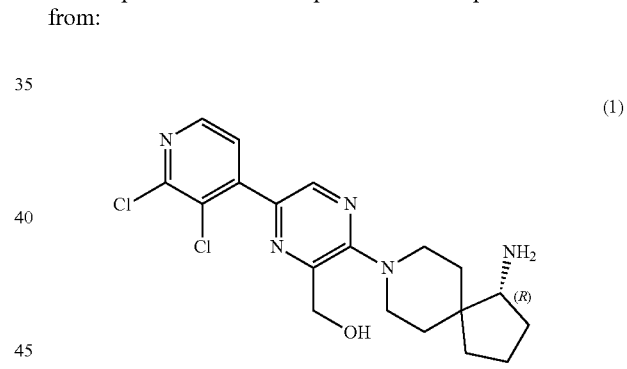
(1)

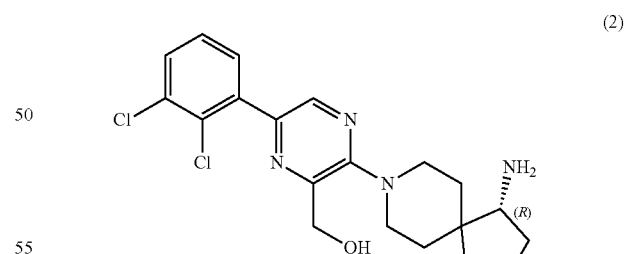
(2)

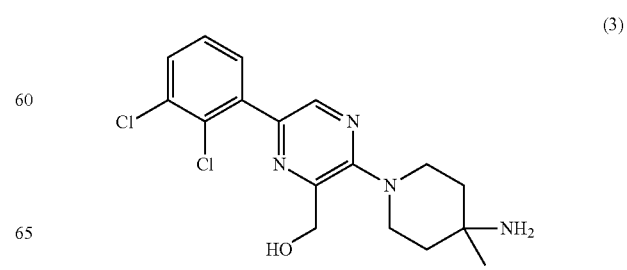
(3)

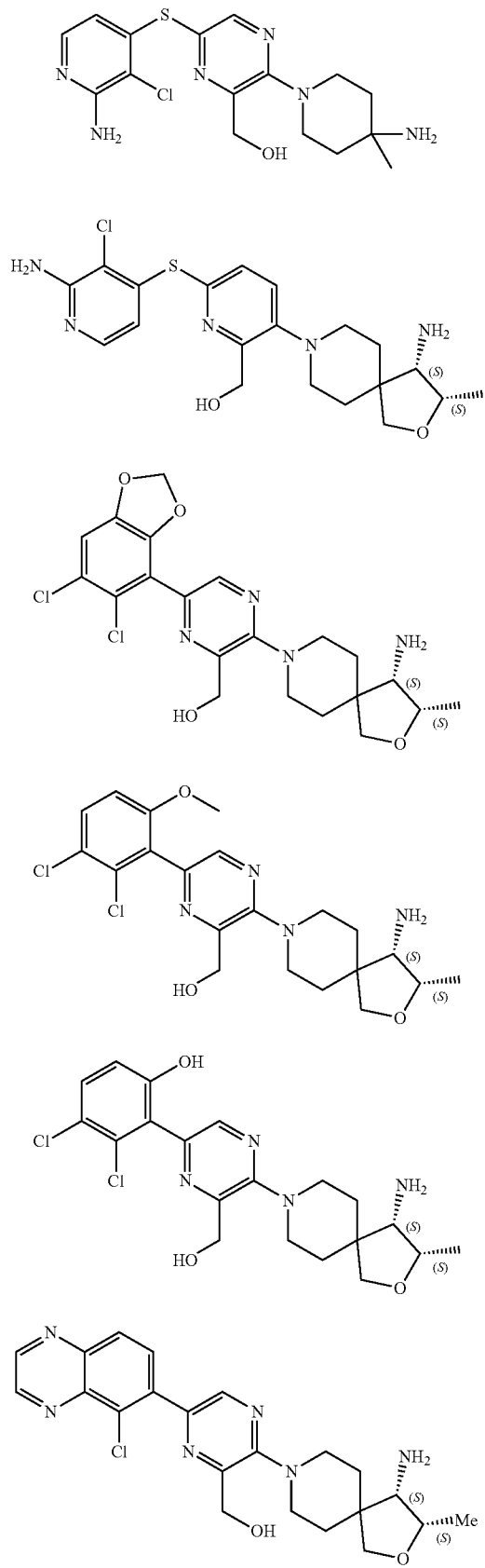
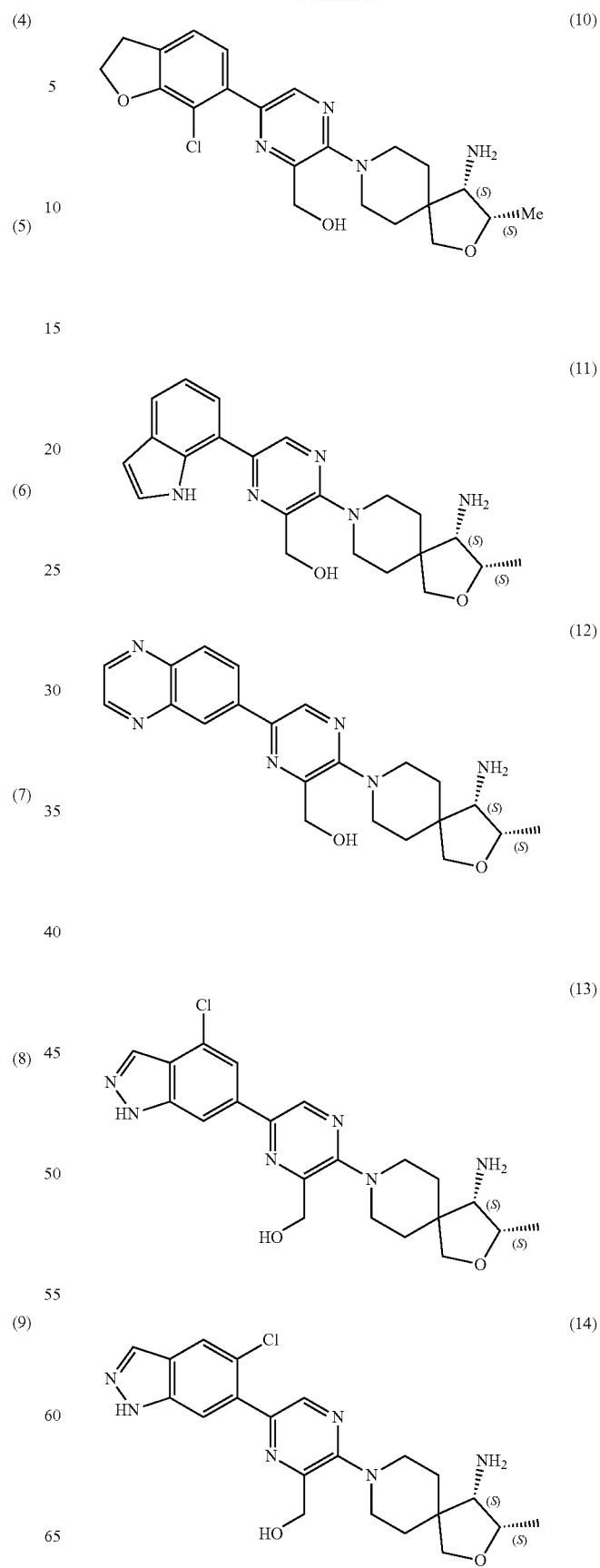

49
-continued
(15)
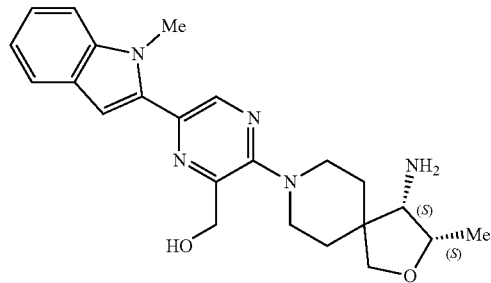
(16)
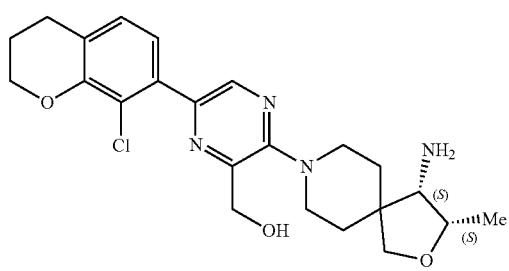
(17)
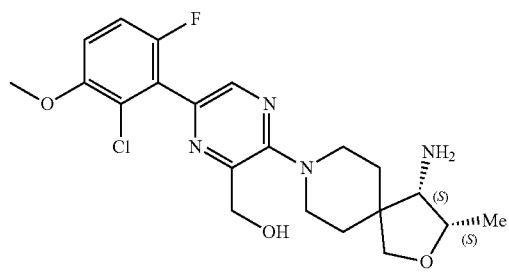
(18)
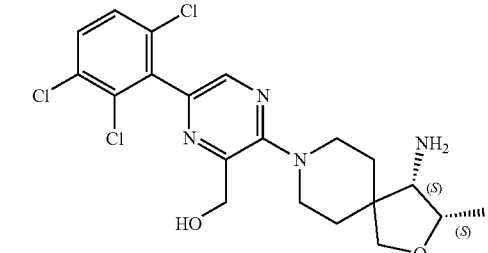
(19)
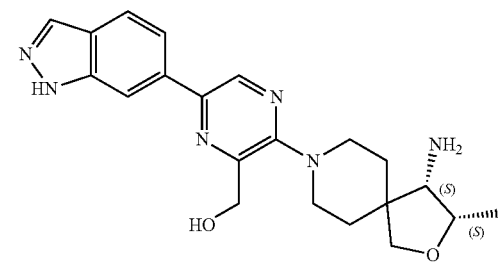
50
-continued
(20)
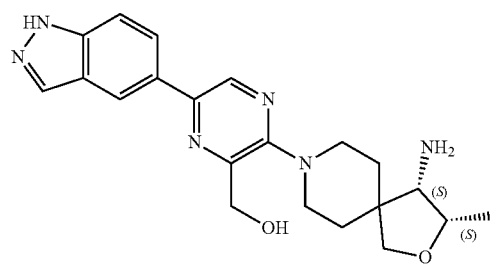
(21)
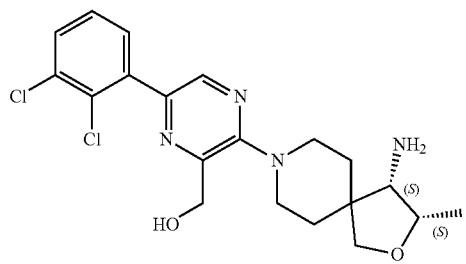
(22)
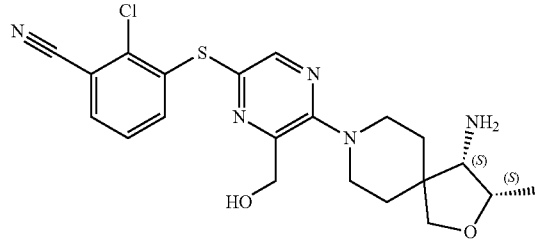
(23)
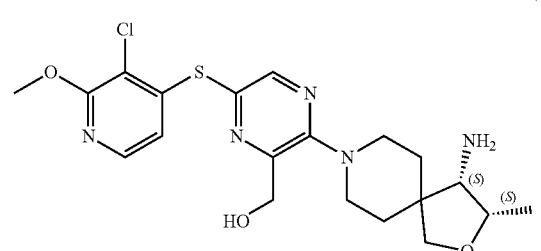
(24)
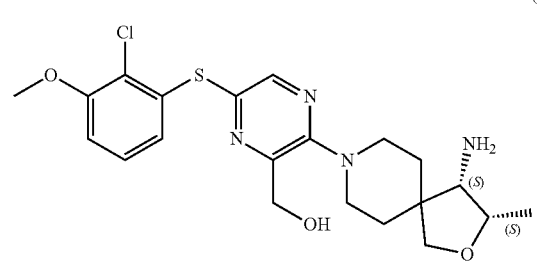
(25)

(26) 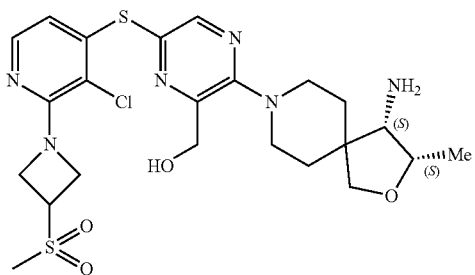

(27) 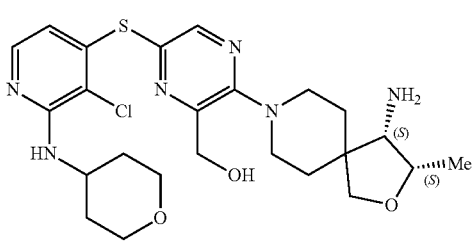

(28) 

(29) 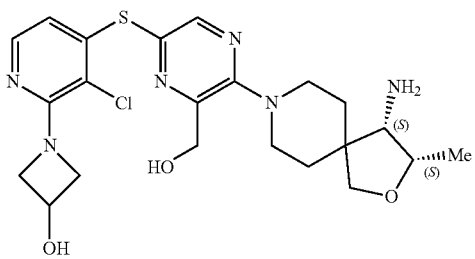

(30) 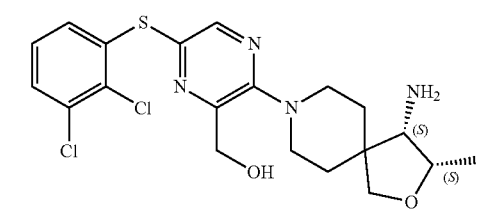

(31) 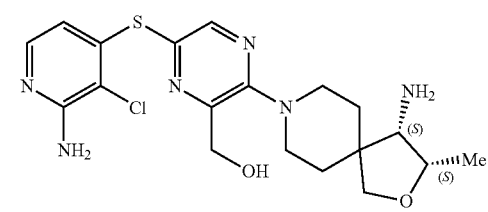

(32) 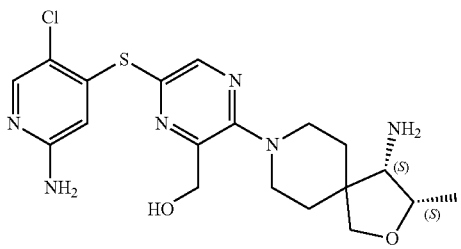

(33) 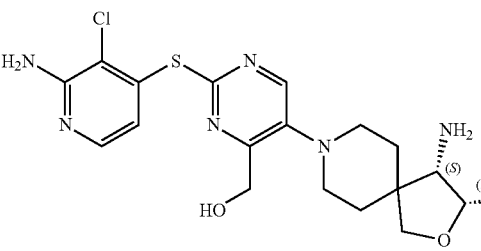

and pharmaceutically acceptable salts, prodrugs, solvates, hydrates, tautomers, and isomers thereof.

The present disclosure provides a compound selected from

(34) 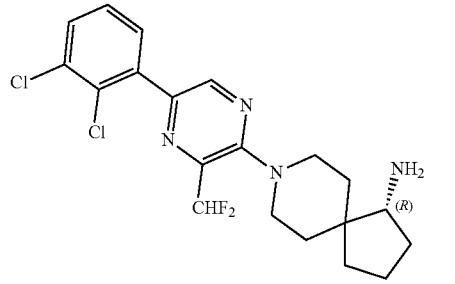

(35) 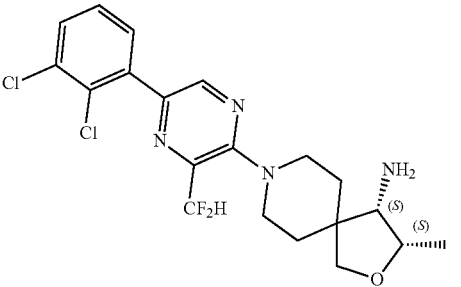

and pharmaceutically acceptable salts, prodrugs, solvates, hydrates, tautomers, and isomers thereof.

Methods of Synthesizing the Disclosed Compounds

The compounds of the present disclosure may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in any of the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present disclosure can be prepared in a number of ways well known to those skilled in the art of organic synthesis. By way of example, compounds of the disclosure can be synthesized using the methods described below, together with synthetic methods known in the art of synthetic organic chemistry, or variations thereon as appreciated by those skilled in the art. These methods include but are not limited to those methods described below.

Scheme 1. General synthesis of (3-amino-6-phenylpyrazin-2-yl)methanol

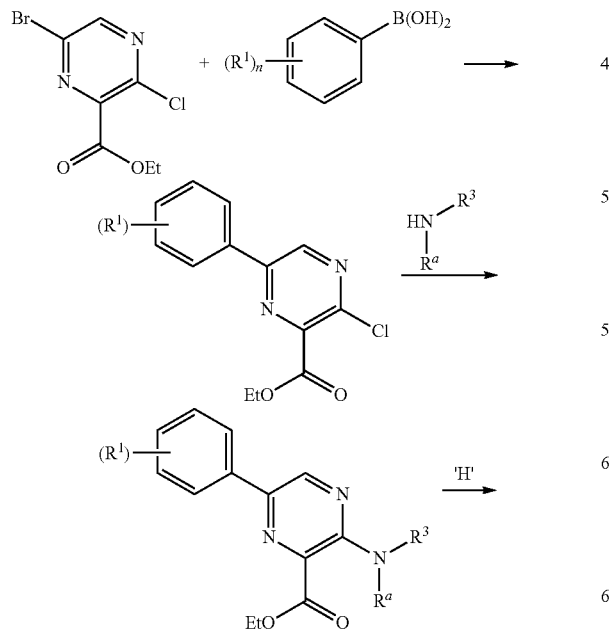

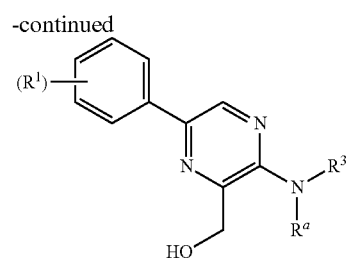

A genera synthesis of (3-amino-6-phenylpyrazin-2-yl) methano is outlined in Scheme 1. 3-Chloro-6-phenylpyrazine-2-ethylcarboxylate can be coupled to a substituted aryl- or heteroaryl boronic acid in the presence of a palladium catalyst (e.g., Pd(dppf)Cl$_2$). The resulting biaryl intermediate can then be coupled to a substituted primary or secondary amine under SNAr conditions, followed by reduction to give a (3-amino-6-phenylpyrazin-2-yl)methanol. Additional deprotection and/or functionalization steps can be required to produce the final compound.

A general synthesis of (3-(amino)-6-(phenylthio)pyrazin-2-yl)methanol is outlined in Scheme 2.

Scheme 2. General synthesiso fo(3-(amino)-6-(phenylthio)pyrazin-2-yl)methanol

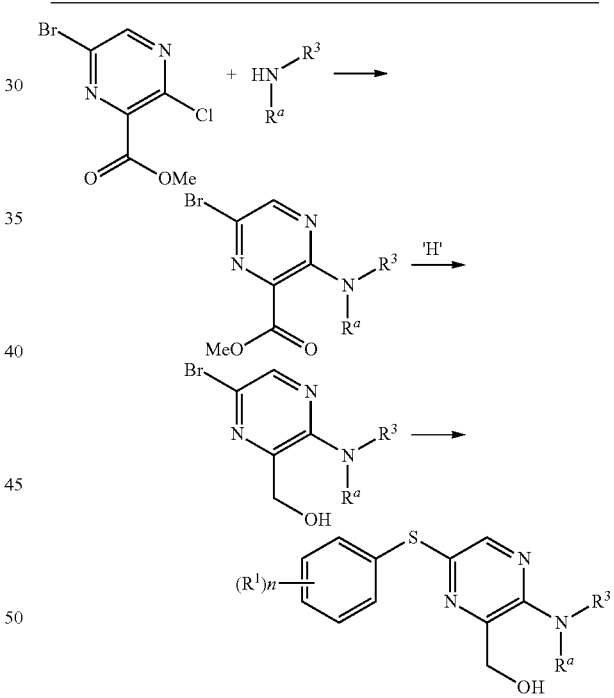

3-Chloro-6-phenylpyrazine-2-carboxylate can be coupled to a primary or secondary amines under SNAr conditions. The resulting aminopyrazine ester can then be reduced to produce amino pyrazin-2-yl-methanol, following coupling to an appropriately substituted potassium (or sodium) salt of arylthiol or heteroarylthiol. Additional deprotection and/or functionalization steps can be required to produce the final compound.

Methods of Using the Disclosed Compounds and Compositions

Methods and Uses of the Disclosure

Another aspect of the disclosure relates to a method of treating a disease associated with SHP2 modulation in a subject in need thereof. The method involves administering to a patient in need of treatment for diseases or disorders associated with SHP2 modulation an effective amount of one or more compounds of the present disclosure (e.g., compounds of Formula Ia, I, IIa, IIb, III, IV, V, or VI, and pharmaceutically acceptable salts, prodrugs, solvates, hydrates, tautomers, or isomers thereof), or of one or more pharmaceutical compositions of the present disclosure. In some embodiments, the disease can be, but is not limited to Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In addition, SHP2 plays a role in transducing signals originating from immune checkpoint molecules, including but not limited to programmed cell death protein 1 (PD-1) and cytotoxic T-lymphocyte-associated protein 4 (CTLA-4). In this context, modulation of SHP2 function can lead to immune activation, specifically anti-cancer immune responses.

Another aspect of the disclosure is directed to a method of inhibiting SHP2. The method involves administering to a patient in need thereof an effective amount of one or more compounds of the present disclosure (e.g., compounds of Formula Ia, I, IIa, IIb, III, IV, V, or VI, and pharmaceutically acceptable salts, prodrugs, solvates, hydrates, tautomers, or isomers thereof), or of one or more pharmaceutical compositions of the present disclosure.

The present disclosure relates to compounds or compositions disclosed herein that are capable of modulating the activity of (e.g., inhibiting) SHP2. The present disclosure also relates to the therapeutic use of such compounds and compositions.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 10 nM to about 100 nM of a compound of the disclosure. In some embodiments, SHP2 is inhibited after treatment with 10 nM to 100 nM of a compound of the disclosure. In some embodiments, SHP2 is inhibited after treatment with less than 10 nM of a compound of the disclosure.

Another aspect of the present disclosure relates to one or more compounds of the present disclosure (e.g., compounds of Formula Ia, I, IIa, IIb, III, IV, V, or VI, and pharmaceutically acceptable salts, co-crystals, prodrugs, solvates, hydrates, tautomers, or isomers thereof), or one or more compositions of the present disclosure for use in treating or preventing a disease associated with SHP2 modulation. In some embodiments, the disease is Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In another aspect, the present disclosure relates to the use of one or more compounds of the present disclosure (e.g., compounds of Formula Ia, I, IIa, IIb, III, IV, V, or VI, and pharmaceutically acceptable salts, co-crystals, prodrugs, solvates, hydrates, tautomers, or isomers thereof), in the manufacture of a medicament for treating or preventing a disease. In some embodiments, the disease is associated with SHP2 modulation.

In another aspect, the present disclosure relates to one or more compounds of the present disclosure (e.g., compounds of Formula Ia, I, IIa, IIb, III, IV, V, or VI, and pharmaceutically acceptable salts, co-crystals, prodrugs, solvates, hydrates, tautomers, or isomers thereof), for use as a medicament. In some embodiments, the medicament is used for treating or preventing a disease associated with SHP2 modulation.

In one aspect, the present disclosure relates to one or more compositions comprising one or more compounds of the present disclosure (e.g., compounds of Formula Ia, I, IIa, IIb, III, IV, V, or VI, and pharmaceutically acceptable salts, prodrugs, solvates, hydrates, tautomers, or isomers thereof), for use as a medicament. In some embodiments, the medicament is used for treating or preventing a disease associated with SHP2 modulation.

Pharmaceutical Compositions and Modes of Administration of the Disclosure

Another aspect of the present disclosure relates to pharmaceutical compositions comprising one or more compounds of the present disclosure and a pharmaceutically acceptable carrier. The pharmaceutically acceptable carriers can further include excipients such as diluent, surfactant, lipid, solvent. In certain embodiments, there are one or more pharmaceutically acceptable carriers or excipients in a pharmaceutical composition.

Compositions can be prepared according to conventional preparation methods of the dosage forms that are applicable for different route of administration, respectively. The present pharmaceutical compositions can contain from about 0.1% to about 99%, from about 5% to about 90%, or from about 1% to about 20% of the disclosed compound by weight or volume.

Administration of the disclosed compounds and pharmaceutical compositions can be accomplished via any mode of administration for therapeutic agents. These modes include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, capsules, tablets, pellets, suppositories, pills, modified-release dosage forms, elixirs, tinctures, emulsions, syrups, powders, liquids, suspensions, patches, or the like, sometimes in unit dosages and consistent with conventional pharmaceutical practices. Likewise, they can also be administered in intravenous (both bolus and infusion), intraperitoneal, subcutaneous or intramuscular, transdermal form, and all using forms well known to those skilled in the pharmaceutical arts.

Illustrative pharmaceutical compositions are liquid and solid dosage forms, such as tablets and capsules, comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200. In certain embodiments, pharmaceutical compositions comprise HPMC. In certain embodiments, pharmaceutical compositions comprise vegetarian (Vegi) type of capsules.

Liquid, particularly injectable, compositions can, for example, be prepared by dissolution, dispersion, lyophilization etc. For example, one or more disclosed compounds are dissolved in or mixed with a pharmaceutically acceptable solvent such as, for example, water, saline, aqueous dextrose, buffer, glycerol, ethanol, cyclodextrin, cremophor EL and the like, to thereby form an injectable isotonic solution or suspension or lyophilized cake for re-constitution. Proteins such as albumin, chylomicron particles, or serum proteins can be used to solubilize the disclosed compounds.

One or more disclosed compounds or compositions can be also formulated as a suppository that can be prepared from fatty emulsions or suspensions; using polyalkylene glycols such as propylene glycol, as the carrier.

One or more disclosed compounds or compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

One or more disclosed compounds or compositions can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxy propylmethacrylamide-phenol, polyhydroxyethyl-aspanamidephenol, or polyethyleneoxide polylysine substituted with palmitoyl residues. Furthermore, the one or more disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In some embodiments, one or more disclosed compounds are not covalently bound to a polymer, e.g., a polycarboxylic acid polymer, or a polyacrylate.

One or more disclosed compounds or compositions can be delivered by parental administration. Parental injectable administration is generally used for subcutaneous, intramuscular or intravenous injections and infusions. Injectables can be prepared in conventional forms, either as liquid solutions or suspensions or solid forms suitable for dissolving or dispersing in liquid prior to injection.

Dosage Regimens of the Disclosure

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In some embodiments, the compositions are in the form of a tablet that can be scored.

If desired, the effective daily dose of one or more compounds or compositions of this disclosure may be administered as one, two, three, four, five, six, or more sub-doses administered separately at appropriate intervals throughout the day, optionally, in unit dosage forms. In some embodiments of this disclosure, the one or more compounds or compositions of this disclosure, or mixtures thereof, may be administered two or three times daily. In some embodiments, the one or more compounds or compositions of this disclosure will be administered once daily.

In some embodiments, one or more compounds or compositions described herein may be used alone or together or conjointly administered, or used in combination, with another type of therapeutic agent. Conjoint administration or used in combination refers to any form of administration of two or more different therapeutic compounds or compositions such that the second compound or composition is administered while the previously administered therapeutic compound or composition is still effective in the body. For example, the different therapeutic compounds or compositions can be administered either in the same formulation or in a separate formulation, either simultaneously, sequentially, or by separate dosing of the individual components of the treatment. In some embodiments, the different therapeutic compounds or compositions can be administered within one hour, 12 hours, 24 hours, 36 hours, 48 hours, 72 hours, or a week of one another. Thus, an individual who receives such treatment can benefit from a combined effect of different therapeutic compounds or compositions.

Kits

In some embodiments, this disclosure also provides a pharmaceutical package or kit comprising one or more containers filled with at least one compound or composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both. In some embodiments, the kit comprises at least two containers, at least one of which contains at least one compound or composition of this disclosure. In some embodiments, the kit contains at least two containers, and each of the at least two containers contains at least one compound or composition of this disclosure.

In some embodiments, the kit includes additional materials to facilitate delivery of the subject compounds and compositions. For example, the kit may include one or more of a catheter, tubing, infusion bag, syringe, and the like. In some embodiments, the compounds and compositions are packaged in a lyophilized form, and the kit includes at least two containers: a container comprising the lyophilized compounds or compositions and a container comprising a suitable amount of water, buffer, or other liquid suitable for reconstituting the lyophilized material.

The foregoing applies to any of the compounds, compositions, methods, and uses described herein. This disclosure specifically contemplates any combination of the features of such compounds, compositions, methods, and uses (alone or in combination) with the features described for the various kits described in this section.

Exemplary Embodiments

Some embodiments of this disclosure are Embodiment I, as follows:

Embodiment I-1

A compound of the Formula I:

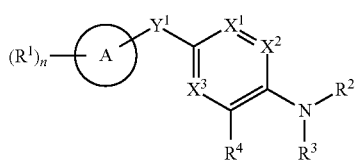

(I)

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —$C(O)OR^5$, —$NH(CH_2)_nOH$, —$C(O)NH(CH_2)_nOH$, —$C(O)NH(CH_2)R$, —C(O)R, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

Embodiment I-2

A compound of the Formula II:

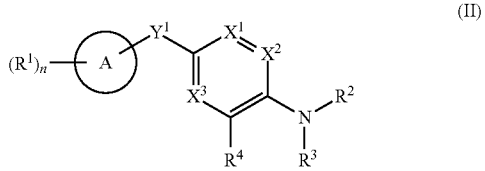

(II)

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;
$Y^1$ is a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —C(O)$OR^5$, —NH(CH$_2)_n$OH, —C(O)NH(CH$_2)_n$OH, —C(O)NH(CH$_2)_n$R, —C(O)R, —$NH_2$, —OH, —CN, —C(O)$NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

Embodiment I-3

A compound of the Formula III:

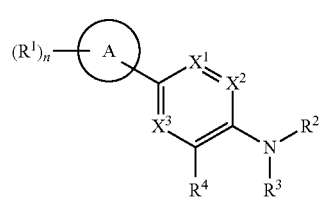

(III)

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is —H, -D, or —$C_1$-$C_6$alkyl, wherein each alkyl is optionally substituted with one or more —OH, —$NH_2$, halogen, or oxo;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_nOH$, —$C_1$-$C_6$alkyl, $CF_3$, $CHF_2$, or $CH_2F$; and n is independently 0, 1, 2, 3, 4, 5, 6, 7, 8, 9, or 10.

Embodiment I-4

The compound of any one of Embodiments I-1 to I-3, wherein $X^1$ is N.

Embodiment I-5

The compound of any one of Embodiments I-1 to I-3, wherein $X^1$ is CH.

Embodiment I-6

The compound of any one of Embodiments I-1 to I-5, wherein $X^2$ is N.

Embodiment I-7

The compound of any one of Embodiments I-1 to I-5, wherein $X^2$ is CH.

Embodiment I-8

The compound of any one of Embodiments I-1 to I-7, wherein $X^3$ is N.

Embodiment I-9

The compound of any one of Embodiments I-1 to I-7, wherein $X^3$ is CH.

Embodiment I-10

The compound of any one of Embodiments I-1 to I-9, wherein A is monocyclic or polycyclic aryl.

Embodiment I-11

The compound of any one of Embodiments I-1 to I-9, wherein A is monocyclic or polycyclic cycloalkyl.

Embodiment I-12

The compound of any one of Embodiments I-1 to I-9, wherein A is monocyclic or polycyclic heterocycloalkyl.

Embodiment I-13

The compound of any one of Embodiments I-1 to I-9, wherein A is monocyclic or polycyclic heteroaryl.

Embodiment I-14

The compound of any one of Embodiments I-1 to I-13, wherein each $R^1$ is selected from the group consisting of —H, halogen, —$C_1$-$C_6$alkyl, and —$NR^5R^6$.

Embodiment I-15

The compound of Embodiment I-14, wherein $R^5$ and $R^6$ are H.

Embodiment I-16

The compound of any one of Embodiments I-1 to I-15, wherein $R^4$ is an optionally substituted —$C_1$-$C_6$alkyl.

Embodiment I-17

The compound of any one of Embodiments I-1 to I-16, wherein $R^4$ is —$CH_2$—OH.

Embodiment I-18

The compound of any one of Embodiments I-1 to I-17, wherein $R^3$ can combine with $R^2$ to form 3- to 12-membered monocyclic or polycyclic heterocycle, wherein the heterocycle is optionally substituted with —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment I-19

The compound of Embodiment I-18, wherein the heterocycle is unsubstituted or substituted with —$C_1$-$C_6$alkyl, —$OR^b$, or —$NH_2$.

Embodiment I-20

The compound of any one of Embodiments I-1 to I-17, wherein $R^3$ can combine with $R^2$ to form a 5- to 12-membered spiroheterocycle, wherein the spiroheterocycle is optionally substituted with —$C_1$-$C_6$alkyl, halogen, —OH, —$OR^b$, —$NH_2$, —$NHR^b$, heteroaryl, heterocyclyl, —$(CH_2)_n$ $NH_2$, —$(CH_2)_n$OH, —$COOR^b$, —$CONHR^b$, —$CONH(CH_2)_n COOR^b$, —$NHCOOR^b$, —$CF_3$, —$CHF_2$, —$CH_2F$, or =O.

Embodiment I-21

The compound of Embodiment I-20, wherein the spirocycle is unsubstituted or substituted with —$C_1$-$C_6$alkyl, —$OR^b$, or —$NH_2$.

Embodiment I-22

A compound, or a pharmaceutically acceptable salt, prodrug, solvate, hydrate, tautomer, or isomer thereof, selected from the group consisting of

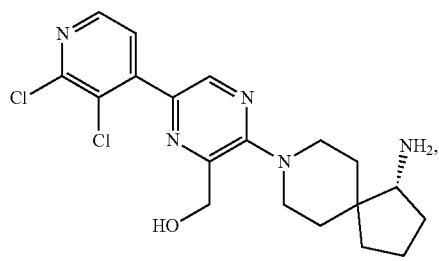
(1)

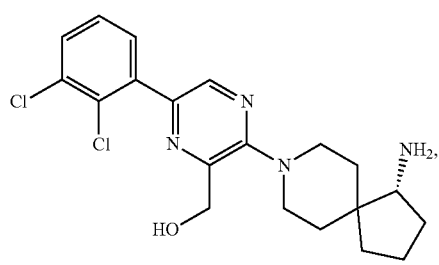
(2)

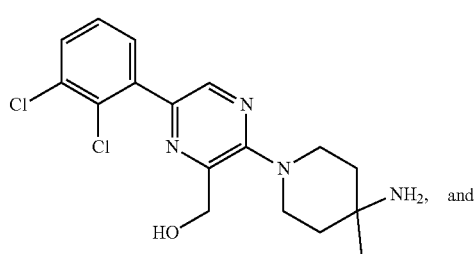
(3) and

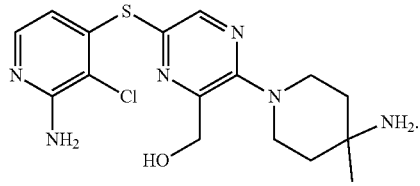
(4)

Embodiment I-23

A pharmaceutical composition comprising a compound of any one of Embodiments I-1 to I-22, or a pharmaceutically acceptable salt, prodrug, solvate, hydrate, tautomer, or isomer thereof, and a pharmaceutically acceptable carrier.

Embodiment I-24

A method of treating a disease associated with SHP2 modulation in a subject in need thereof, comprising administering to the subject an effective amount of a compound of any one of Embodiments I-1 to I-22, or a pharmaceutically acceptable salt, prodrug, solvate, hydrate, tautomer, or isomer thereof.

Embodiment I-25

The method of Embodiment I-24, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-26

A compound of any one of Embodiments I-1 to I-22, or a pharmaceutically acceptable salt, prodrug, solvate, hydrate, tautomer, or isomer thereof, for use as a medicament.

Embodiment I-27

A compound of any one of Embodiments I-1 to I-22, or a pharmaceutically acceptable salt, prodrug, solvate, hydrate, tautomer, or isomer thereof, for use in treating or preventing a disease associated with SHP2 modulation.

Embodiment I-28

Use of a compound of any one of Embodiments I-1 to I-22, or a pharmaceutically acceptable salt, prodrug, solvate, hydrate, tautomer, or isomer thereof, in the manufacture of a medicament for treating or preventing a disease associated with SHP2 modulation.

Embodiment I-29

A method of treating a disease associated with SHP2 modulation in a subject in need thereof, comprising administering to the subject an effective amount of a pharmaceutical composition of Embodiment I-23.

Embodiment I-30

The method of Embodiment I-29, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-31

A pharmaceutical composition of Embodiment I-23 for use as a medicament.

Embodiment I-32

A pharmaceutical composition of Embodiment I-23 for use in treating or preventing a disease associated with SHP2 modulation.

Embodiment I-33

Use of a pharmaceutical composition of Embodiment I-23 in the manufacture of a medicament for treating or preventing a disease associated with SHP2 modulation.

Some embodiments of this disclosure are Embodiment II, as follows:

Embodiment II-1

A compound of the Formula I:

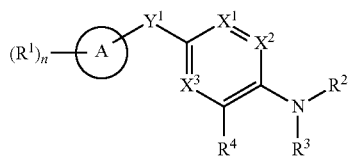

(I)

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)R, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n OH$, —$COOR^b$, —$CONR^b$, —$CONH(CH_2)_n COOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —C(O)$OR^5$, —NH(CH$_2$)$_n$OH, —C(O)NH(CH$_2$)$_n$OH, —C(O)NH(CH$_2$)$_n$R, —C(O)R, —$NH_2$, —OH, —CN, —C(O)$NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)$NR^5R^6$, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

Embodiment II-2

A compound of the Formula IIa:

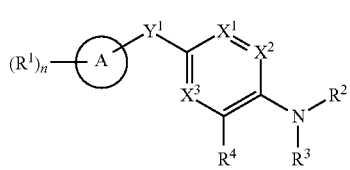

(IIa)

or a pharmaceutically acceptable salt, prodrug, solvate, hydrate, tautomer, or isomer thereof, wherein:

$X^1$ is N or CH;

$X^2$ is N or CH;

$X^3$ is N or CH;

wherein at least one of $X^1$, $X^2$, or $X^3$ is N;

$Y^1$ is a direct bond;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)R, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —$C(O)OR^5$, —$NH(CH_2)_nOH$, —C(O)NH($CH_2)_nOH$, —C(O)NH($CH_2)_nR$, —C(O)R, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

Embodiment II-3

A compound of the Formula IIb:

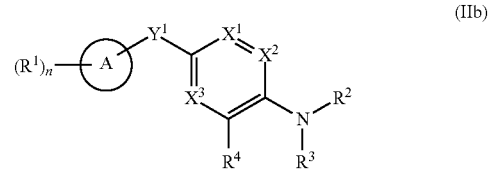

(IIb)

or a pharmaceutically acceptable salt, prodrug, solvate, hydrate, tautomer, or isomer thereof, wherein:

$X^1$ is N or CH;

$X^2$ is N or CH;

$X^3$ is N or CH;

wherein at least one of $X^1$, $X^2$, or $X^3$ is N;

$Y^1$ is —S—;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-

$C_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

$R^4$ is —H, -D, —C$_1$-C$_6$alkyl, —C$_1$-C$_6$haloalkyl, —C$_1$-C$_6$hydroxyalkyl —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R, —C(O)R, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

$R^5$ and $R^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

$R^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

Embodiment II-4

A compound of the Formula III:

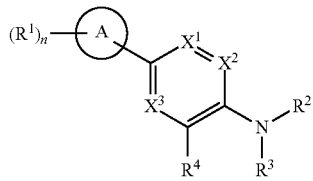

(III)

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, or —NR$^5$C(O)R$^6$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ and $R^3$ are independently selected from the group consisting of —H, -D, —OH, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

$R^4$ is —H, -D, or —C$_1$-C$_6$alkyl, wherein each alkyl is optionally substituted with one or more —OH, —NH$_2$, halogen, or oxo;

$R^5$ and $R^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

$R^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

Embodiment II-5

The compound of any one of Embodiments II-1 to II-4, wherein $X^1$ is N.

Embodiment II-6

The compound of any one of Embodiments II-1 to II-4, wherein $X^1$ is CH.

Embodiment II-7

The compound of any one of Embodiments II-1 to II-6, wherein $X^2$ is N.

Embodiment II-8

The compound of any one of Embodiments II-1 to II-6, wherein $X^2$ is CH.

Embodiment II-9

The compound of any one of Embodiments II-1 to II-8, wherein $X^3$ is N.

Embodiment II-10

The compound of any one of Embodiments II-1 to II-8, wherein $X^3$ is CH.

Embodiment II-11

The compound of any one of Embodiments II-1 to II-10, wherein A is monocyclic or polycyclic aryl.

Embodiment II-12

The compound of any one of Embodiments II-1 to II-10, wherein A is monocyclic or polycyclic cycloalkyl.

Embodiment II-13

The compound of any one of Embodiments II-1 to II-10, wherein A is monocyclic or polycyclic heterocycloalkyl.

Embodiment II-14

The compound of any one of Embodiments II-1 to II-10, wherein A is monocyclic or polycyclic heteroaryl.

Embodiment II-15

The compound of any one of Embodiments II-1 to II-14, wherein each $R^1$ is selected from the group consisting of —H, halogen, —$C_1$-$C_6$alkyl, and —$NR^5R^6$.

Embodiment II-16

The compound of claim 14, wherein $R^5$ and $R^6$ are H.

Embodiment II-17

The compound of any one of Embodiments II-1 to II-16, wherein $R^4$ is an optionally substituted —$C_1$-$C_6$alkyl.

Embodiment II-18

The compound of any one of Embodiments II-1 to II-17, wherein $R^4$ is —$CH_2$—OH.

Embodiment II-19

The compound of any one of Embodiments II-1 to II-18, wherein $R^3$ can combine with $R^2$ to form 3- to 12-membered monocyclic or polycyclic heterocycle, wherein the heterocycle is optionally substituted with —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment II-20

The compound of Embodiment II-19, wherein the heterocycle is unsubstituted or substituted with —$C_1$-$C_6$alkyl, —$OR^b$, or —$NH_2$.

Embodiment II-21

The compound of any one of Embodiments II-1 to II-18, wherein $R^3$ can combine with $R^2$ to form a 5- to 12-membered spiroheterocycle, wherein the spiroheterocycle is optionally substituted with —$C_1$-$C_6$alkyl, halogen, —OH, —$OR^b$, —$NH_2$, —$NHR^b$, heteroaryl, heterocyclyl, —$(CH_2)_n$ $NH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment II-22

The compound of Embodiment II-21, wherein the spirocycle is unsubstituted or substituted with —$C_1$-$C_6$alkyl, —$OR^b$, or —$NH_2$.

Embodiment II-23

A compound, or a pharmaceutically acceptable salt, prodrug, solvate, hydrate, tautomer, or isomer thereof, selected from the group consisting of

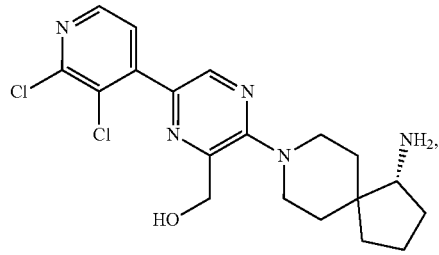

(1)

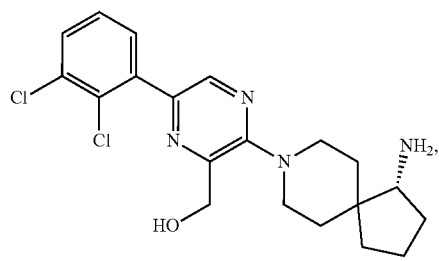

(2)

-continued (3)
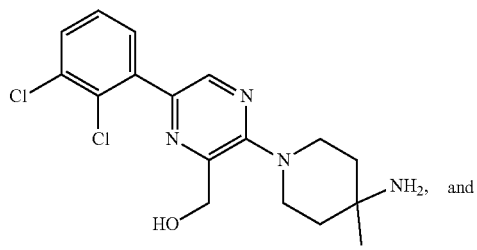

and (4)
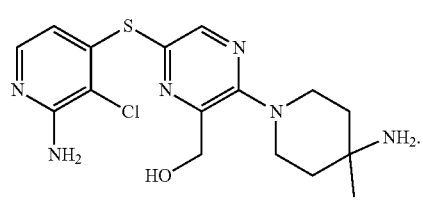

Embodiment II-24

A compound, or a pharmaceutically acceptable salt, prodrug, solvate, hydrate, tautomer, or isomer thereof, selected from the group consisting of

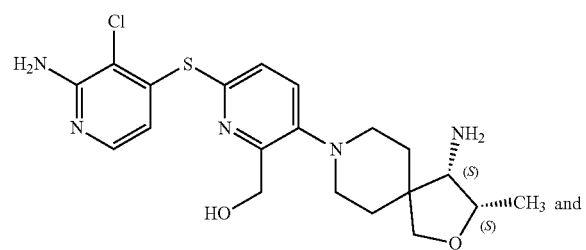

Embodiment II-25

A pharmaceutical composition comprising a compound of any one of Embodiments II-1 to II-24, or a pharmaceutically acceptable salt, prodrug, solvate, hydrate, tautomer, or isomer thereof, and a pharmaceutically acceptable carrier.

Embodiment II-26

A method of treating a disease associated with SHP2 modulation in a subject in need thereof, comprising administering to the subject an effective amount of a compound of any one of Embodiments II-1 to II-24, or a pharmaceutically acceptable salt, prodrug, solvate, hydrate, tautomer, or isomer thereof.

Embodiment II-27

The method of Embodiment II-26, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-28

A compound of any one of Embodiments II-1 to II-24, or a pharmaceutically acceptable salt, prodrug, solvate, hydrate, tautomer, or isomer thereof, for use as a medicament.

Embodiment II-29

A compound of any one of Embodiments II-1 to II-24, or a pharmaceutically acceptable salt, prodrug, solvate, hydrate, tautomer, or isomer thereof, for use in treating or preventing a disease associated with SHP2 modulation.

Embodiment II-30

Use of a compound of any one of Embodiments II-1 to II-24, or a pharmaceutically acceptable salt, prodrug, solvate, hydrate, tautomer, or isomer thereof, in the manufacture of a medicament for treating or preventing a disease associated with SHP2 modulation.

Embodiment II-31

A method of treating a disease associated with SHP2 modulation in a subject in need thereof, comprising administering to the subject an effective amount of a pharmaceutical composition of Embodiment II-25.

Embodiment II-32

The method of Embodiment II-31, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-33

A pharmaceutical composition of Embodiment II-25 for use as a medicament.

Embodiment II-34

A pharmaceutical composition of Embodiment II-25 for use in treating or preventing a disease associated with SHP2 modulation.

Embodiment II-35

Use of a pharmaceutical composition of Embodiment II-25 in the manufacture of a medicament for treating or preventing a disease associated with SHP2 modulation.

Some embodiments of this disclosure are Embodiment III, as follows:

Embodiment III-1

A compound of Formula IV:

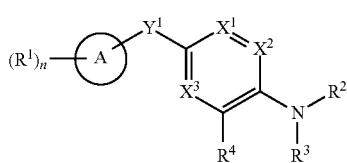

(IV)

or a pharmaceutically acceptable salt, prodrug, solvate, hydrate, tautomer, or isomer thereof, wherein:
$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;
$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)R, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;
$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or
$R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;
$R^4$ is —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —S(O)$_2OH$, —C(O)$OR^5$, —NH(CH$_2)_nOH$, —C(O)NH(CH$_2)_nOH$, —C(O)NH(CH$_2)R$, —C(O)R, —$NH_2$, —OH, —CN, —C(O)$NR^5R^6$, —S(O)$_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;
$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;
$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;
$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$OH, —$C_1$-$C_6$alkyl, $CF_3$, $CHF_2$, or $CH_2F$; and
n is independently 0, 1, 2, 3, 4, 5, 6, 7, 8, 9, or 10.

Embodiment III-2

A compound of the Formula V:

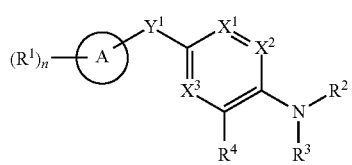

(V)

or a pharmaceutically acceptable salt, prodrug, solvate, hydrate, tautomer, or isomer thereof, wherein:
$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;
$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ and R$^3$ are independently selected from the group consisting of —H, -D, —OH, —C$_1$-C$_6$alkyl, a 3- to 12-membered monocyclic or polycyclic heterocycle, a 5- to 12-membered spiroheterocycle, C$_3$-C$_8$cycloalkyl, —(CH$_2$)$_n$—R$^b$, or —(CH$_2$)$_n$C(O)NR$^5$R$^6$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^2$ to form a 3- to 12-membered monocyclic or polycyclic heterocycle, or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^4$ is -C$_1$-C$_6$alkyl, wherein each alkyl is optionally substituted with one or more —OH, —NH$_2$, halogen, or oxo;

R$^5$ and R$^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

Embodiment III-3

A compound of the Formula VI:

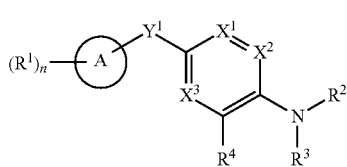

(VI)

or a pharmaceutically acceptable salt, prodrug, solvate, hydrate, tautomer, or isomer thereof, wherein:

X$^1$ is N or CH;
X$^2$ is N or CH;
X$^3$ is N or CH;
wherein at least one of X$^1$, X$^2$, or X$^3$ is N;
Y$^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R, —CO$_2$R$^5$, —C(O)NR$^5$R$^6$, —NR$^5$C(O)R$^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ can combine with R$^2$ to form a 3- to 12-membered monocyclic or polycyclic heterocycle, or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^4$ is -C$_1$-C$_6$alkyl, wherein each alkyl is optionally substituted with one or more —OH, —NH$_2$, halogen, or oxo;

R$^5$ and R$^6$ are each independently, at each occurrence, selected from the group consisting of —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, and —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^b$ is independently —H, -D, —C$_1$-C$_6$alkyl, —C$_1$-C$_6$cycloalkyl, —C$_2$-C$_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —C$_1$-C$_6$alkyl, CF$_3$, CHF$_2$, or CH$_2$F; and n is independently 0, 1, 2, 3, 4, 5, 6, 7, 8, 9, or 10.

Embodiment III-4

A compound of the Formula I:

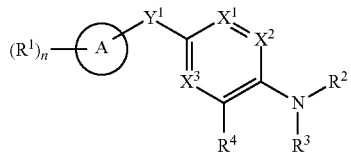

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;
$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;
$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or
$R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;
$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)R, —$NHC(O)NHR^5$, —$NHS(O)_2R^5$, —$NHS(O)_2NHR^5$, —$S(O)_2OH$, —$C(O)OR^5$, —$NH(CH_2)_nOH$, —C(O)NH$(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;
$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;
$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; $R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_nOH$, —$C_1$-$C_6$alkyl, $CF_3$, $CHF_2$, or $CH_2F$; and
n is independently 0, 1, 2, 3, 4, 5, 6, 7, 8, 9, or 10.

Embodiment III-5

The compound of any one of Embodiment III-1 to III-4, wherein $X^1$ is N.

Embodiment III-6

The compound of any one of of Embodiment III-1 to III-4, wherein $X^1$ is CH.

Embodiment III-7

The compound of any one of of Embodiment III-1 to III-6, wherein $X^2$ is N.

Embodiment III-8

The compound of any one of of Embodiment III-1 to III-6, wherein $X^2$ is CH.

Embodiment III-9

The compound of any one of of Embodiment III-1 to III-8, wherein $X^3$ is N.

Embodiment III-10

The compound of any one of of Embodiment III-1 to III-8, wherein $X^3$ is CH.

Embodiment III-11

The compound of any one of Embodiment III-1 to III-10, wherein A is monocyclic or polycyclic aryl.

Embodiment III-12

The compound of any one of Embodiment III-1 to III-10, wherein A is monocyclic or polycyclic cycloalkyl.

Embodiment III-13

The compound of any one of Embodiment III-1 to III-10, wherein A is monocyclic or polycyclic heterocycloalkyl.

Embodiment III-14

The compound of any one of Embodiment III-1 to III-10, wherein A is monocyclic or polycyclic heteroaryl.

Embodiment III-15

The compound of any one of Embodiment III-1 to III-14, wherein each $R^1$ is selected from the group consisting of —H, halogen, —$C_1$-$C_6$alkyl, and —$NR^5R^6$.

Embodiment III-16

The compound of Embodiment III-14, wherein $R^5$ and $R^6$ are H.

Embodiment III-17

The compound of any one of Embodiment III-1 to III-16, wherein $R^4$ is an optionally substituted —$C_1$-$C_6$alkyl.

Embodiment III-18

The compound of any one of Embodiment III-1 to III-17, wherein $R^4$ is —$CH_2$—OH.

Embodiment III-19

The compound of any one of Embodiment III-1 to III-18, wherein $R^3$ can combine with $R^2$ to form 3- to 12-membered monocyclic or polycyclic heterocycle, wherein the heterocycle is optionally substituted with —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment III-20

The compound of Embodiment III-19, wherein the heterocycle is unsubstituted or substituted with —$C_1$-$C_6$alkyl, —$OR^b$, or —$NH_2$.

Embodiment III-21

The compound of any one of Embodiment III-1 to III-18, wherein $R^3$ can combine with $R^2$ to form a 5- to 12-membered spiroheterocycle, wherein the spiroheterocycle is optionally substituted with —$C_1$-$C_6$alkyl, halogen, —OH, —$OR^b$, —$NH_2$—$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment III-22

The compound of Embodiment III-21, wherein the spirocycle is unsubstituted or substituted with —$C_1$-$C_6$alkyl, —$OR^b$, or —$NH_2$.

Embodiment III-23

The compound of any one of Embodiment III-1 to III-18, wherein $R^3$ combine with $R^2$ to form a moiety selected from:

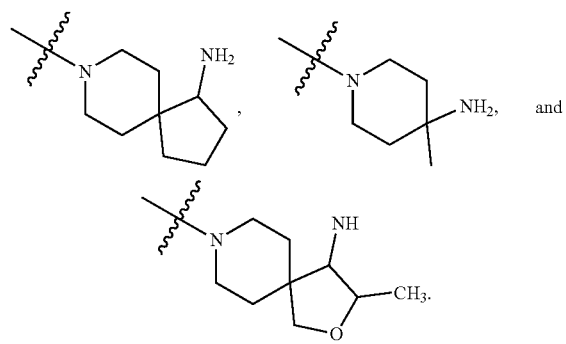

Embodiment III-24

A compound, or a pharmaceutically acceptable salt, prodrug, solvate, hydrate, tautomer, or isomer thereof, selected from the group consisting of

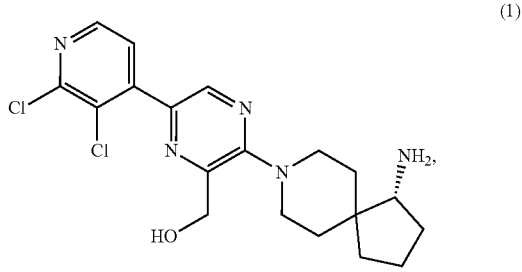

(1)

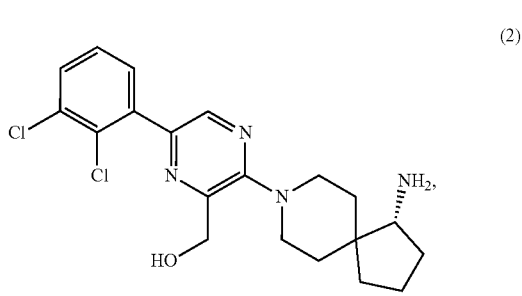

(2)

85
-continued
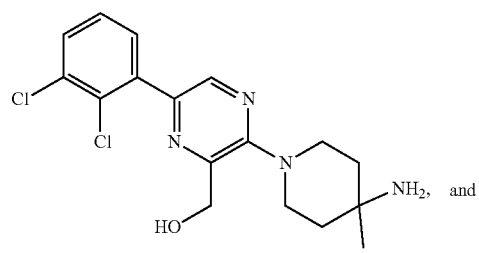
(3)
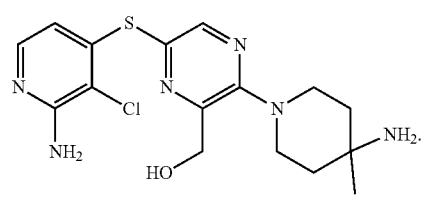
(4)
Embodiment III-25
A compound, or a pharmaceutically acceptable salt, prodrug, solvate, hydrate, tautomer, or isomer thereof, selected from the group consisting of
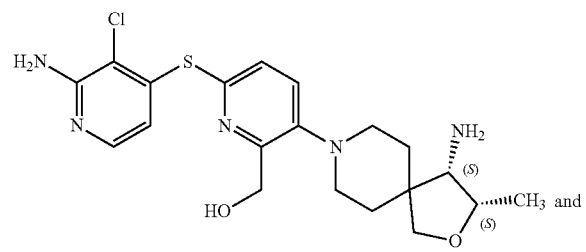
(5)
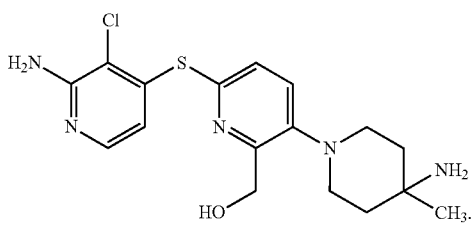
(5a)
Embodiment III-26
A compound, or a pharmaceutically acceptable salt, prodrug, solvate, hydrate, tautomer, or isomer thereof, selected from the group consisting of
86
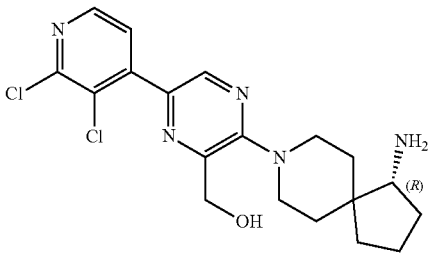
(1)
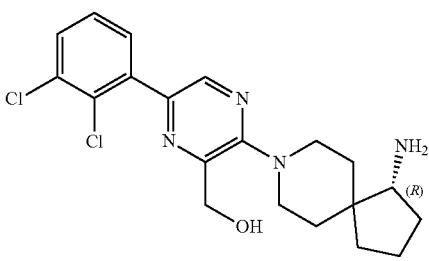
(2)
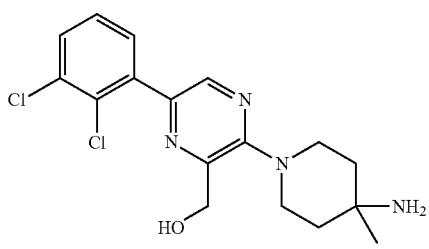
(3)
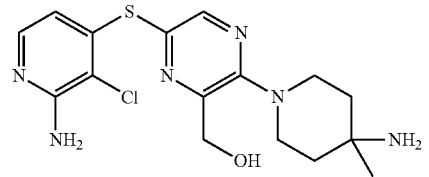
(4)
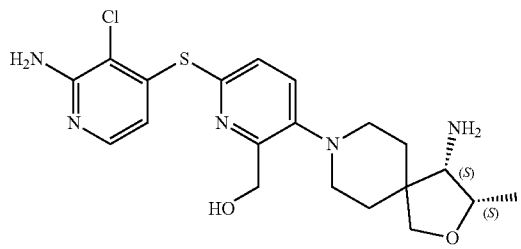
(5)
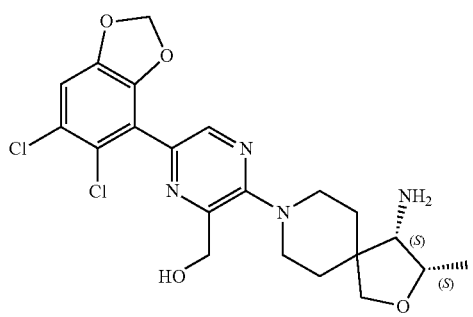
(6)

-continued
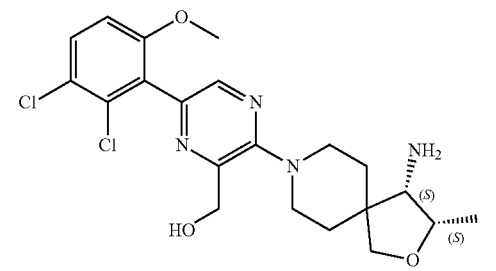
(7)
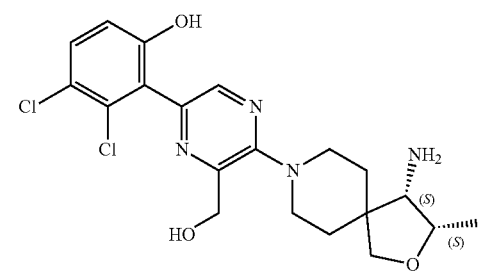
(8)
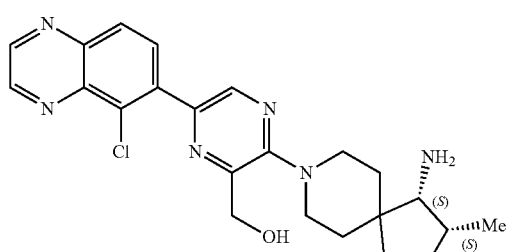
(9)
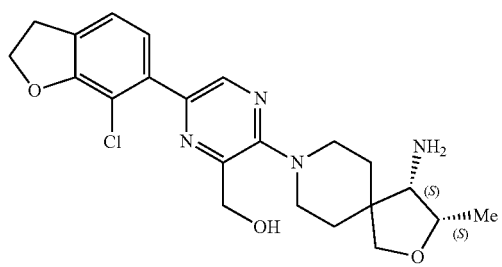
(10)
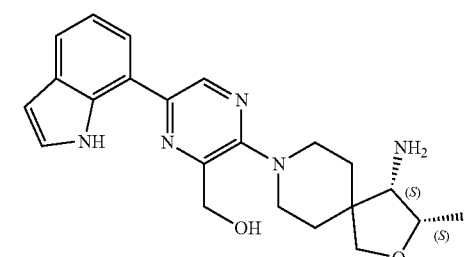
(11)
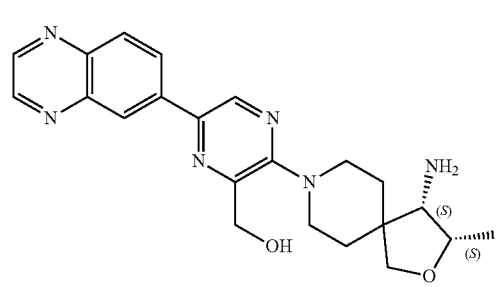
(12)
-continued
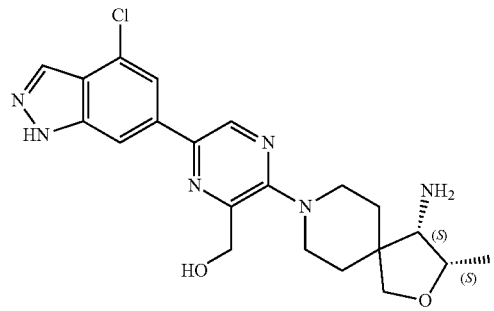
(13)
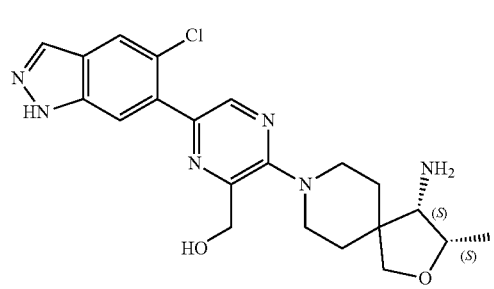
(14)
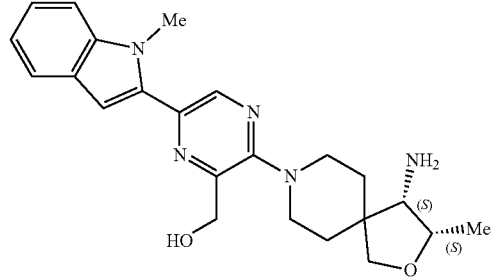
(15)
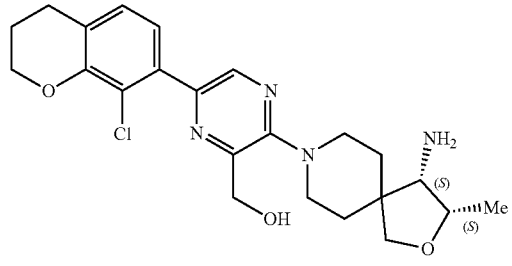
(16)
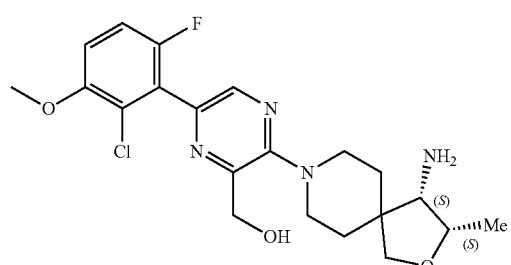
(17)

-continued
(18)
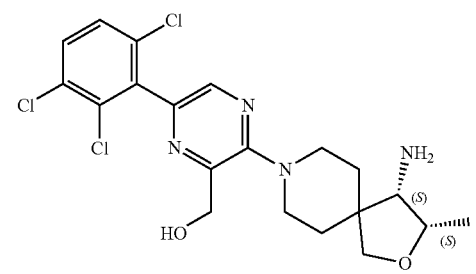
(19)
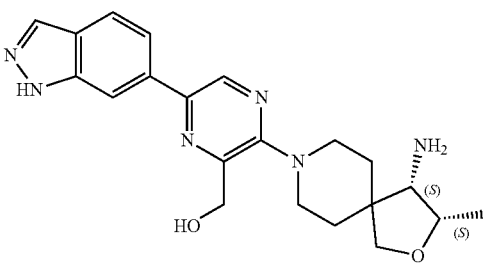
(20)
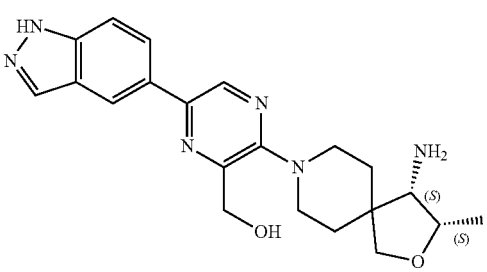
(21)
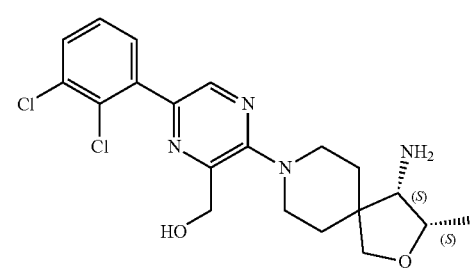
(22)
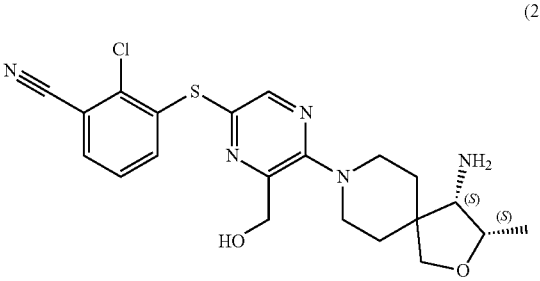
(23)
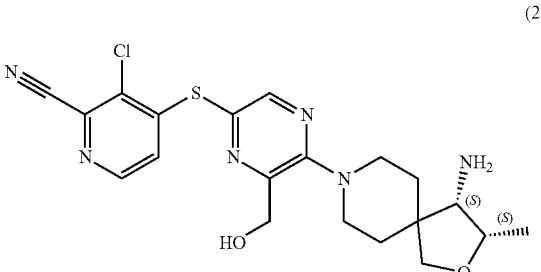
-continued
(24)
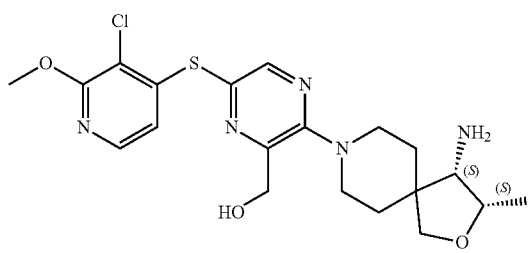
(25)
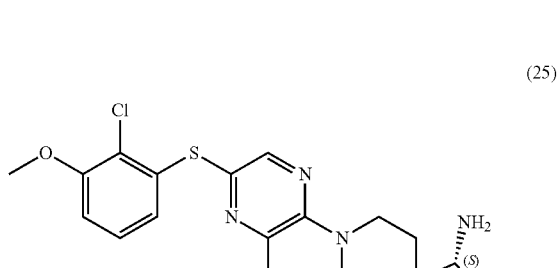
(26)
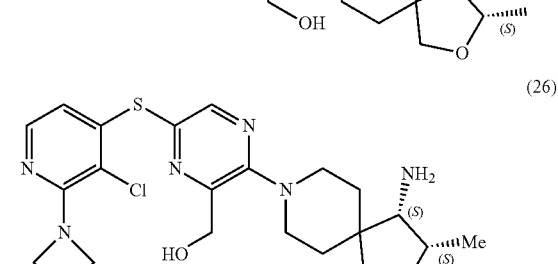
(27)
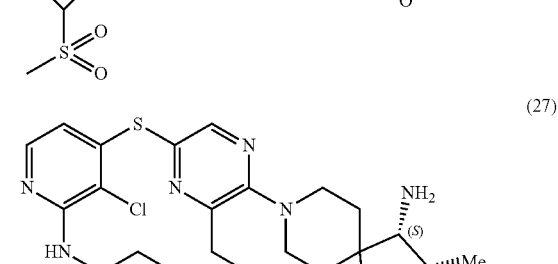
(28)
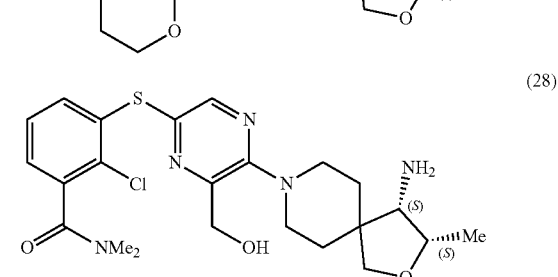
(29)
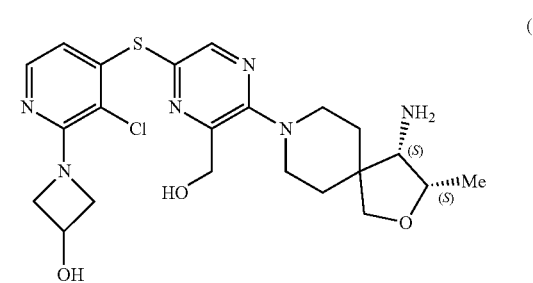

-continued

(30)
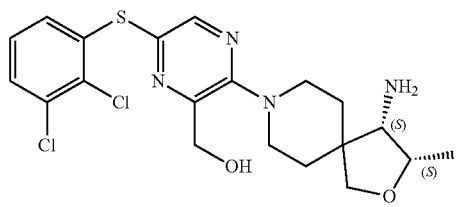

(31)
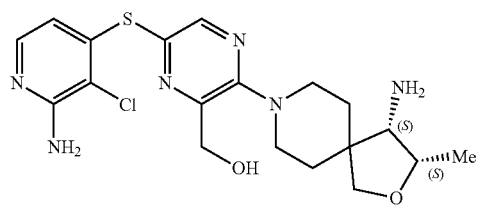

(32)
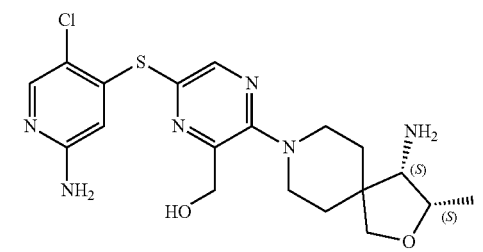

(33)
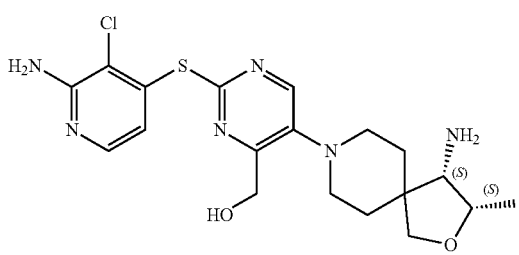

Embodiment III-27

A pharmaceutical composition comprising a compound of any one of Embodiment III-1 to III-26, or a pharmaceutically acceptable salt, prodrug, solvate, hydrate, tautomer, or isomer thereof, and a pharmaceutically acceptable carrier.

Embodiment III-28

A method of treating a disease associated with SHP2 modulation in a subject in need thereof, comprising administering to the subject an effective amount of a compound of any one of Embodiment III-1 to III-26, or a pharmaceutically acceptable salt, prodrug, solvate, hydrate, tautomer, or isomer thereof.

Embodiment III-29

The method of Embodiment III-28, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment III-30

A compound of any one of Embodiment III-1 to III-26, or a pharmaceutically acceptable salt, prodrug, solvate, hydrate, tautomer, or isomer thereof, for use as a medicament.

Embodiment III-31

A compound of any one of Embodiment III-1 to III-26, or a pharmaceutically acceptable salt, prodrug, solvate, hydrate, tautomer, or isomer thereof, for use in treating or preventing a disease associated with SHP2 modulation.

Embodiment III-32

Use of a compound of any one of Embodiment III-1 to III-26, or a pharmaceutically acceptable salt, prodrug, solvate, hydrate, tautomer, or isomer thereof, in the manufacture of a medicament for treating or preventing a disease associated with SHP2 modulation.

Embodiment III-33

A method of treating a disease associated with SHP2 modulation in a subject in need thereof, comprising administering to the subject an effective amount of a pharmaceutical composition of Embodiment III-27.

Embodiment III-34

The method of Embodiment III-31, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment III-35

A pharmaceutical composition of Embodiment III-27 for use as a medicament.

Embodiment III-36

A pharmaceutical composition of Embodiment III-27 for use in treating or preventing a disease associated with SHP2 modulation.

Embodiment III-37

Use of a pharmaceutical composition of Embodiment III-27 in the manufacture of a medicament for treating or preventing a disease associated with SHP2 modulation.

Some embodiments of this disclosure are Embodiment IV, as follows:

Embodiment IV-1

A compound of Formula IV:

(IV)
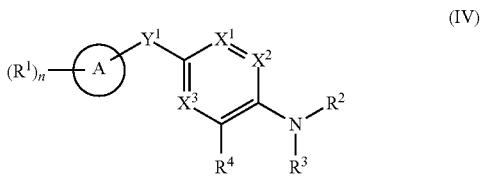

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond, A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —(CH$_2$)$_n$—R$^b$, or —(CH$_2$)$_n$C(O)NR$^5$R$^6$, wherein each alkyl, heterocycle, or cycloalkyl is optionally substituted with one or more —$C_1$-$C_6$alkyl, —OH, —NH$_2$, —OR$^b$, —NHR$^b$, —(CH$_2$)$_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

$R^4$ is —$C_1$-$C_6$alkyl, —$C_1$-$C_6$haloalkyl, —$C_1$-$C_6$hydroxyalkyl —CF$_2$OH, —CHFOH, —NH—NHR$^5$, —NH—OR$^5$, —O—NR$^5$R$^6$, —NHR$^5$, —OR$^5$, —NHC(O)R, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —OR$^7$, —SR$^7$, halogen, —NR$^7$R$^8$, —NO$_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

$R^b$ is independently —H, -D, —$C_1$-$C_6$alkyl, —$C_1$-$C_6$cycloalkyl, —$C_2$-$C_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$—, —NR$^5$R$^6$C(O)—, heterocycle, aryl, heteroaryl, —(CH$_2$)$_n$ OH, —$C_1$-$C_6$alkyl, CF$_3$, CHF$_2$, or CH$_2$F; and n is independently 0, 1, 2, 3, 4, 5, 6, 7, 8, 9, or 10.

Embodiment IV-2

A compound of the Formula V:

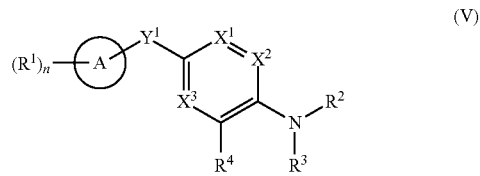

(V)

or a pharmaceutically acceptable salt, prodrug, solvate, hydrate, tautomer, or isomer thereof, wherein:

$X^1$ is N or CH;
$X^2$ is N or CH;
$X^3$ is N or CH;
wherein at least one of $X^1$, $X^2$, or $X^3$ is N;
$Y^1$ is —S— or a direct bond, A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, —(CH$_2$)$_n$—R$^b$, or —(CH$_2$)$_n$C(O)NR$^5$R$^6$, wherein each alkyl, heterocycle, or cycloalkyl is optionally substituted with one or more —$C_1$-$C_6$alkyl, —OH, —NH$_2$, —OR$^b$, —NHR$^b$, —(CH$_2$)$_n$OH, heterocyclyl, or spiroheterocyclyl; or R³ can combine with R² to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R⁴ is-$C_1$-$C_6$alkyl, wherein each alkyl is optionally substituted with one or more —OH, —NH$_2$, halogen, or oxo;

R⁵ and R⁶ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —OR⁷, —SR⁷, halogen, —NR⁷R⁸, —NO$_2$, and —CN;

R⁷ and R⁸ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^b$ is independently —H, -D, —$C_1$-$C_6$alkyl, —$C_1$-$C_6$cycloalkyl, —$C_2$-$C_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R⁵, —OR⁵, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH$_2$)$_n$ OH, —$C_1$-$C_6$alkyl, CF$_3$, CHF$_2$, or CH$_2$F; and n is independently 0, 1, 2, 3, 4, 5, 6, 7, 8, 9, or 10.

Embodiment IV-3

A compound of the Formula VI:

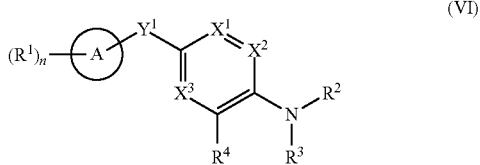

(VI)

or a pharmaceutically acceptable salt, prodrug, solvate, hydrate, tautomer, or isomer thereof, wherein:

X¹ is N or CH;
X² is N or CH;
X³ is N or CH;
wherein at least one of X¹, X², or X³ is N;
Y¹ is —S— or a direct bond,
A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

R¹ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —OR⁶, halogen, —NO$_2$, —CN, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, —C(O)R⁵, —CO$_2$R⁵, —C(O)NR⁵R⁶, —NR⁵C(O)R⁶, or 3- to 12-membered monocyclic or polycyclic heterocycle, wherein each alkyl, alkenyl, cycloalkenyl, alkynyl, cycloalkyl or heterocycle is optionally substituted with one or more —OH, halogen, —NO$_2$, oxo, —CN, —R⁵, —OR⁵, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, heterocycle, aryl, or heteroaryl;

R³ can combine with R² to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR⁵R⁶, —CF$_3$, —CHF$_2$, —CH$_2$F, or =O; wherein the heteroaryl and heterocyclyl are optionally substituted with —CN;

R⁴ is-$C_1$-$C_6$alkyl, wherein each alkyl is optionally substituted with one or more —OH, —NH$_2$, halogen, or oxo;

R⁵ and R⁶ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —OR⁷, —SR⁷, halogen, —NR⁷R⁸, —NO$_2$, and —CN;

R⁷ and R⁸ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

R$^b$ is independently —H, -D, —$C_1$-$C_6$alkyl, —$C_1$-$C_6$cycloalkyl, —$C_2$-$C_6$alkenyl, —(CH$_2$)$_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R⁵, —OR⁵, —NR⁵R⁶, —SR⁵, —S(O)$_2$NR⁵R⁶, —S(O)$_2$R⁵, —NR⁵S(O)$_2$NR⁵R⁶, —NR⁵S(O)$_2$R⁶, —S(O)NR⁵R⁶, —S(O)R⁵, —NR⁵S(O)NR⁵R⁶, —NR⁵S(O)R⁶, —C(O)NR⁵R⁶—, —NR⁵R⁶C(O)—, heterocycle, aryl, heteroaryl, —(CH$_2$)$_n$ OH, —$C_1$-$C_6$alkyl, CF$_3$, CHF$_2$, or CH$_2$F; and n is independently 0, 1, 2, 3, 4, 5, 6, 7, 8, 9, or 10.

Embodiment IV-4

A compound of the Formula I:

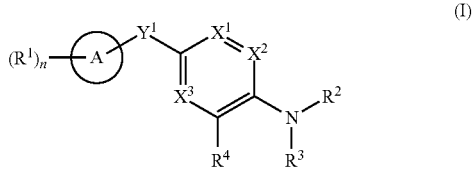

(I)

or a pharmaceutically acceptable salt, prodrug, solvate, hydrate, tautomer, or isomer thereof, wherein:

$X^1$ is N or CH;

$X^2$ is N or CH;

$X^3$ is N or CH;

wherein at least one of $X^1$, $X^2$, or $X^3$ is N;

$Y^1$ is —S— or a direct bond,

A is selected from the group consisting of 5- to 12-membered monocyclic or polycyclic cycloalkyl, monocyclic or polycyclic heterocycloalkyl, monocyclic or polycyclic aryl, or monocyclic or polycyclic heteroaryl;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, or —$NR^5C(O)R^6$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ and $R^3$ are independently selected from the group consisting of —H, -D, —OH, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^2$ to form a 3- to 12-membered monocyclic or polycyclic heterocycle, or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is —H, -D, —$C_1$-$C_6$alkyl, —$C_1$-$C_6$haloalkyl, —$C_1$-$C_6$hydroxyalkyl —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —$C(O)OR^5$, —NH(CH$_2$)$_n$OH, —C(O)NH(CH$_2$)$_n$OH, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are each independently, at each occurrence, selected from the group consisting of —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, and —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

$R^b$ is independently —H, -D, —$C_1$-$C_6$alkyl, —$C_1$-$C_6$cycloalkyl, —$C_2$-$C_6$alkenyl, —$(CH_2)_n$-aryl, heterocyclyl containing 1-5 heteroatoms selected from the group consisting of N, S, P, or O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$—, —$NR^5R^6C(O)$—, heterocycle, aryl, heteroaryl, —$(CH_2)_n$ OH, —$C_1$-$C_6$alkyl, $CF_3$, $CHF_2$, or $CH_2F$; and n is independently 0, 1, 2, 3, 4, 5, 6, 7, 8, 9, or 10.

Embodiment IV-5

The compound of any one of Embodiments IV-1 to IV-4, wherein $X^1$ is N.

Embodiment IV-6

The compound of any one of Embodiments IV-1 to IV-4, wherein $X^1$ is CH.

Embodiment IV-7

The compound of any one of Embodiments IV-1 to IV-6, wherein $X^2$ is N.

Embodiment IV-8

The compound of any one of Embodiments IV-1 to IV-6, wherein $X^2$ is CH.

Embodiment IV-9

The compound of any one of Embodiments IV-1 to IV-8, wherein $X^3$ is N.

Embodiment IV-10

The compound of any one of Embodiments IV-1 to IV-8, wherein $X^3$ is CH.

Embodiment IV-11

The compound of anyone of Embodiments IV-1 to IV-10, wherein A is monocyclic or polycyclic aryl.

Embodiment IV-12

The compound of any one of Embodiments IV-1 to IV-10, wherein A is monocyclic or polycyclic cycloalkyl.

Embodiment IV-13

The compound of any one of Embodiments IV-1 to IV-10, wherein A is monocyclic or polycyclic heterocycloalkyl.

Embodiment IV-14

The compound of any one of Embodiments IV-1 to IV-10, wherein A is monocyclic or polycyclic heteroaryl.

Embodiment IV-15

The compound of any one of Embodiments IV-1 to IV-14, wherein each $R^1$ is selected from the group consisting of —H, halogen, —$C_1$-$C_6$alkyl, and —$NR^5R^6$.

Embodiment IV-16

The compound of Embodiment IV-15, wherein $R^5$ and $R^6$ are H.

Embodiment IV-17

The compound of any one of Embodiments IV-1 to IV-16, wherein $R^4$ is an optionally substituted —$C_1$-$C_6$alkyl.

Embodiment IV-18

The compound of any one of Embodiment IV-1 to IV-17, wherein $R^4$ is -$CH_2$—OH.

Embodiment IV-19

The compound of any one of Embodiments IV-1 to IV-17, wherein $R^4$ is —$C_1$-$C_6$alkyl substituted with one or more halogen.

Embodiment IV-20

The compound of any one of Embodiment IV-1 to IV-19, wherein $R^3$ can combine with $R^2$ to form 3- to 12-membered monocyclic or polycyclic heterocycle, wherein the heterocycle is optionally substituted with —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment IV-21

The compound of Embodiment IV-20, wherein the heterocycle is unsubstituted or substituted with —$C_1$-$C_6$alkyl, —$OR^b$, or —$NH_2$.

Embodiment IV-22

The compound of any one of Embodiment IV-1 to IV-19, wherein $R^3$ can combine with $R^2$ to form a 5- to 12-membered spiroheterocycle, wherein the spiroheterocycle is optionally substituted with —$C_1$-$C_6$alkyl, halogen, —OH, —$OR^b$, —$NH_2$, —$NHR^b$, heteroaryl, heterocyclyl, —$(CH_2)_n$ $NH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O.

Embodiment IV-23

The compound of Embodiment IV-22, wherein the spirocycle is unsubstituted or substituted with —$C_1$-$C_6$alkyl, —$OR^b$, or —$NH_2$.

Embodiment IV-24

The compound of any one of Embodiment IV-1 to IV-19, wherein $R^3$ combine with $R^2$ to form a moiety selected from:

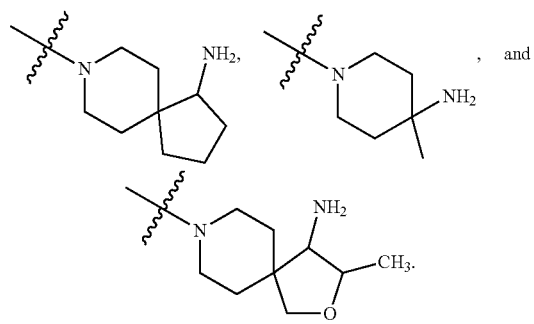

Embodiment IV-25

A compound, or a pharmaceutically acceptable salt, prodrug, solvate, hydrate, tautomer, or isomer thereof, selected from the group consisting of (1)

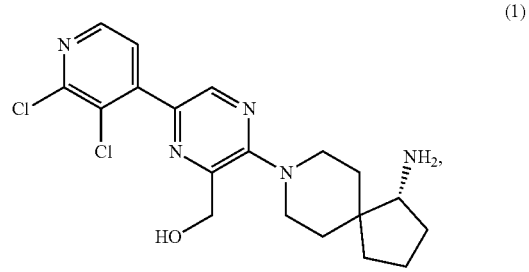

(2)

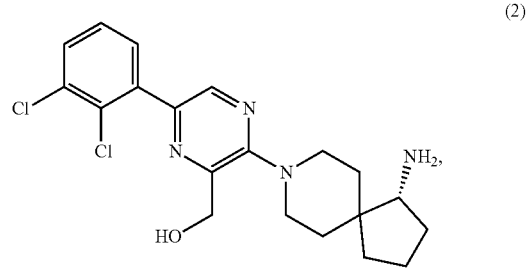

(3)

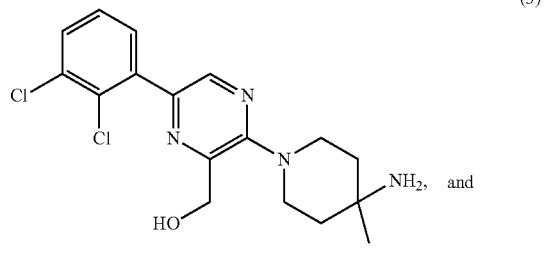

(4)

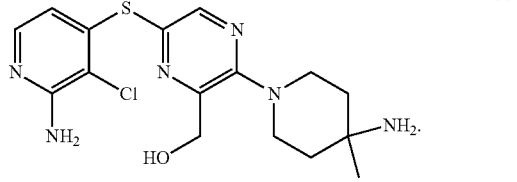

Embodiment IV-26

A compound, or a pharmaceutically acceptable salt, prodrug, solvate, hydrate, tautomer, or isomer thereof, selected from the group consisting of

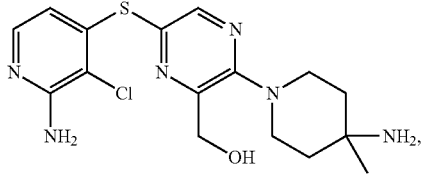
(4)
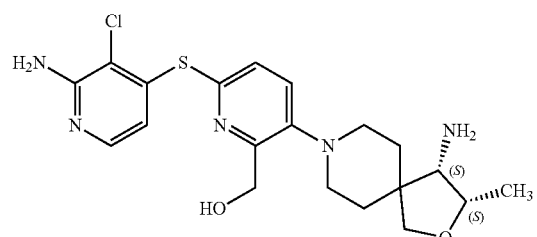
(5)
and
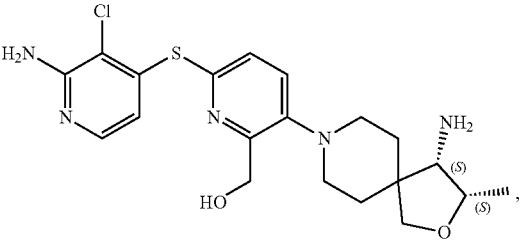
(5a)
Embodiment IV-27
A compound, or a pharmaceutically acceptable salt, prodrug, solvate, hydrate, tautomer, or isomer thereof, selected from the group consisting of
(1)
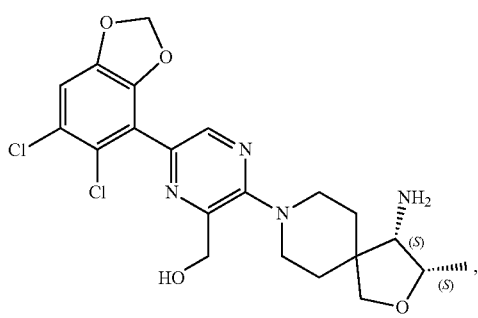
(5)
(6)
(2)
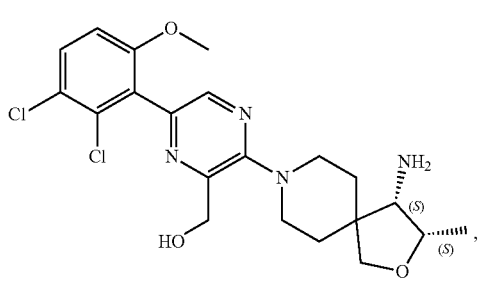
(7)
(3)
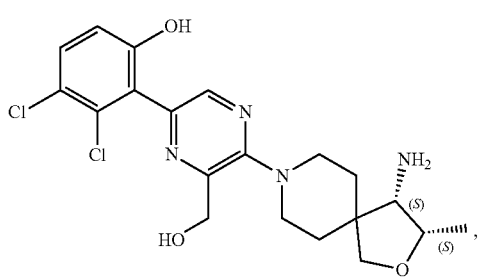
(8)
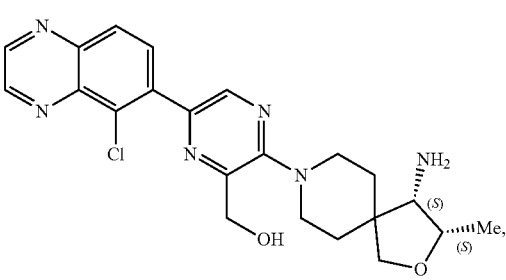
(9)

(10)
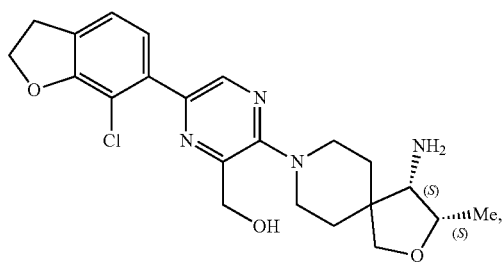
(11)
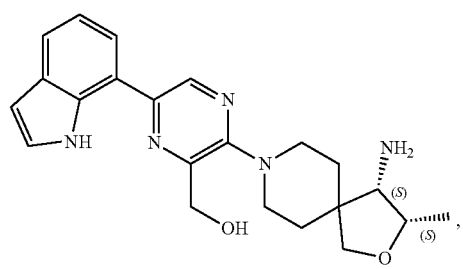
(12)
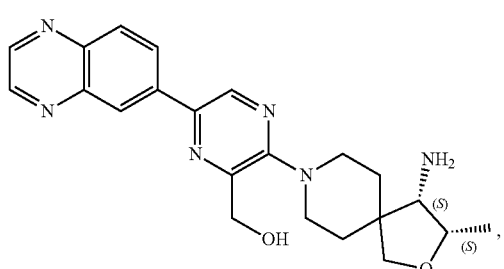
(13)
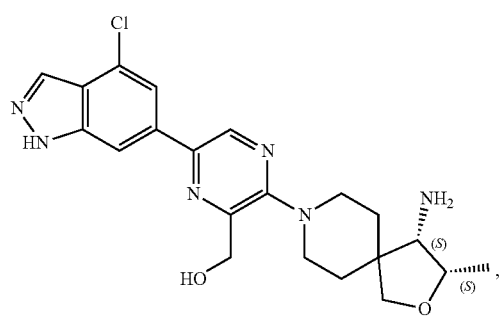
(14)
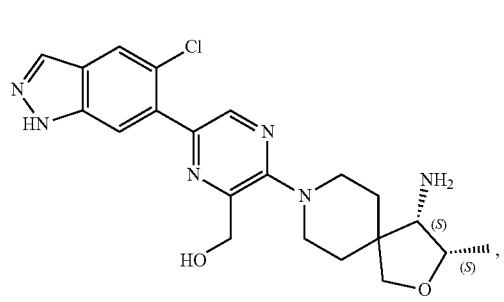
(15)
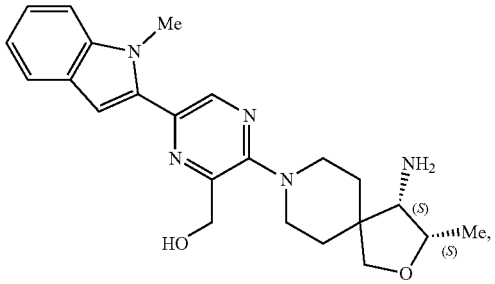
(16)
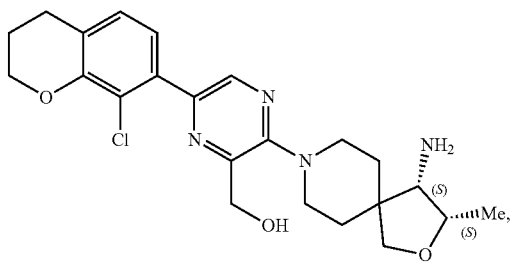
(17)
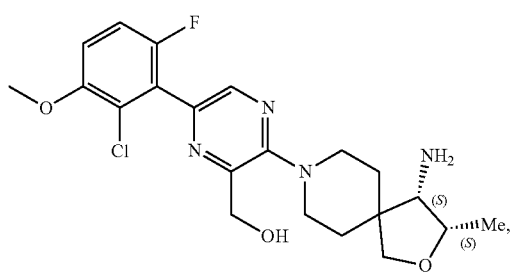
(18)
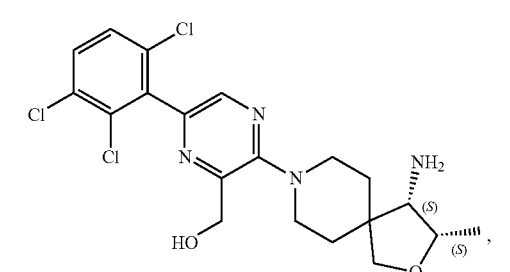
(19)
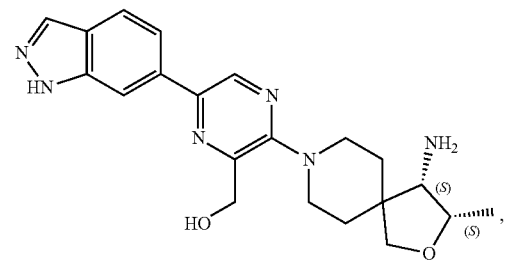

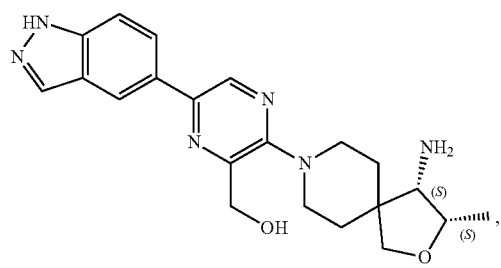
(20)
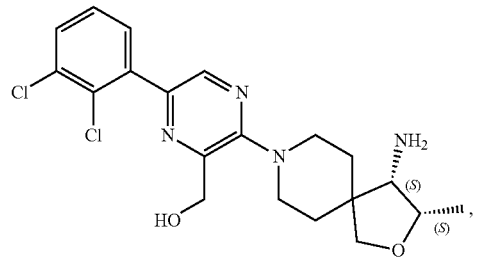
(21)
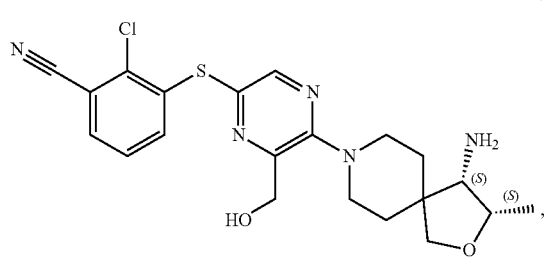
(22)
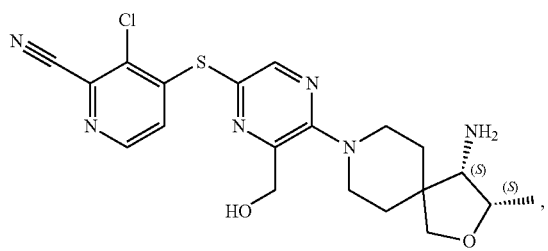
(23)
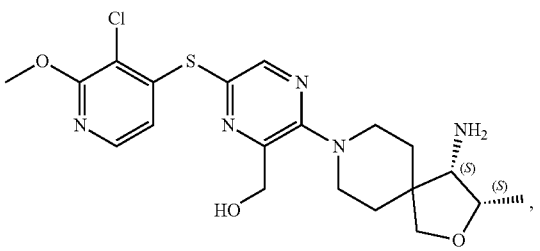
(24)
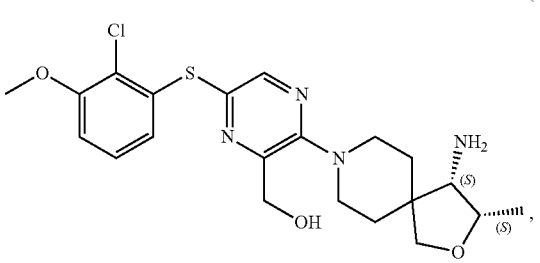
(25)
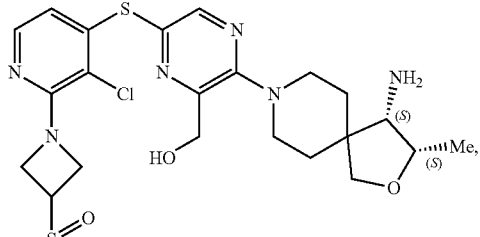
(26)
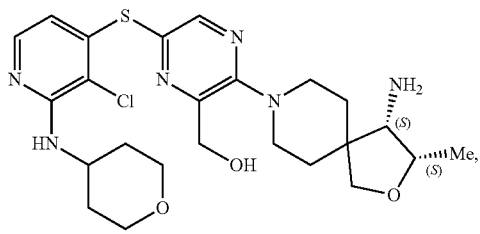
(27)
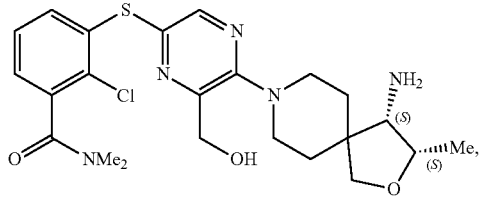
(28)
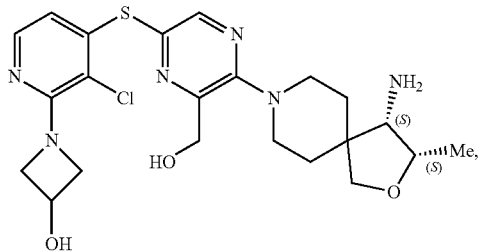
(29)
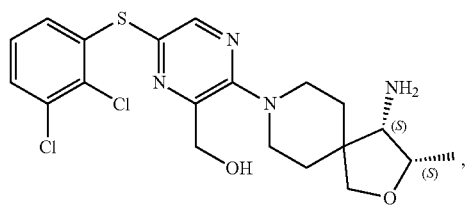
(30)
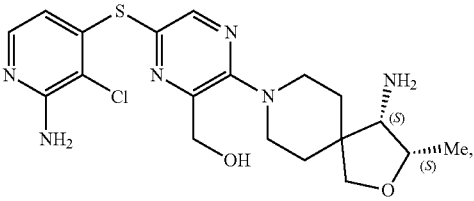
(31)

-continued (32)

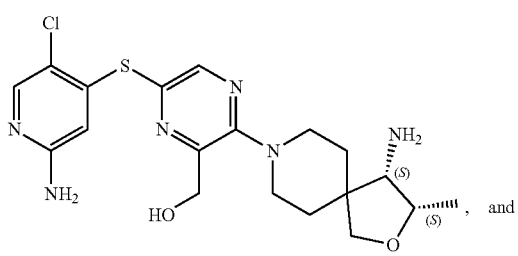

(33)

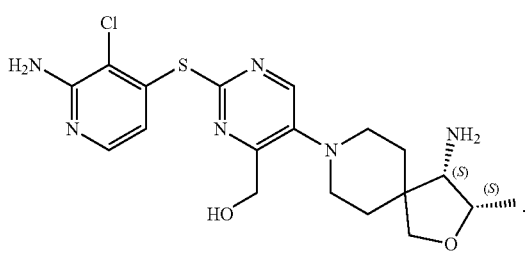

Embodiment IV-28

A compound, or a pharmaceutically acceptable salt, prodrug, solvate, hydrate, tautomer, or isomer thereof, selected from the group consisting of (34)

(35)

Embodiment IV-29

A pharmaceutical composition comprising a compound of any one of Embodiments IV-1 to IV-28, or a pharmaceutically acceptable salt, prodrug, solvate, hydrate, tautomer, or isomer thereof, and a pharmaceutically acceptable carrier.

Embodiment IV-30

A method of treating a disease associated with SHP2 modulation in a subject in need thereof, comprising administering to the subject an effective amount of a compound of any one of Embodiment IV-1 to IV-28, or a pharmaceutically acceptable salt, prodrug, solvate, hydrate, tautomer, or isomer thereof.

Embodiment IV-31

The method of Embodiment IV-30, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment IV-32

A compound of any one of Embodiment IV-1 to IV-28, or a pharmaceutically acceptable salt, prodrug, solvate, hydrate, tautomer, or isomer thereof, for use as a medicament.

Embodiment IV-33

A compound of any one of Embodiments IV-1 to IV-28, or a pharmaceutically acceptable salt, prodrug, solvate, hydrate, tautomer, or isomer thereof, for use in treating or preventing a disease associated with SHP2 modulation.

Embodiment IV-34

Use of a compound of any one of Embodiments IV-1 to IV-28, or a pharmaceutically acceptable salt, prodrug, solvate, hydrate, tautomer, or isomer thereof, in the manufacture of a medicament for treating or preventing a disease associated with SHP2 modulation.

Embodiment IV-35

A method of treating a disease associated with SHP2 modulation in a subject in need thereof, comprising administering to the subject an effective amount of a pharmaceutical composition of Embodiment IV-29.

Embodiment IV-36

The method of Embodiment IV-35, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment IV-37

A pharmaceutical composition of Embodiment IV-29 for use as a medicament.

Embodiment IV-38

A pharmaceutical composition of Embodiment IV-29 for use in treating or preventing a disease associated with SHP2 modulation.

Embodiment IV-39

Use of a pharmaceutical composition of Embodiment IV-29 in the manufacture of a medicament for treating or preventing a disease associated with SHP2 modulation.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:
$CH_2Cl_2$, DCM Methylene chloride, Dichloromethane
$CH_3CN$, MeCN Acetonitrile
CuI Copper (I) iodide
DIPEA Diisopropylethyl amine
DMF N,N-Dimethylformamide
EtOAc Ethyl acetate
Hr hour
$H_2O$ Water
HCl Hydrochloric acid
$K_3PO_4$ Potassium phosphate (tribasic)
MeOH Methanol
$Na_2SO_4$ Sodium sulfate
NMP N-methyl pyrrolidone
Pd(dppf)$Cl_2$ [1,1'-Bis(diphenylphosphino)ferrocene]dichloropalladium(II)

Example 1—Synthesis of (3-[(1R)-1-amino-8-azaspiro[4.5]decan-8-yl]-6-(2,3-dichloropyridin-4-yl)pyrazin-2-yl)methanol (Compound 1)

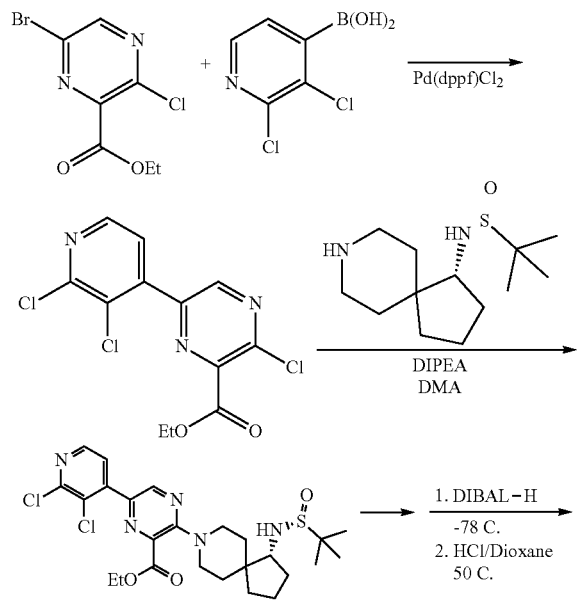

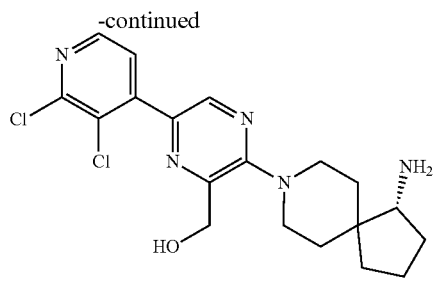

Step-1: Synthesis of 3-chloro-6-(2,3-dichloropyridin-4-yl)pyrazine-2-ethylcarboxylate A mixture of 6-bromo-3-chloropyrazine-2-ethylcarboxylate (1 g, 3.97 mmol), (2,3-dichloropyridin-4-yl)boronic acid (0.93 g, 4.76 mmol), and potassium carbonate (2.18 g, 15.8 mmol) in 40 mL of acetonitrile was degassed, and Pd(dppf)$Cl_2CH_2Cl_2$ (648 mg, 0.79 mmol) was added. The resulting mixture was allowed to stir under an inert atmosphere at 95° C. for 1 h. Concentration under reduced pressure, and purification by column chromatography (40% EtOAc/60% Heptane) resulted in 3-chloro-6-(2,3-dichloropyridin-4-yl)pyrazine-2-ethylcarboxylate (350 mg, 27% yield).

Step-2: Synthesis of 6-(2,3-dichloropyridin-4-yl)-3-((R)-1-((R)-1,1-dimethylethylsulfinamido)-8-azaspiro[4.5]decan-8-yl)pyrazine-2-ethylcarboxylate To a solution of 3-chloro-6-(2,3-dichloropyridin-4-yl)pyrazine-2-ethylcarboxylate (350 mg, 1.35 mmol) and (R)-2-methyl-N—((R)-8-azaspiro[4.5]decan-1-yl)propane-2-sulfinamide (450 mg, 1.4 mmol) in DMA (2.5 mL) under an inert atmosphere was added DIPEA (233 uL, 1.4 mmol). The resulting mixture was allowed to stir at 50° C. for 30 min. Ethyl acetate (20 mL) was added to the reaction mixture, and the resulting slurry was washed with water (20 mL), brine (10 mL), and dried over anhydrous magnesium sulfate. Filtration, and concentration under reduced pressure resulted in 6-(2,3-dichloropyridin-4-yl)-3-((R)-1-((R)-1,1-dimethylethylsulfinamido)-8-azaspiro[4.5]decan-8-yl)pyrazine-2-ethylcarboxylate (150 mg). The product was submitted to the next step without further purification.

Step-3: Synthesis of (3-[(1R)-1-amino-8-azaspiro[4.5]decan-8-yl]-6-(2,3-dichloropyridin-4-yl)pyrazin-2-yl)methanol To a solution of 6-(2,3-dichloropyridin-4-yl)-3-((R)-1-((R)-1,1-dimethylethylsulfinamido)-8-azaspiro[4.5]decan-8-yl)pyrazine-2-ethylcarboxylate (150 mg, 0.28 mmol) in DCM (3 mL) at −78° C. was added dropwise 1M solution of DIBAL-H in DCM (1.1 mL, 1.1 mmol). The resulting mixture was allowed to stir at −78° C. for 30 min, then warmed up to 0° C. and allowed to stir for an additional 5 min. The reaction mixture was subsequently cooled down to −78° C., followed by addition of saturated Rochelle's salt solution (6 mL). The resulting slurry was allowed to warm up to RT under vigorous stirring for a period of 1 h, followed by addition of DCM (20 mL) and water (15 mL). Layers were separated and the aqueous phase was extracted with DCM (20 mL). The combined organic layers were dried over anhydrous magnesium sulfate. Filtration and concentration under reduced pressure resulted in the yellow oil. The resulting sample was dissolved in MeOH (2 mL), and HCl/MeOH (4 M, 0.5 mL) was added. The resulting mixture was stirred at 50° C. for 1 hr, and concentrated under reduced pressure. Purification by preparative HPLC chromatography, followed by liophilisation resulted in (R)-(3-(1-amino-8-azaspiro[4.5]decan-8-yl)-6-(2,3-dichloropyridin-4-yl)pyrazin-2-yl)methanol (11 mg, 9.7% yield) as a white solid. $^1$H NMR (500 MHz, Methanol-d4) δ 8.62 (s, 1H), 8.56 (s, 1H), 8.40 (d, J=5.0 Hz, 1H), 7.76 (d, J=5.0 Hz, 1H), 4.75 (s, 2H), 3.95-3.88 (m, 1H), 3.88-3.80 (m, 1H), 3.30-3.15 (m, 3H), 2.30-2.20 (m, 1H), 1.99-1.71 (m, 5H), 1.66-1.54 (m, 2H). LC-MS (ESI): m/z [M+H] $C_{19}H_{25}Cl_2N_5O$ calculated 408.13; found 408.30.

Example 2—Synthesis of (3-[(1R)-1-amino-8-azaspiro[4.5]decan-8-yl]-6-(2,3-dichlorophenyl)pyrazin-2-yl)methanol (Compound 2)

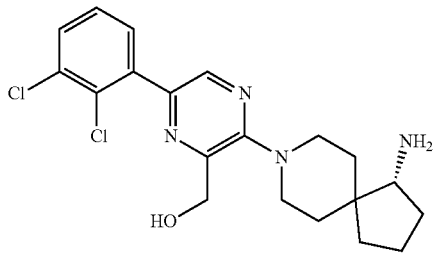 [SMILES: N[C@@H]1CCCC12CCN(c1ncc(-c3cccc(Cl)c3Cl)nc1CO)CC2]

(3-[(1R)-1-amino-8-azaspiro[4.5]decan-8-yl]-6-(2,3-dichlorophenyl)pyrazin-2-yl)methanol was synthesized in the manner similar to Example 1, except (2,3-dichloropyridin-4-yl)boronic acid was substituted with (2,3-dichlorophenyl)boronic acid. $^1$H NMR (500 MHz, Methanol-d4) δ 8.57 (s, 1H), 8.44 (d, J=0.5 Hz, 1H), 7.64 (dd, J=8.0, 1.6 Hz, 1H), 7.61 (dd, J=7.8, 1.6 Hz, 1H), 7.44 (t, J=7.9 Hz, 1H), 4.75 (d, J=0.5 Hz, 2H), 3.74 (dd, J=26.9, 13.3 Hz, 2H), 3.22-3.11 (m, 3H), 2.27-2.14 (m, 1H), 2.01-1.75 (m, 6H), 1.74-1.63 (m, 1H), 1.56 (dd, J=20.9, 13.0 Hz, 2H). LC-MS (ESI): m/z [M+H] $C_{20}H_{25}Cl_2N_4O$ calculated 407.13; found 407.31.

Example 3—Synthesis of [3-(4-amino-4-methylpiperidin-1-yl)-6-(2,3-dichlorophenyl)pyrazin-2-yl]methanol (Compound 3)

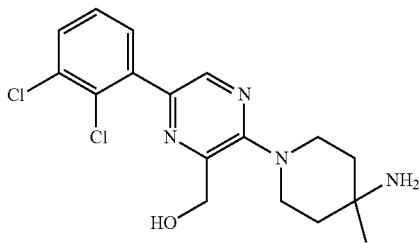 [SMILES: CC1(N)CCN(c2ncc(-c3cccc(Cl)c3Cl)nc2CO)CC1]

[3-(4-amino-4-methylpiperidin-1-yl)-6-(2,3-dichlorophenyl)pyrazin-2-yl]methanol can be synthesized in the manner similar to Example 1, except (R)-2-methyl-N—((R)-8-azaspiro[4.5]decan-1-yl)propane-2-sulfinamide was substituted with tert-butyl N-(4-methylpiperidin-4-yl)carbamate. $^1$H NMR (500 MHz, Methanol-d4) δ 8.55 (s, 1H) 8.45 (s, 1H) 7.60 (ddd, J=14.36, 8.00, 1.75 Hz, 2H) 7.39-7.46 (m, 1H) 4.73 (s, 2H) 3.72 (dt, J=14.03, 4.17 Hz, 2H) 3.32-3.39 (m, 2H) 1.96-2.06 (m, 2H) 1.86-1.95 (m, 2H) 1.50 (s, 3H). LC-MS (ESI): m/z [M+H] $C_{17}H_{21}Cl_2N_4O$ calculated 367.1; found 366.9.

Example 4—Synthesis of (6-((2-amino-3-chloropyridin-4-yl)thio)-3-(4-amino-4-methylpiperidin-1-yl)pyrazin-2-yl)methanol (Compound 4)

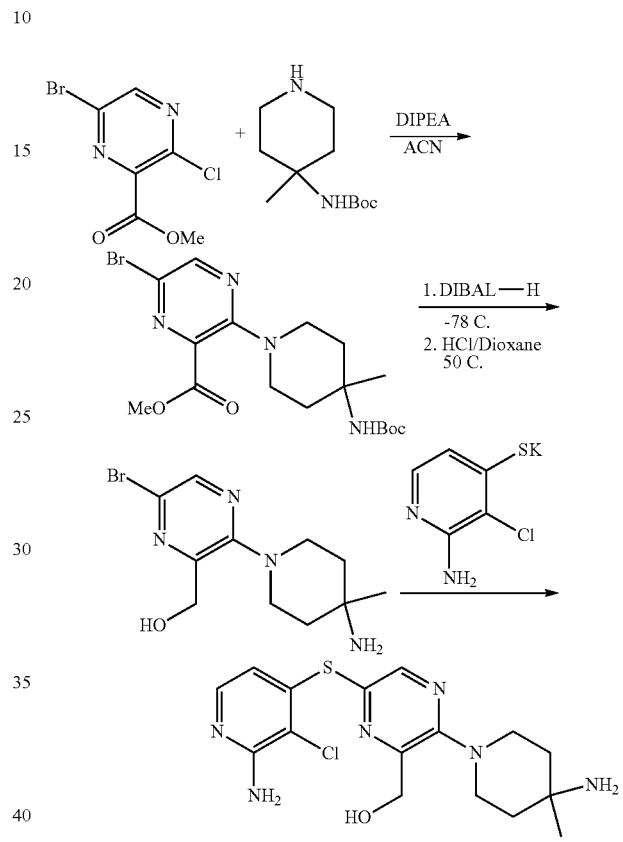

Step-1: Synthesis of methyl 6-bromo-3-(4-((tert-butoxycarbonyl)amino)-4-methylpiperidin-1-yl)pyrazine-2-carboxylate A mixture of 6-bromo-3-chloropyrazine-2-methylcarboxylate (2 g, 7.95 mmol), tert-butyl N-(4-methylpiperidin-4-yl)carbamate (1.87 g, 8.74 mmol), N,N-Diisopropylethylamine (6.57 mL, 39.7 mmol), and 40 mL of acetonitrile was allowed to stir in a sealed tube at 35° C. for 2 hrs, followed by concentration under reduced pressure. The residue was extracted with EtOAc/water, dried over magnesium sulfate, and concentrated under reduced pressure. The resulting product was submitted to the next step without further purification. $^1$H NMR (500 MHz, Methanol-d4) δ 8.27 (s, 1H), 3.95 (s, 3H), 3.68-3.59 (m, 2H), 3.32-3.27 (m, 2H), 2.14 (d, J=13.9 Hz, 2H), 1.59 (ddd, J=14.1, 10.8, 4.1 Hz, 2H), 1.46 (s, 12H), 1.35 (s, 3H). LC-MS (ESI): m/z [M+H] $C_{17}H_{26}BrN_4O_4$ calculated 429.12, found 429.3.

Step-2: Synthesis of (3-(4-amino-4-methylpiperidin-1-yl)-6-bromopyrazin-2-yl)methanol Methyl 6-bromo-3-(4-((tert-butoxycarbonyl)amino)-4-methylpiperidin-1-yl)pyrazine-2-carboxylate (3.5 g, 8.15 mmol) was dissolved in DCM (81.5 mL). The resulting yellow solution was cooled to −78° C. and DIBAL-H (4.63 g, 32.6 mmol) was added dropwise, and the resulting mixture was allowed to stir for 1 hr at −78° C., warmed up to 0° C. for 30 minutes, and cooled back to −78° C., followed by addition of saturated aqueous Rochelle's salt solution (800 mL) at −78° C. To the resulting slurry was added 400 ml of DCM and the reaction was allowed to warm to RT while stirring vigorously. To the resulting slurry was allowed to stir for 18 h at RT, and the aqueous phase was extracted with DCM (2×400 mL). The combined organic extracts were dried over magnesium sulfate and concentrated under reduced pressure. The residue was dissolved in 20 mL of MeOH, and 2.0 ml of 4N HCl/dioxane was added. The resulting mixture was allowed to stir at 50° C. for 18 h. Purification by preparative HPLC chromatography, followed by liophilisation resulted in (3-(4-amino-4-methylpiperidin-1-yl)-6-bromopyrazin-2-yl)methanol. $^1$H NMR (500 MHz, Methanol-d4) δ 8.55 (s, 1H), 8.29-8.25 (m, 1H), 4.64 (d, J=0.5 Hz, 2H), 3.62 (dt, J=14.0, 4.1 Hz, 2H), 3.27 (ddd, J=13.5, 10.1, 3.2 Hz, 3H), 1.98 (ddd, J=13.8, 10.0, 4.1 Hz, 2H), 1.93-1.85 (m, 2H), 1.49 (s, 3H). LC-MS (ESI): m/z [M+H] $C_{11}H_{17}BrN_4O$ calculated 301.06, found 301.2.

Step-3: Synthesis of (6-((2-amino-3-chloropyridin-4-yl)thio)-3-(4-amino-4-methylpiperidin-1-yl)pyrazin-2-yl)methanol A solution of (3-(4-amino-4-methylpiperidin-1-yl)-6-bromopyrazin-2-yl)methanol (50 mg, 0.1660 mmol), 3-chloro-4-(potassiosulfanyl)pyridin-2-amine (49.4 mg, 0.2490 mmol), Pd$_2$dba$_3$ (15.2 mg, 0.01660 mmol), and Xantphos (19.2 mg, 0.03320 mmol) in dioxane (1.66 mL) was degassed, and N,N-Diisopropylethylamine (57.8 uL, 0.332 mmol) was added. The resulting mixture was heated to 120° C. under a microwave conditions for 2 h, allowed to cool to RT, filtered over celite, and concentrated under reduced pressure. Purification by preparative HPLC followed by liophilization resulted in 7.60 mg (6-((2-amino-3-chloropyridin-4-yl)thio)-3-(4-amino-4-methylpiperidin-1-yl)pyrazin-2-yl)methanol (12.0% Yield). $^1$H NMR (400 MHz, Methanol-d4) δ 8.43 (s, 2H), 8.32 (s, 1H), 7.62 (dd, J=5.6, 0.7 Hz, 1H), 6.07 (dd, J=5.6, 0.7 Hz, 1H), 4.68 (s, 2H), 3.83 (dt, J=14.2, 4.5 Hz, 2H), 3.37 (ddd, J=13.7, 10.2, 3.2 Hz, 2H), 1.98 (ddd, J=14.0, 10.1, 4.1 Hz, 2H), 1.90 (dt, J=13.4, 3.9 Hz, 2H), 1.50 (s, 3H). LC-MS (ESI): m/z [M+H] $C_{16}H_{21}ClN_6OS$ calculated 381.1, found 381.3.

Example 5. Synthesis of [6-[(2-amino-3-chloro-4-pyridyl)sulfanyl]-3-[(3S,4S)-4-amino-3-methyl-2-oxa-8-azaspiro[4.5]decan-8-yl]-2-pyridyl]methanol. (Compound 5)

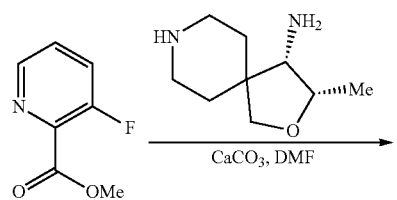

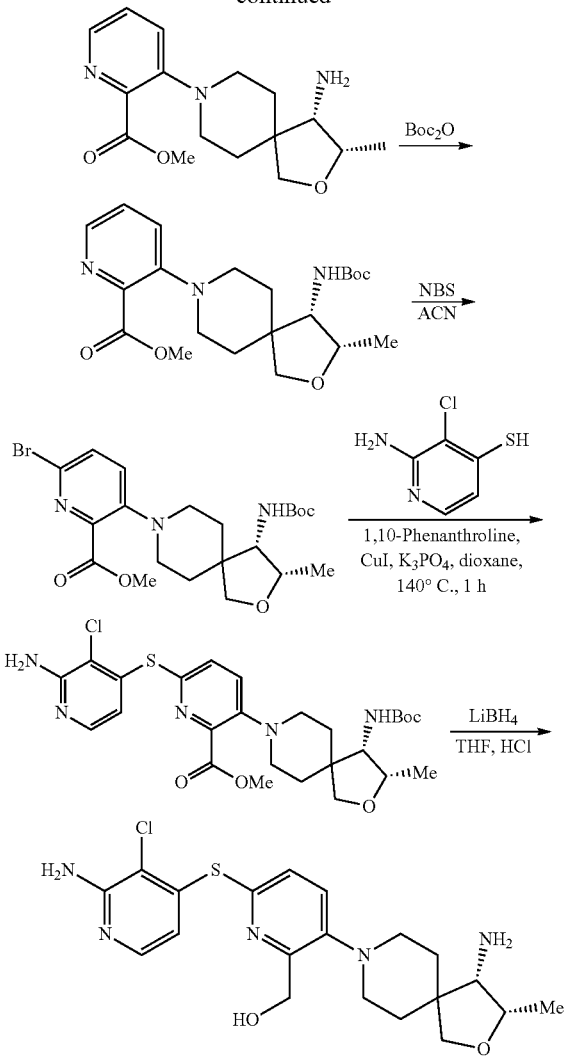

Step 1

To a solution of methyl 3-fluoropyridine-2-carboxylate (319 mg, 2.06 mmol) and (3S,4S)-3-methyl-2-oxa-8-azaspiro[4.5]decan-4-amine (454 mg, 1.87 mmol, 2HCl salt) in DMF (3.8 mL) was added Cs$_2$CO$_3$ (1.83 g, 5.61 mmol). The mixture was stirred at 100° C. for 4 hrs. The reaction mixture was quenched by addition H$_2$O (3 mL) at 25° C. and the resulting mixture was extracted with EtOAc. The combined organic layers were washed with brine, dried over anhydrous Na$_2$SO$_4$, filtered and concentrated under reduced pressure to afford methyl 3-[(3S,4S)-4-amino-3-methyl-2-oxa-8-azaspiro[4.5]decan-8-yl]pyridine-2-carboxylate (2 g, crude) as a white oil. LCMS (ESI): m/z [M+H] calculated for $C_{16}H_{24}N_3O_3$: 306.2; found 306.3.

Step 2

To a solution of methyl 3-[(3S,4S)-4-amino-3-methyl-2-oxa-8-azaspiro[4.5]decan-8-yl]pyridine-2-carboxylate (2 g, 6.55 mmol) in THF (20 mL) was added Boc$_2$O (4.3 g, 19.65 mmol, 4.5 mL). The reaction mixture was stirred at 25° C. for 12 hrs. The reaction mixture was quenched by the addition of H$_2$O (3 mL) at 25° C. The reaction mixture was extracted with EtOAc. The combined organic layers were washed with brine, dried over Na$_2$SO$_4$, filtered and concentrated under reduced pressure. The remaining residue was purified by column chromatography to afford methyl 3-[(3S,4S)-4-(tert-butoxycarbonylamino)-3-methyl-2-oxa-8-azaspiro[4.5]decan-8-yl]pyridine-2-carboxylate (300 mg, 11% yield) as a white solid. $^1$H NMR (400 MHz, Chloroform-d) δ ppm 8.27 (d, J=3.7 Hz, 1H), 7.44-7.38 (m, 1H), 7.36-7.30 (m, 1H), 5.31 (s, 2H), 4.59 (d, J=10.8 Hz, 1H), 4.18 (d, J=4.6 Hz, 1H), 4.02 (d, J=4.4 Hz, 1H), 3.99 (s, 1H), 3.98 (s, 2H), 3.73-3.62 (m, 2H), 3.26-2.84 (m, 5H), 1.99-1.77 (m, 3H), 1.71 (d, J=4.4 Hz, 1H), 1.51 (s, 1H), 1.46 (s, 6H), 1.24-1.18 (m, 3H). LCMS (ESI): m/z: [M+H] calculated for C$_{21}$H$_{32}$N$_3$O$_5$: 406.2; found 406.3.

Step 3

To a solution of methyl 3-[(3S,4S)-4-(tert-butoxycarbonylamino)-3-methyl-2-oxa-8-azaspiro[4.5]decan-8-yl]pyridine-2-carboxylate (250 mg, 616 umol) in CH$_3$CN (5 mL) was added NBS (165 mg, 925 umol). The mixture was stirred at 0° C. for 5 min. The reaction mixture was quenched by the addition of H$_2$O (3 mL) at 25° C. The reaction mixture was extracted with EtOAc and the combined organic layers were washed with brine, dried over Na$_2$SO$_4$, filtered and concentrated under reduced pressure. The residue was purified by column chromatography to afford methyl 6-bromo-3-[(3S,4S)-4-(tert-butoxycarbonylamino)-3-methyl-2-oxa-8-azaspiro[4.5]decan-8-yl]pyridine-2-carboxylate (200 mg, 67% yield) as a white solid. $^1$H NMR (400 MHz, Chloroform-d) δ ppm 7.47 (d, J=8.7 Hz, 1H), 7.29 (s, 1H), 4.59 (d, J=11.0 Hz, 1H), 4.18-4.14 (m, 1H), 4.01 (s, 1H), 4.00-3.96 (m, 1H), 3.95 (s, 3H), 3.71-3.61 (m, 2H), 3.22-2.87 (m, 4H), 3.22-2.87 (m, 1H), 1.96-1.75 (m, 3H), 1.72-1.63 (m, 1H), 1.50 (s, 1H), 1.46 (s, 9H), 1.20 (d, J=6.2 Hz, 3H). LCMS (ESI): m/z: [M+H] calculated for C$_{21}$H$_{31}$BrN$_3$O$_5$:484.1, 486.1; found 484.1, 486.2.

Step 4

To a solution of methyl 6-bromo-3-[(3S,4S)-4-(tert-butoxycarbonylamino)-3-methyl-2-oxa-8-azaspiro[4.5]decan-8-yl]pyridine-2-carboxylate (184 mg, 380 umol) in 1,4-dioxane (2 mL) was added 2-amino-3-chloro-pyridine-4-thiol (73 mg, 456 umol), 1,10-Phenanthroline (14 mg, 76 umol), CuI (7 mg, 38 umol) and K$_3$PO$_4$ (161 mg, 760 umol) at 20° C., and the mixture was degassed with N$_2$. The reaction mixture was heated to 140° C. for 1 hr under N$_2$. The reaction mixture was filtered and concentrated under reduced pressure. The resulting residue was purified by prep-HPLC to afford methyl 6-[(2-amino-3-chloro-4-pyridyl)sulfanyl]-3-[(3S,4S)-4-(tert-butoxycarbonylamino)-3-methyl-2-oxa-8-azaspiro[4.5]decan-8-yl]pyridine-2-carboxylate (140 mg, 65% yield) as a white solid. LCMS (ESI): m/z: [M+H] calculated for C$_{26}$H$_{35}$ClN$_5$O$_5$S: 564.2; found 564.3.

Step 5

To a solution of methyl 6-[(2-amino-3-chloro-4-pyridyl)sulfanyl]-3-[(3S,4S)-4-(tert-butoxycarbonylamino)-3-methyl-2-oxa-8-azaspiro[4.5]decan-8-yl]pyridine-2-carboxylate (90 mg, 159 umol) in THF (1 mL) was added LiBH$_4$ (10 mg, 479 umol). The mixture was stirred at 50° C. for 30 min. To the mixture was added 0.2 mL of HCl and the mixture was stirred at 25° C. for 30 min. The mixture was adjusted to pH=7 with NaHCO$_3$, filtered and the filtrate was concentrated under reduced pressure. The residue was purified by prep-HPLC to afford [6-[(2-amino-3-chloro-4-pyridyl)sulfanyl]-3-[(3S,4S)-4-amino-3-methyl-2-oxa-8-azaspiro[4.5]decan-8-yl]-2-pyridyl]methanol (6 mg, 9% yield) as a yellow solid. $^1$H NMR (400 MHz, Methanol-d4) δ ppm 8.49 (s, 1H), 7.69-7.56 (m, 2H), 7.53-7.47 (m, 1H), 6.16 (d, J=5.5 Hz, 1H), 4.73 (s, 2H), 4.32-4.22 (m, 1H), 3.93 (d, J=9.2 Hz, 1H), 3.82 (d, J=9.0 Hz, 1H), 3.41 (d, J=4.2 Hz, 1H), 3.25-3.11 (m, 2H), 2.91-2.75 (m, 2H), 2.05-1.95 (m, 2H), 1.94-1.85 (m, 1H), 1.74 (d, J=12.7 Hz, 1H), 1.30 (d, J=6.5 Hz, 3H). LCMS (ESI): m/z [M+H] calculated for C$_{20}$H$_{27}$ClN$_5$O$_2$S: 436.1; found 436.3.

Example 6. Synthesis of {3-[(3S,4S)-4-amino-3-methyl-2-oxa-8-azaspiro[4.5]decan-8-yl]-6-(5,6-dichloro-2H-1,3-benzodioxol-4-yl)pyrazin-2-yl}methanol. (Compound 6)

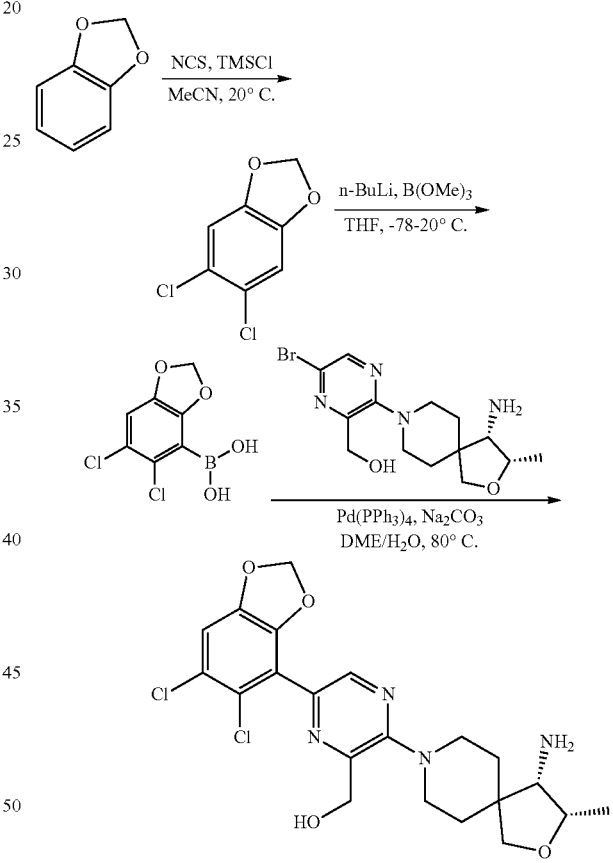

Step 1

To a solution of 1,3-benzodioxole (500 mg, 4.09 mmol, 1.0 eq) in MeCN (5 mL) was added TMSCl (44.48 mg, 409.43 umol) and NCS (1.20 g, 9.01 mmol). The mixture was stirred at 20° C. for 2 hr and then quenched by addition aqueous Na$_2$S$_2$O$_3$ (10 ml). After extraction with EtOAc the combined organic layers were washed with brine, dried over Na$_2$SO$_4$, filtered and concentrated under reduced pressure. The crude residue was purified by column chromatography to give 5,6-dichloro-1,3-benzodioxole (620 mg, 3.25 mmol, 79% yield) as a white solid. $^1$H NMR (400 MHz, METHANOL-d4) δ ppm 6.98 (s, 2H) 6.02 (s, 2H).

Step 2 n-BuLi (2.5 M, 500 uL) was added drop wise to a mixture of 5,6-dichloro-1,3-benzodioxole (200 mg, 1.1 mmol) in THF (5 mL) at −78° C. After 30 min, B(OMe)$_3$ (163 mg, 1.6 mmol) was added at −78° C. The reaction was allowed to warm to 20° C. for over 2 hr and 1N HCl was added. After extraction with EtOAc the combined organic layers were washed with brine, dried over Na$_2$SO$_4$, filtered and concentrated under reduced pressure to give (5,6-dichloro-1,3-benzodioxol-4-yl)boronic acid (200 mg, 684 umol, 80% purity) as a light yellow solid. LCMS (ESI): m/z: [M−H] calculated for C$_7$H$_4$BCl$_2$O$_4$: 232.9; found 233.0.

Step 3

To a solution of [3-[(3S,4S)-4-amino-3-methyl-2-oxa-8-azaspiro[4.5]decan-8-yl]-6-bromo-pyrazin-2-yl]methanol (for synthesis see example 1, 100 mg, 280 μmol) in DME (2 mL) and H$_2$O (0.4 mL) was added (5,6-dichloro-1,3-benzodioxol-4-yl)boronic acid (79 mg, 336 μmol), Na$_2$CO$_3$ (59 mg, 560 μmol) and Pd(PPh$_3$)$_4$ (32 mg, 28 μmol, 0.1 eq). The mixture was heated at 110° C. for 24 hr under N$_2$. After cooling to rt, the reaction mixture was concentrated under reduced pressure to give a crude residue, which was purified by prep-HPLC to give {3-[(3S,4S)-4-amino-3-methyl-2-oxa-8-azaspiro[4.5]decan-8-yl]-6-(5,6-dichloro-2H-1,3-benzodioxol-4-yl)pyrazin-2-yl}methanol (6.5 mg, 13.3 umol, 5% yield) as a white solid. LCMS (ESI): m/z: [M+H] calculated for C$_{21}$H$_{24}$Cl$_2$N$_4$O$_4$: 467.1; found 467.2; $^1$H NMR (400 MHz, DMSO-d$_6$) δ ppm 8.23 (s, 1H) 7.28 (d, J=1.71 Hz, 1H) 6.11 (s, 2H) 4.94 (br s, 1H) 4.60 (br s, 2H) 3.73 (br d, J=8.31 Hz, 1H) 3.63 (br d, J=13.20 Hz, 3H) 3.56 (br d, J=9.17 Hz, 1H) 3.11-3.30 (m, 3H) 1.89 (br d, J=8.44 Hz, 1H) 1.75-1.84 (m, 1H) 1.81 (br d, J=14.18 Hz, 2H) 1.56-1.69 (m, 3H) 1.14 (br d, J=6.48 Hz, 3H).

Example 7. Synthesis of {3-[(3S,4S)-4-amino-3-methyl-2-oxa-8-azaspiro[4.5]decan-8-yl]-6-(2,3-dichloro-6-methoxyphenyl)pyrazin-2-yl}methanol. (Compound 7)

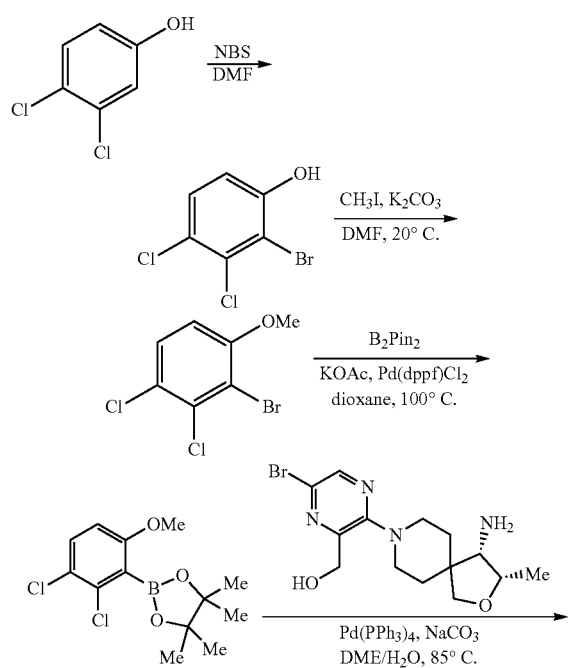

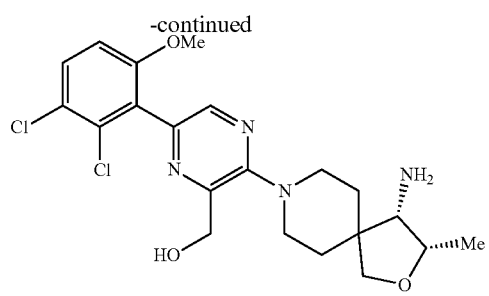

Step 1

To a solution of 3,4-dichlorophenol (4 g, 24.5 mmol) in DMF (40 mL) was added NBS (4.4 g, 24.5 mmol) at 0° C. After stirring for 30 min at 0° C. the solvent was removed under reduced pressure and the crude residue was purified by column chromatography to give 2-bromo-3,4-dichlorophenol (0.95 g, 4.0 mmol, 16% yield) as a white solid. $^1$H NMR (400 MHz, DMSO-d6) δ ppm 11.00 (s, 1H) 7.46 (d, J=9.04 Hz, 1H) 6.95 (d, J=8.82 Hz, 1H).

Step 2

To a solution of 2-bromo-3,4-dichloro-phenol (0.35 g, 1.5 mmol) in DMF (2 mL) was added K$_2$CO$_3$ (540 mg, 3.9 mmol) and CH$_3$I (0.4 ml, 6.5 mmol) at 20° C. After 3 hr the reaction was diluted with water and extracted with ethyl acetate. The combined organic layers were dried over magnesium sulfate. The solvent was removed under reduced pressure and the crude residue was purified by column chromatography to give 3-bromo-1,2-dichloro-4-methoxy-benzene (0.3 g, 1.2 mmol, 81% yield) as a white solid. $^1$H NMR (400 MHz, METHANOL-d4) δ ppm 7.49 (d, J=9.04 Hz, 1H) 7.00 (d, J=9.04 Hz, 1H) 3.90 (s, 3H).

Step 3

To a solution of 3-bromo-1,2-dichloro-4-methoxy-benzene (0.25 g, 0.98 mmol) in dioxane (6 mL) was added 4,4,5,5-tetramethyl-2-(4,4,5,5-tetramethyl-1,3,2-dioxaborolan-2-yl)-1,3,2-dioxaborolane (372 mg, 1.5 mmol), KOAc (192 mg, 1.9 mmol) and Pd(dppf)Cl$_2$—CH$_2$Cl$_2$ (80 mg, 97.7 μmol). The reaction mixture was stirred at 85° C. for 5 hr under N$_2$. Upon cooling to rt, the reaction was diluted with water and extracted with ethyl acetate. The combined organic layers were dried over Na$_2$SO$_4$, filtered, and concentrated under reduced pressure. The crude residue was purified by column chromatography to give 2-(2,3-dichloro-6-methoxy-phenyl)-4,4,5,5-tetramethyl-1,3,2-dioxaborolane (0.19 g, 0.63 mmol, 64% yield) as a yellow solid. $^1$H NMR (400 MHz, METHANOL-d4) δ ppm 7.44 (d, J=8.93 Hz, 1H) 6.89 (d, J=8.80 Hz, 1H) 3.78 (s, 3H) 1.37 (s, 12H).

Step 4

To a solution of [3-[(3S,4S)-4-amino-3-methyl-2-oxa-8-azaspiro[4.5]decan-8-yl]-6-bromo-pyrazin-2-yl]methanol (for synthesis see example 1, 79 mg, 220 μmol) in DME (2 mL) was added 2-(2,3-dichloro-6-methoxy-phenyl)-4,4,5,5-tetramethyl-1,3,2-dioxaborolane (0.1 g, 330 μmol), Na$_2$CO$_3$ (47 mg, 440 μmol), H$_2$O (0.4 mL) and Pd(PPh$_3$)$_4$ (25 mg, 22 μmol). The reaction was stirred at 85° C. for 5 hr under N$_2$. After cooling to rt the mixture was filtrated and the solvent was removed under reduced pressure and the crude residue was purified by prep-HPLC to give {3-[(3S,4S)-4-amino-3-methyl-2-oxa-8-azaspiro[4.5]decan-8-yl]-6-(2,3-dichloro-6-methoxyphenyl)pyrazin-2-yl}methanol (2.9 mg, 6 umol, 3% yield) as a white solid. LCMS (ESI): m/z: [M+H] calculated for $C_{21}H_{27}Cl_2N_4O_3$: 453.1; found 453.3; $^1$H NMR (400 MHz, METHANOL-d4) δ ppm 8.49 (br s, 1H) 8.10-8.07 (m, 1H) 7.58 (d, J=9.04 Hz, 1H) 7.10 (d, J=9.04 Hz, 1H) 4.71 (s, 2H) 4.29 (dd, J=6.51, 4.30 Hz, 1H) 3.95 (d, J=9.04 Hz, 1H) 3.84 (d, J=9.04 Hz, 1H) 3.75 (s, 3H) 3.71-3.65 (m, 1H) 3.39 (d, J=4.19 Hz, 1H) 3.16-3.01 (m, 2H) 2.04-1.86 (m, 3H) 1.74 (d, J=12.57 Hz, 1H) 1.30 (d, J=6.62 Hz, 3H).

Example 8. Synthesis of 2-{5-[(3S,4S)-4-amino-3-methyl-2-oxa-8-azaspiro[4.5]decan-8-yl]-6-(hydroxymethyl)pyrazin-2-yl}-3,4-dichlorophenol (Compound 8)

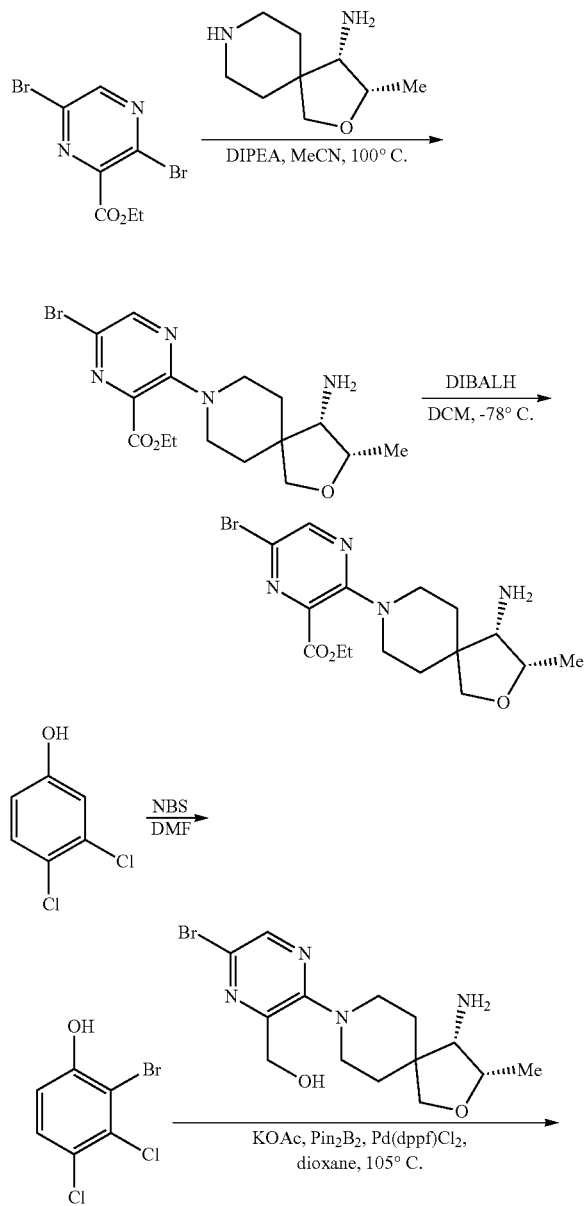

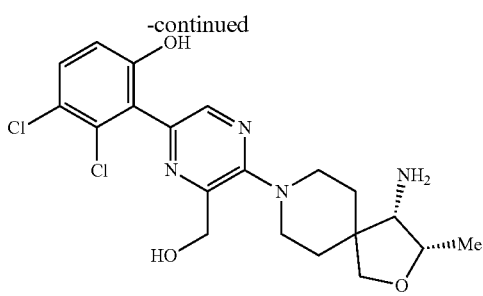

Step 1

To a solution of methyl 3,6-dibromopyrazine-2-carboxylate (8.4 g, 28.3 mmol) in MeCN (142 mL) was added (3S,4S)-3-methyl-2-oxa-8-azaspiro[4.5]decan-4-amine bishydrochloride (7.59 g, 31.2 mmol), DIEA (24.7 ml, 142 mmol). The reaction mixture was stirred at rt for 16 hr. The solvent was removed under reduced pressure and the residue was partitioned between water/NH$_4$OH (10:1) and EtOAc. The phases were separated and the aqueous phase was extracted with EtOAc. The combined organic phases were dried over anhydrous Na$_2$SO$_4$, filtered and concentrated to give methyl 3-[(3S,4S)-4-amino-3-methyl-2-oxa-8-azaspiro[4.5]decan-8-yl]-6-bromo-pyrazine-2-carboxyte (12 g, crude), which was used without further purification. LCMS (ESI): m/z: [M+H] calculated for $C_{15}H_{22}BrN_4O_3$: 385.1; found 385.1.

Step 2

To a solution of ethyl 3-[(3S,4S)-4-amino-3-methyl-2-oxa-8-azaspiro[4.5]decan-8-yl]-6-bromo-5-methyl-pyrazine-2-carboxylate (12 g, 29.0 mmol) in DCM (240 mL) at −78° C. was added DIBAL-H (1 M, 116 mL) over 10 min. The reaction mixture was stirred at −78° C. for 1 hr and then warmed to 0° C. for 1 hr. The reaction was quenched by pouring it into saturated aqueous Rochelle's salt solution. EtOAc was added and the reaction was allowed to warm to rt overnight while stirring vigorously. The biphasic mixture was then separated, and the aqueous phase was extracted with EtOAc. The combined organic extracts were dried over Na$_2$SO$_4$, filtered and concentrated. The yellow residue was triturated with EtOAc to give [3-[(3S,4S)-4-amino-3-methyl-2-oxa-8-azaspiro[4.5]decan-8-yl]-6-bromo-5-methyl-pyrazin-2-yl]methanol (4.86 g, 45% yield). $^1$H NMR (400 MHz, DMSO-d$_6$) δ ppm 8.27 (s, 1H) 5.51 (s, 1H) 4.43 (s, 1 H) 4.05-4.02 (m, 1H) 3.62 (d, J=8.38 Hz, 1H) 3.44 (d, J=8.60 Hz, 1H) 3.34-3.26 (m, 2H) 3.13-2.95 (m, 2H) 2.86 (d, J=4.85 Hz, 1H) 1.84-1.61 (m, 2H) 1.60-1.42 (m, 2H) 1.32 (s, 2H) 1.05 (d, J=6.39 Hz, 2H).

Step 3

To a solution of 3,4-dichlorophenol (4 g, 24.54 mmol) in DMF (40 mL) was added NBS (4.37 g, 24.54 mmol) at 0° C. and the reaction was stirred for 0.5 hr. The solvent was evaporated under reduced pressure and the crude residue was purified by column chromatography to give 2-bromo-3,4-dichloro-phenol (0.95 g, 3.93 mmol, 16% yield) as a white solid. $^1$H NMR (400 MHz, DMSO-d$_6$) δ ppm 11.00 (s, 1H) 7.46 (d, J=9.04 Hz, 1H) 6.95 (d, J=8.82 Hz, 1H).

Step 4

To a solution of 2-bromo-3,4-dichloro-phenol (0.3 g, 1.24 mmol) in dioxane (6 mL) was added [3-[(3S,4S)-4-amino- 3-methyl-2-oxa-8-azaspiro[4.5]decan-8-yl]-6-bromo-pyrazin-2-yl]methanol (443.1 mg, 1.24 mmol), KOAc (243.4 mg, 2.48 mmol), 4,4,5,5-tetramethyl-2-(4,4,5,5-tetramethyl-1,3,2-dioxaborolan-2-yl)-1,3,2-dioxaborolane (472.4 mg, 1.86 mmol) and Pd(dppf)Cl$_2$—CH$_2$Cl$_2$ (101.3 mg, 124.0 µmol) at 20° C. under N$_2$, the mixture was heated to 105° C. for 2 hr. After cooling to rt and filtration the solvent was removed under reduced pressure and the crude residue was purified by prep-HPLC to give 2-{5-[(3S,4S)-4-amino-3-methyl-2-oxa-8-azaspiro[4.5]decan-8-yl]-6-(hydroxymethyl)pyrazin-2-yl}-3,4-dichlorophenol (3 mg, 7 umol, 51% yield) as a white solid. LCMS (ESI): m/z: [M+H] calculated for C$_{20}$H$_{25}$Cl$_2$N$_4$O$_3$: 439.1; found 439.1. $^1$H NMR (400 MHz, METHANOL-d$_4$) δ ppm 8.52 (br s, 1H) 8.22 (s, 1H) 7.40 (d, J=8.82 Hz, 1H) 6.88 (d, J=9.04 Hz, 1H) 4.72 (s, 2H) 4.25-4.32 (m, 1H) 3.93 (d, J=9.04 Hz, 1H) 3.82 (d, J=9.48 Hz, 1H) 3.62-3.74 (m, 3H) 3.01-3.16 (m, 3H) 1.93-2.02 (m, 2H) 1.86 (br d, J=13.23 Hz, 1H) 1.73 (br d, J=13.45 Hz, 1H) 1.29 (d, J=6.39 Hz, 3H).

Example 9. Synthesis of {3-[(3S,4S)-4-amino-3-methyl-2-oxa-8-azaspiro[4.5]decan-8-yl]-6-(5-chloroquinoxalin-6-yl)pyrazin-2-yl}methanol. (Compound 9)

{3-[(3S,4S)-4-amino-3-methyl-2-oxa-8-azaspiro[4.5]decan-8-yl]-6-(5-chloroquinoxalin-6-yl)pyrazin-2-yl}methanol was synthesized in a manner similar to 2-{5-[(3S,4S)-4-amino-3-methyl-2-oxa-8-azaspiro[4.5]decan-8-yl]-6-(hydroxymethyl)pyrazin-2-yl}-3,4-dichlorophenol except 2-bromo-3,4-dichloro-phenol was substituted with 6-bromo-5-chloro-quinoxaline. LCMS (ESI): m/z: [M+H] calculated for C$_{22}$H$_{26}$ClN$_6$O$_2$: 441.2; found 440.9; $^1$H NMR (400 MHz, METHANOL-d4) δ ppm 9.01 (br d, J=13.23 Hz, 2H) 8.71 (s, 1H) 8.49 (br s, 1H) 8.25-8.20 (m, 1H) 8.18-8.13 (m, 1H) 4.78 (s, 2H) 4.34-4.26 (m, 1H) 3.97 (d, J=9.26 Hz, 1H) 3.88-3.73 (m, 3H) 3.40 (br d, J=3.75 Hz, 1H) 3.23-3.06 (m, 2H) 2.05-1.95 (m, 2H) 1.94-1.87 (m, 1H) 1.76 (br d, J=13.45 Hz, 1H) 1.31 (d, J=6.39 Hz, 3H).

Example 10. Synthesis of {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol. (Compound 10)

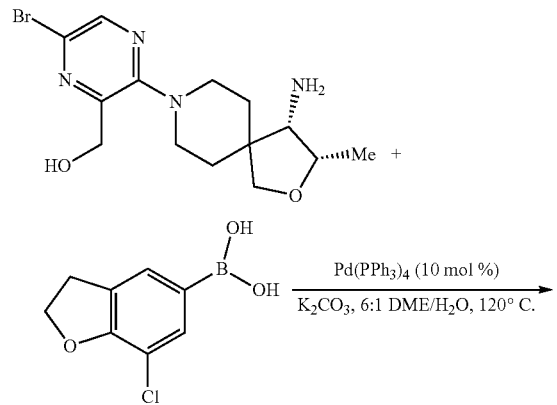

-continued

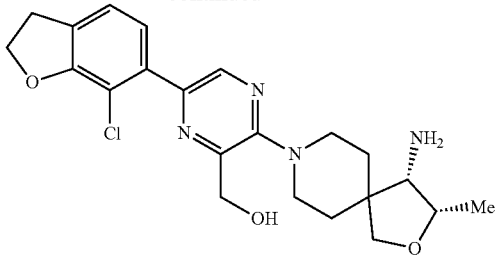

To a microwave vial was added {3-[(3S,4S)-4-amino-3-methyl-2-oxa-8-azaspiro[4.5]decan-8-yl]-6-bromopyrazin-2-yl}methanol (for synthesis see example 1, 30 mg, 84 µmol), (7-chloro-2,3-dihydro-1-benzofuran-6-yl)boronic acid (25 mg, 125 µmol), tetrakis(triphenylphosphine) palladium (10 mg, 8.4 µmol), and potassium carbonate (35 mg, 250 µmol). The reaction vial was evacuated and purged with N$_2$ three times before stirring under microwave conditions at 120° C. for 1.5 hr. The resulting reaction mixture was filtered through a pad of celite, washing with DCM and MeOH. The filtrate was concentrated under reduced pressure and the residue was subjected to column chromatography, followed by reverse phase HPLC to yield the desired product, {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol (10.0 mg, 23.2 µmol, 28%). LCMS (ESI): m/z: [M+H] calcd for C$_{21}$H$_{26}$ClN$_7$OS: 431.2; found 431.4. $^1$H NMR (500 MHz, Methanol-d$_4$) δ 8.38 (s, 1H), 7.22 (dt, J=7.6, 1.1 Hz, 1H), 7.10 (d, J=7.6 Hz, 1H), 4.68 (t, J=8.8 Hz, 4H), 4.33-4.24 (m, 1H), 3.94 (d, J=9.1 Hz, 1H), 3.83 (d, J=9.1 Hz, 1H), 3.74-3.58 (m, 2H), 3.40 (d, J=4.2 Hz, 1H), 3.35 (td, J=8.8, 1.1 Hz, 2H), 3.14-2.98 (m, 2H), 2.04-1.92 (m, 2H), 1.88 (d, J=13.5 Hz, 1H), 1.77-1.69 (m, 1H), 1.30 (d, J=6.6 Hz, 3H).

Example 11. Synthesis of {3-[(3S,4S)-4-amino-3-methyl-2-oxa-8-azaspiro[4.5]decan-8-yl]-6-(1H-indol-7-yl)pyrazin-2-yl}methanol. (Compound 11)

{3-[(3S,4S)-4-amino-3-methyl-2-oxa-8-azaspiro[4.5]decan-8-yl]-6-(1H-indol-7-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (1H-indol-7-yl)boronic acid. LCMS (ESI): m/z: [M+H] calculated for C$_{22}$H$_{27}$N$_5$O$_2$: 394.2; found 394.5; $^1$H NMR (500 MHz, Methanol-d4) δ 8.50 (s, 1H), 8.48 (s, 1H), 7.53 (dt, J 7.9, 1.0 Hz, 1H), 7.39 (dd, J=8.3, 1.0 Hz, 1H), 7.18 (ddd, J=8.2, 7.0, 1.1 Hz, 1H), 7.14 (S, 1H) 7.03 (ddd, J=7.9, 7.0, 0.9 Hz, 1H), 6.80 (d, J=0.8 Hz, 1H), 4.72 (s, 2H), 4.30-4.18 (m, 1H), 3.88 (d, J=9.0 Hz, 1H), 3.77 (d, J=8.9 Hz, 1H), 3.65-3.52 (m, 2H), 3.29 (d, J=1.6 Hz, 1H), 3.13-2.95 (m, 2H), 1.98-1.87 (m, 2H), 1.82 (d, J=13.5 Hz, 1H), 1.69 (d, J=13.1 Hz, 1H), 1.25 (d, J=6.5 Hz, 4H).

Example 12. Synthesis of {3-[(3S,4S)-4-amino-3-methyl-2-oxa-8-azaspiro[4.5]decan-8-yl]-6-(quinoxalin-6-yl)pyrazin-2-yl}methanol. (Compound 12)

{3-[(3S,4S)-4-amino-3-methyl-2-oxa-8-azaspiro[4.5]decan-8-yl]-6-(quinoxalin-6-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3- dihydro-1-benzofuran-6-yl)pyrazin-2-yl}methanol except (7-chloro-2,3-dihydro-1-benzofuran-6-yl)boronic acid was substituted with 6-quinoxalinyl-boronic acid. LCMS (ESI): m/z: [M+H] calculated for $C_{22}H_{26}N_6O_2$: 407.2; found 407.5. $^1$H NMR (500 MHz, Methanol-$d_4$) δ 8.90 (dd, J=18.4, 1.9 Hz, 2H), 8.82 (s, 1H), 8.71 (d, J=1.9 Hz, 1H), 8.59 (dd, J=8.9, 2.0 Hz, 1H), 8.16 (d, J=8.9 Hz, 1H), 4.79 (s, 2H), 3.99 (d, J=9.1 Hz, 1H), 3.88 (d, J=9.1 Hz, 1H), 3.50 (d, J=4.1 Hz, 1H), 3.37 (s, 1H), 2.68 (s, 3H), 1.35 (d, J=6.5 Hz, 3H).

Example 13. Synthesis of {3-[(3S,4S)-4-amino-3-methyl-2-oxa-8-azaspiro[4.5]decan-8-yl]-6-(4-chloro-2H-indazol-6-yl)pyrazin-2-yl}methanol. (Compound 13)

{3-[(3S,4S)-4-amino-3-methyl-2-oxa-8-azaspiro[4.5]decan-8-yl]-6-(4-chloro-2H-indazol-6-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (4-chloro-1H-indazol-6-yl)boronic acid. LCMS (ESI): m/z: [M+H] calculated for $C_{21}H_{25}ClN_6O_2$: 429.2; found 429.0; $^1$H NMR (400 MHz, METHANOL-$d_4$) δ ppm 8.67 (s, 1H) 8.12 (d, J=12.79 Hz, 2H) 7.93 (s, 1H) 4.76 (s, 2H) 4.19-4.30 (m, 1H) 3.86 (d, J=8.38 Hz, 1H) 3.72 (d, J=8.60 Hz, 1H) 3.56 (br dd, J=11.69, 5.95 Hz, 2H) 3.16 (br t, J=10.69 Hz, 1H) 3.06-3.11 (m, 1H) 3.04 (d, J=4.85 Hz, 1H) 1.85-2.01 (m, 2H) 1.67-1.80 (m, 2H) 1.23 (d, J=6.39 Hz, 3H).

Example 14. Synthesis of {3-[(3S,4S)-4-amino-3-methyl-2-oxa-8-azaspiro[4.5]decan-8-yl]-6-(5-chloro-2H-indazol-6-yl)pyrazin-2-yl}methanol. (Compound 14)

{3-[(3S,4S)-4-amino-3-methyl-2-oxa-8-azaspiro[4.5]decan-8-yl]-6-(5-chloro-2H-indazol-6-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with 5-chloro-6-(4,4,5,5-tetramethyl-1,3,2-dioxaborolan-2-yl)-1H-indazole. LCMS (ESI): m/z: [M+H] calculated for $C_{21}H_{26}ClN_6O_2$: 429.2; found 429.0; $^1$H NMR (400 MHz, DMSO-d6) δ ppm 8.44 (s, 1H) 8.23 (br s, 1H) 8.13 (s, 1H) 8.01 (s, 1H) 7.79 (s, 1H) 4.59 (s, 2H) 4.08-4.16 (m, 1H) 3.75 (br d, J=8.38 Hz, 1H) 3.54-3.67 (m, 3H) 3.03-3.19 (m, 3H) 1.76-1.93 (m, 2H) 1.55-1.70 (m, 2H) 1.14 (d, J=6.39 Hz, 3H).

Example 15. Synthesis of {3-[(3S,4S)-4-amino-3-methyl-2-oxa-8-azaspiro[4.5]decan-8-yl]-6-(1-methyl-1H-indol-2-yl)pyrazin-2-yl}methanol. (Compound 15)

{3-[(3S,4S)-4-amino-3-methyl-2-oxa-8-azaspiro[4.5]decan-8-yl]-6-(1-methyl-1H-indol-2-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (1-methyl-1H-indol-2-yl)boronic acid. LCMS (ESI): m/z: [M+H] calcd for $C_{21}H_{26}ClN_7OS$: 408.2; found 408.1. $^1$H NMR (500 MHz, Methanol-d4) δ 8.50 (s, 1H), 8.48 (s, 1H), 7.53 (dt, J=7.9, 1.0 Hz, 1H), 7.39 (dd, J=8.3, 1.0 Hz, 1H), 7.18 (ddd, J=8.2, 7.0, 1.1 Hz, 1H), 7.03 (ddd, J=7.9, 7.0, 0.9 Hz, 1H), 6.80 (d, J=0.8 Hz, 1H), 4.72 (s, 2H), 4.30-4.18 (m, 1H), 4.00 (s, 3H), 3.88 (d, J=9.0 Hz, 1H), 3.77 (d, J=8.9 Hz, 1H), 3.65-3.52 (m, 2H), 3.29 (d, J=1.6 Hz, 1H), 3.13-2.95 (m, 2H), 1.98-1.87 (m, 2H), 1.82 (d, J=13.5 Hz, 1H), 1.69 (d, J=13.1 Hz, 1H), 1.25 (d, J 6.5 Hz, 3H).

Example 16. Synthesis of {3-[(3S,4S)-4-amino-3-methyl-2-oxa-8-azaspiro[4.5]decan-8-yl]-6-(8-chloro-3,4-dihydro-2H-1-benzopyran-7-yl)pyrazin-2-yl}methanol (Compound 16)

{3-[(3S,4S)-4-amino-3-methyl-2-oxa-8-azaspiro[4.5]decan-8-yl]-6-(8-chloro-3,4-dihydro-2H-1-benzopyran-7-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (8-chloro-3,4-dihydro-2H-1-benzopyran-7-yl)boronic acid. LCMS (ESI): m/z: [M+H] calcd for $C_{21}H_{26}ClN_7OS$: 445.2; found 445.4; $^1$H NMR (500 MHz, Methanol-$d_4$) δ 8.36 (s, 1H), 7.12-7.01 (m, 2H), 4.69 (s, 2H), 4.29-4.26 (m, 3H), 3.93 (d, J=9.2 Hz, 1H), 3.82 (d, J=9.2 Hz, 1H), 3.72-3.59 (m, 1H), 3.41 (d, J=4.1 Hz, 1H), 3.03 (dddd, J=31.9, 13.5, 11.1, 2.8 Hz, 2H), 2.85 (t, J=6.5 Hz, 2H), 2.63 (s, 2H), 2.05-1.91 (m, 3H), 1.87 (d, J=13.4 Hz, 1H), 1.75-1.67 (m, 1H), 1.28 (d, J=6.5 Hz, 3H).

Example 17. Synthesis of {3-[(3S,4S)-4-amino-3-methyl-2-oxa-8-azaspiro[4.5]decan-8-yl]-6-(2-chloro-6-fluoro-3-methoxyphenyl)pyrazin-2-yl}methanol. (Compound 17)

{3-[(3S,4S)-4-amino-3-methyl-2-oxa-8-azaspiro[4.5]decan-8-yl]-6-(2-chloro-6-fluoro-3-methoxyphenyl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (2-chloro-6-fluoro-3-methoxyphenyl)boronic acid. LCMS (ESI): m/z: [M+H] calcd for $C_{21}H_{26}ClN_7OS$: 437.2; found 437.2; $^1$H NMR (500 MHz, Methanol-$d_4$) δ 8.20 (d, J=0.7 Hz, 1H), 7.23-7.18 (m, 2H), 4.74 (s, 2H), 4.35-4.26 (m, 1H), 3.97 (d, J=9.0 Hz, 1H), 3.94 (s, 3H), 3.86 (d, J=9.1 Hz, 1H), 3.82-3.69 (m, 2H), 3.39 (d, J=4.3 Hz, 1H), 3.22-3.05 (m, 2H), 2.07-1.96 (m, 2H), 1.90 (d, J=13.8 Hz, 1H), 1.76 (d, J=12.5 Hz, 1H), 1.32 (d, J=6.5 Hz, 3H).

Example 18. Synthesis of {3-[(3S,4S)-4-amino-3-methyl-2-oxa-8-azaspiro[4.5]decan-8-yl]-6-(2,3,6-trichlorophenyl)pyrazin-2-yl}methanol. (Compound 18)

{3-[(3S,4S)-4-amino-3-methyl-2-oxa-8-azaspiro[4.5]decan-8-yl]-6-(2,3,6-trichlorophenyl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (2,3,6-trichlorophenyl)boronic acid. LCMS (ESI): m/z: [M+H] calcd for $C_{20}H_{23}Cl_3N_4O_2$: 457.1; found 457.2; $^1$H NMR (500 MHz, Methanol-d4) δ 8.69-8.50 (m, 1H), 8.50 (s, 1H), 7.72 (d, J=2.5 Hz, 1H), 7.70 (d, J=2.5 Hz, 1H), 4.75 (s, 2H), 4.33 (qd, J=6.5, 4.2 Hz, 1H), 3.99 (dd, J=9.1, 0.8 Hz, 1H), 3.88 (dd, J=9.2, 0.8 Hz, 1H), 3.82 (dtd, J=13.4, 4.1, 1.6 Hz, 1H), 3.78-3.73 (m, 1H), 3.47 (d, J=4.2 Hz, 1H), 3.16 (ddd, J=13.8, 11.1, 2.9 Hz, 1H), 3.09 (ddd, J=13.6, 11.2, 2.7 Hz, 1H), 2.01 (ddd, J=13.6, 8.4, 3.5 Hz, 2H), 1.95-1.89 (m, 1H), 1.82-1.71 (m, 1H), 1.35 (d, J=6.5 Hz, 3H).

Example 19. Synthesis of {3-[(3S,4S)-4-amino-3-methyl-2-oxa-8-azaspiro[4.5]decan-8-yl]-6-(2H-indazol-5-yl)pyrazin-2-yl}methanol. (Compound 19)

{3-[(3S,4S)-4-amino-3-methyl-2-oxa-8-azaspiro[4.5]decan-8-yl]-6-(2H-indazol-5-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with (1H-indazol-6-yl)boronic acid. LCMS (ESI): m/z: [M+H] calcd for $C_{21}H_{26}N_6O_2$: 395.2; found 395.4; $^1$H NMR (500 MHz, Methanol-$d_4$) δ 8.67 (s, 1H), 8.47 (dd, J=1.7, 0.8 Hz, 1H), 8.18-8.12 (m, 2H), 7.65 (d, J=8.8 Hz, 1H), 4.77 (s, 2H), 3.96 (d, J=9.1 Hz, 1H), 3.85 (d, J=9.1 Hz, 1H), 3.48 (d, J=4.1 Hz, 1H), 3.37 (s, 3H), 2.68 (s, 0H), 2.00 (s, 1H), 1.34 (d, J=6.5 Hz, 3H).

Example 20. Synthesis of {3-[(3S,4S)-4-amino-3-methyl-2-oxa-8-azaspiro[4.5]decan-8-yl]-6-(2H-indazol-5-yl)pyrazin-2-yl}methanol (Compound 20)

{3-[(3S,4S)-4-Amino-3-methyl-2-oxa-8-azaspiro[4.5]decan-8-yl]-6-(2H-indazol-5-yl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with 1H-indazol-6-ylboronic acid. LCMS (ESI): m/z: [M+H] calculated for $C_{21}H_{27}N_6O_2$: 395.2; found 395.4; $^1$H NMR (400 MHz, DMSO-$d_6$) δ ppm 13.20 (s, 1H) 8.78 (s, 1H) 8.21 (s, 1H) 8.10 (s, 1H) 7.84 (s, 2H) 5.39 (s, 1H) 4.61 (s, 2H) 4.12-4.06 (m, 1H) 3.69 (d, J=8.38 Hz, 1H) 3.52 (d, J=8.60 Hz, 2H) 3.20-3.02 (m, 3H) 2.96 (d, J=5.29 Hz, 1H) 1.76-1.74 (m, 2H) 1.68-1.52 (m, 2H) 1.10 (d, J=6.62 Hz, 3H).

Example 21. Synthesis of {3-[(3S,4S)-4-amino-3-methyl-2-oxa-8-azaspiro[4.5]decan-8-yl]-6-(2,3-dichlorophenyl)pyrazin-2-yl}methanol. (Compound 21)

{3-[(3S,4S)-4-amino-3-methyl-2-oxa-8-azaspiro[4.5]decan-8-yl]-6-(2,3-dichlorophenyl)pyrazin-2-yl}methanol was synthesized in a manner similar to {3-[(3S,4S)-4-amino-3-methyl-2-oxa-8-azaspiro[4.5]decan-8-yl]-6-(7-chloro-2,3-dihydro-1-benzofuran-6-yl)pyrazin-2-yl}methanol except (7-chloro-2,3-dihydro-1-benzofuran-6-yl)boronic acid was substituted with 2,3 dichlorobenzoic acid. LCMS (ESI): m/z: [M+H] calculated for $C_{20}H_{24}Cl_2N_4O_2$: 423.1; found 423.4; $^1$H NMR (500 MHz, Methanol-d4) δ 8.55 (s, 1H), 8.44 (d, J=0.6 Hz, 1H), 7.66-7.57 (m, 2H), 7.43 (t, J=7.9 Hz, 1H), 4.75 (d, J=0.5 Hz, 2H), 4.31 (qd, J=6.5, 4.3 Hz, 1H), 3.97 (dd, J=9.0, 0.8 Hz, 1H), 3.85 (dd, J=9.0, 0.8 Hz, 1H), 3.73 (ddtd, J=26.7, 13.4, 4.2, 1.6 Hz, 2H), 3.40-3.35 (m, 1H), 3.16 (ddd, J 13.6, 10.9, 2.9 Hz, 1H), 3.09 (ddd, J 13.5, 11.0, 2.8 Hz, 2H), 2.68 (s, 0H), 2.05-1.95 (m, 3H), 1.93-1.86 (m, 2H), 1.80-1.73 (m, 1H), 1.32 (d, J 6.5 Hz, 3H).

Example 22. Synthesis of 3-({5-[(3S,4S)-4-amino-3-methyl-2-oxa-8-azaspiro[4.5]decan-8-yl]-6-(hydroxymethyl)pyrazin-2-yl}sulfanyl)-2-chlorobenzonitrile. (Compound 22)

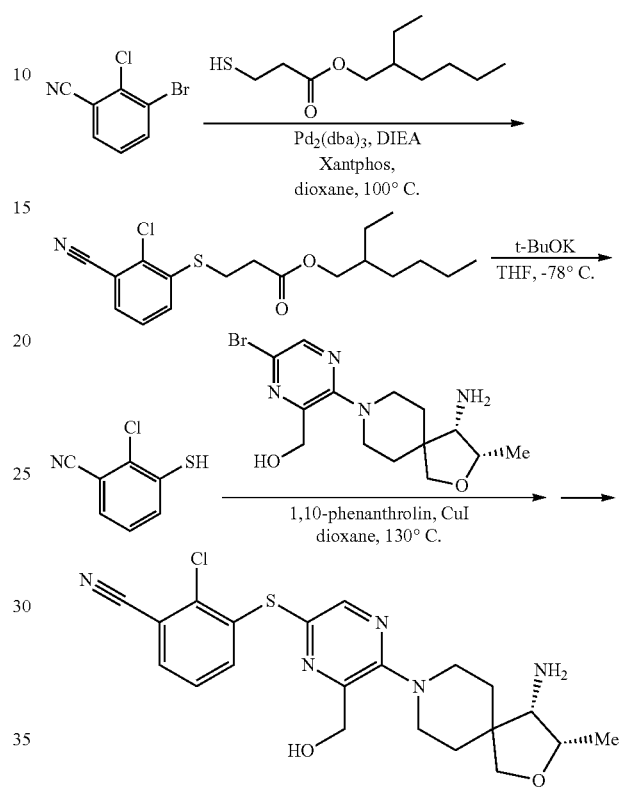

Step 1

To a mixture of 3-bromo-2-chloro-benzonitrile (0.5 g, 2.3 mmol) and 2-ethylhexyl 3-sulfanylpropanoate (656 mg, 3.0 mmol) in dioxane (4 mL) was added Xantphos (27 mg, 46 μmol), DIEA (0.8 ml, 4.6 mmol) and $Pd_2(dba)_3$ (11 mg, 12 μmol). The mixture was stirred at 100° C. for under $N_2$ for 5 hr and then cooled to rt, poured into water (2 mL) and extracted with EtOAc. The combined organic phases were dried over anhydrous $Na_2SO_4$, filtered and the solvent was removed under reduced pressure. The residue was purified by column chromatography to give 2-ethylhexyl 3-(2-chloro-3-methanimidoyl-phenyl)sulfanylpropanoate (720 mg, 88% yield) as a brown solid. $^1$H NMR (400 MHz, METHANOL-d4) δ=7.69 (dd, J=1.3, 8.2 Hz, 1H), 7.61 (dd, J=1.3, 7.7 Hz, 1H), 7.48-7.43 (m, 1H), 4.03 (d, J=5.7 Hz, 2H), 3.33 (s, 2H), 2.72 (t, J=6.8 Hz, 2H), 1.60-1.51 (m, 1H), 1.41-1.24 (m, 8H), 0.93-0.86 (m, 6H)

Step 2

To a mixture of 2-ethylhexyl 3-(2-chloro-3-cyano-phenyl)sulfanylpropanoate (720 mg, 2.0 mmol) in THF (4 mL) was added t-BuOK (1 M in THF, 3.1 mmol, 3.1 mL) at −78° C. under $N_2$. The mixture was stirred at −78° C. for 1 hr and then concentrated under reduced pressure. The crude residue was purified by column chromatography to give 2-chloro-3-mercaptobenzonitrile (260 mg, 63% yield) as a brown solid. ¹H NMR (400 MHz, METHANOL-d₄) δ=7.75 (dd, J=1.1, 7.9 Hz, 1H), 7.56 (dd, J=1.1, 7.7 Hz, 1H), 7.32 (t, J=7.9 Hz, 1H).

Step 3

To a solution of 2-chloro-3-mercaptobenzonitrile (116 mg, 560 umol) and [3-[(3S,4S)-4-amino-3-methyl-2-oxa-8-azaspiro[4.5]decan-8-yl]-6-bromo-pyrazin-2-yl]methanol (100 mg, 280 umol) in 1,4-dioxane (2 mL) was added K₃PO₄ (119 mg, 560 umol) 1,10-phenanthroline (10 mg, 56 umol) and CuI (5 mg, 27 umol). The mixture was degassed and then heated to 130° C. for 12 hr. After cooling to rt and filtration, the solvent was removed under reduced pressure. The crude residue was purified by prep-HPLC to give 3-({5-[(3S,4S)-4-amino-3-methyl-2-oxa-8-azaspiro[4.5]decan-8-yl]-6-(hydroxymethyl)pyrazin-2-yl}sulfanyl)-2-chlorobenzonitrile (14.3 mg, 32 umol, 11% yield) as a white solid. LCMS (ESI): m/z: [M–H] calculated for C₂₁H₂₃ClN₅O₂S: 444.1; found 444.1; ¹H NMR (400 MHz, METHANOL-d4) δ=8.51 (br s, 1H), 8.20 (s, 1H), 7.72-7.69 (m, 1H), 7.50 (dd, J=1.5, 8.1 Hz, 1H), 7.42-7.36 (m, 1H), 4.63 (s, 2H), 4.31-4.24 (m, 1H), 3.92 (d, J=9.2 Hz, 1H), 3.84-3.66 (m, 3H), 3.34-3.32 (m, 1H), 3.19-3.02 (m, 2H), 1.99-1.80 (m, 3H), 1.71 (br d, J=13.2 Hz, 1H), 1.29 (d, J=6.6 Hz, 3H).

Example 23. Synthesis of 4-({5-[(3S,4S)-4-amino-3-methyl-2-oxa-8-azaspiro[4.5]decan-8-yl]-6-(hydroxymethyl)pyrazin-2-yl}sulfanyl)-3-chloropyridine-2-carbonitrile. (Compound 23)

4-({5-[(3S,4S)-4-amino-3-methyl-2-oxa-8-azaspiro[4.5]decan-8-yl]-6-(hydroxymethyl)pyrazin-2-yl}sulfanyl)-3-chloropyridine-2-carbonitrile was synthesized in a manner similar to 3-({5-[(3S,4S)-4-amino-3-methyl-2-oxa-8-azaspiro[4.5]azaspiro[4.5]decan-8-yl]-6-(hydroxymethyl)pyrazin-2-yl}sulfanyl)-2-chlorobenzonitrile except 2-chloro-3-mercaptobenzonitrile was substituted with 3-chloro-4-sulfanyl-pyridine-2-carbonitrile. LCMS (ESI): m/z: [M+H] calculated for C₂₀H₂₄ClN₆O₂S: 447.1; found 447.2; ¹H NMR (400 MHz, METHANOL-d₄) δ=8.48 (br s, 1H), 8.36 (s, 1H), 8.30 (d, J=5.3 Hz, 1H), 7.13 (d, J=5.3 Hz, 1H), 4.68 (s, 2H), 4.34-4.21 (m, 1H), 3.98-3.93 (m, 1H), 3.87 (br s, 1H), 3.84 (br d, J=8.8 Hz, 1H), 3.36 (br d, J=4.0 Hz, 1H), 3.27-3.09 (m, 3H), 2.01-1.81 (m, 3H), 1.73 (br d, J=12.8 Hz, 1H), 1.30 (d, J=6.6 Hz, 3H).

Example 24. Synthesis of {3-[(3S,4S)-4-amino-3-methyl-2-oxa-8-azaspiro[4.5]decan-8-yl]-6-[(3-chloro-2-methoxypyridin-4-yl)sulfanyl]pyrazin-2-yl}methanol. (Compound 24)

{3-[(3S,4S)-4-amino-3-methyl-2-oxa-8-azaspiro[4.5]decan-8-yl]-6-[(3-chloro-2-methoxypyridin-4-yl)sulfanyl]pyrazin-2-yl}methanol was synthesized in a manner similar to 3-({5-[(3S,4S)-4-amino-3-methyl-2-oxa-8-azaspiro[4.5]decan-8-yl]-6-(hydroxymethyl)pyrazin-2-yl}sulfanyl)-2-chlorobenzonitrile except 2-chloro-3-mercaptobenzonitrile was substituted with 3-chloro-2-methoxy-4-pyridinethiol. LCMS (ESI): m/z: [M+H] calculated for C₂₀H₂₇ClN₅O₃S: 452.1; found 452.2; ¹H NMR (400 MHz, METHANOL-d4) δ=8.49 (s, 1H), 8.32 (s, 1H), 7.80 (d, J=5.5 Hz, 1H), 6.40 (d, J=5.5 Hz, 1H), 4.67 (s, 2H), 4.32-4.25 (m, 1H), 3.99-3.93 (m, 4H), 3.91-3.78 (m, 3H), 3.38 (d, J=4.2 Hz, 1H), 3.39-3.36 (m, 1H), 3.23-3.08 (m, 2H), 2.00-1.84 (m, 3H), 1.73 (br d, J=12.6 Hz, 1H), 1.30 (d, J=6.4 Hz, 3H).

Example 25. Synthesis of {3-[(3S,4S)-4-amino-3-methyl-2-oxa-8-azaspiro[4.5]decan-8-yl]-6-[(2-chloro-3-methoxyphenyl)sulfanyl]pyrazin-2-yl}methanol (Compound 25)

{3-[(3S,4S)-4-amino-3-methyl-2-oxa-8-azaspiro[4.5]decan-8-yl]-6-[(2-chloro-3-methoxyphenyl)sulfanyl]pyrazin-2-yl}methanol was synthesized in a manner similar to 3-({5-[(3S,4S)-4-amino-3-methyl-2-oxa-8-azaspiro[4.5]decan-8-yl]-6-(hydroxymethyl)pyrazin-2-yl}sulfanyl)-2-chlorobenzonitrile except 2-chloro-3-mercaptobenzonitrile was substituted with 2-chloro-3-methoxy-benzenethiol. LCMS (ESI): m/z: [M+H] calculated for C₂₁H₂₈N₄SO₃Cl: 451.1; found 451.2; ¹H NMR (400 MHz, METHANOL-d₄) δ=8.49 (br s, 1H), 7.97 (s, 2H), 7.25-7.17 (m, 2H), 7.04 (dd, J=1.2, 8.3 Hz, 2H), 6.86 (dd, J=1.3, 7.9 Hz, 2H), 4.63 (s, 4H), 4.30-4.24 (m, 2H), 3.95-3.88 (m, 8H), 3.81 (d, J=9.2 Hz, 2H), 3.72-3.58 (m, 4H), 3.37 (d, J=4.2 Hz, 2H), 3.11-2.96 (m, 4H), 1.98-1.82 (m, 6H), 1.72-1.64 (m, 2H), 1.29 (d, J=6.5 Hz, 7H).

Example 26. Synthesis of {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol. (Compound 26)

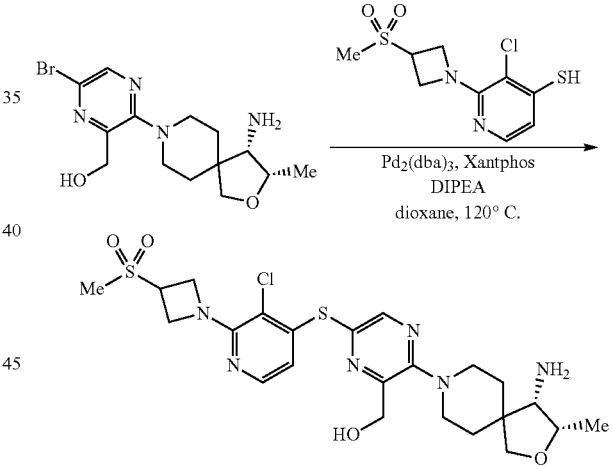

Dioxane (1.4 ml) was added to a mixture of {3-[(3S,4S)-4-amino-3-methyl-2-oxa-8-azaspiro[4.5]decan-8-yl]-6-bromopyrazin-2-yl}methanol (50 mg, 139 μmol), 3-chloro-2-(3-methanesulfonylazetidin-1-yl)pyridine-4-thiol (56 mg, 201 μmol), Xantphos (16 mg, 28 μmol), tris(dibenzylideneacetone) dipalladium (13 mg, 14 μmol). DIPEA (48 μL, 278 μmol) was added. And the heterogeneous mixture was heated to 120° C. under N₂ for 1 hr. After cooling to rt and filtration the solvent was removed under reduced pressure and the crude residue was purified by prep HPLC to give {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol (20.3 mg, 25% yield). LCMS (ESI): m/z [M+H] calculated for C₂₃H₃₂ClN₆O₄S₂: 555.2; found 555.3; ¹H NMR (500 MHz, Methanol-d₄) δ 8.55 (s, 1H), 8.32 (s, 1H), 7.81 (d, J=5.5 Hz, 1H), 6.24 (d, J=5.4 Hz, 1H), 4.69 (d, J=0.4 Hz, 2H), 4.60-4.48 (m, 4H), 4.36-4.26 (m, 2H), 3.95 (d, J=8.9 Hz, 1H), 3.91-3.77 (m, 3H), 3.32 (d, J=4.5 Hz, 1H), 3.23 (ddd, J=13.7, 10.8, 3.1 Hz, 1H), 3.15 (ddd, J=13.6, 10.9, 2.8 Hz, 1H), 3.03 (s, 3H), 2.01-1.91 (m, 2H), 1.90-1.83 (m, 1H), 1.78-1.70 (m, 1H), 1.31 (d, J=6.5 Hz, 3H).

Example 27. Synthesis of {3-[(3S,4S)-4-amino-3-methyl-2-oxa-8-azaspiro[4.5]decan-8-yl]-6-({3-chloro-2-[(oxan-4-yl)amino]pyridin-4-yl}sulfanyl)pyrazin-2-yl}methanol. (Compound 27)

{3-[(3S,4S)-4-amino-3-methyl-2-oxa-8-azaspiro[4.5]decan-8-yl]-6-({3-chloro-2-[(oxan-4-yl)amino]pyridin-4-yl}sulfanyl)pyrazin-2-yl}methanol was synthesized in a manner similar to {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol except 3-chloro-2-(3-methanesulfonylazetidin-1-yl)pyridine-4-thiol was substituted with 3-chloro-2-[(tetrahydro-2H-pyran-4-yl)amino]-4-pyridinethiol. LCMS (ESI): m/z [M+H] calculated for $C_{24}H_{33}ClN_6O_3S$: 521.2; found 521.4; $^1$H NMR (500 MHz, Methanol-d4) δ 8.56 (s, 0H), 8.30 (s, 1H), 7.72 (d, J=5.5 Hz, 1H), 6.05 (d, J=5.6 Hz, 1H), 4.69 (s, 2H), 4.32-4.25 (m, 1H), 4.13 (tt, J=11.0, 4.2 Hz, 1H), 4.04-3.97 (m, 2H), 3.92 (d, J=8.8 Hz, 1H), 3.85-3.72 (m, 3H), 3.56 (td, J=11.8, 2.1 Hz, 2H), 3.29-3.12 (m, 4H), 2.01-1.89 (m, 4H), 1.82 (d, J 13.4 Hz, 1H), 1.78-1.71 (m, 1H), 1.71-1.61 (m, 2H), 1.28 (d, J 6.5 Hz, 3H).

Example 28. Synthesis of 3-({5-[(3S,4S)-4-amino-3-methyl-2-oxa-8-azaspiro[4.5]decan-8-yl]-6-(hydroxymethyl)pyrazin-2-yl}sulfanyl)-2-chloro-N,N-dimethylbenzamide. (Compound 28)

3-({5-[(3S,4S)-4-amino-3-methyl-2-oxa-8-azaspiro[4.5]decan-8-yl]-6-(hydroxymethyl)pyrazin-2-yl}sulfanyl)-2-chloro-N,N-dimethylbenzamide was synthesized in a manner similar to {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol except 3-chloro-2-(3-methanesulfonylazetidin-1-yl)pyridine-4-thiol was substituted with 2-chloro-N,N-dimethyl-3-sulfanylbenzamide. LCMS (ESI): m/z [M+H] calculated for $C_{23}H_{30}ClN_5O_3S$: 492.2; found 492.3; $^1$H NMR (500 MHz, Methanol-d4) δ 8.45 (s, 1H), 8.13 (s, 1H), 7.43-7.34 (m, 2H), 7.30 (dd, J=6.9, 2.3 Hz, 1H), 4.65 (s, 2H), 4.31 (qd, J=6.5, 4.1 Hz, 1H), 3.96 (d, J=9.1 Hz, 1H), 3.90-3.81 (m, 1H), 3.76 (d, J=13.6 Hz, 1H), 3.72-3.65 (m, 1H), 3.44 (d, J=4.2 Hz, 1H), 3.14 (s, 3H), 3.12-3.01 (m, 1H), 2.91 (s, 3H), 1.97 (td, J 12.2, 11.3, 4.0 Hz, 2H), 1.89 (d, J=13.5 Hz, 1H), 1.78-1.69 (m, 1H), 1.33 (d, J=6.5 Hz, 3H).

Example 29. Synthesis of 1-[4-({5-[(3S,4S)-4-amino-3-methyl-2-oxa-8-azaspiro[4.5]decan-8-yl]-6-(hydroxymethyl)pyrazin-2-yl}sulfanyl)-3-chloropyridin-2-yl]azetidin-3-ol. (Compound 29)

1-[4-({5-[(3S,4S)-4-amino-3-methyl-2-oxa-8-azaspiro[4.5]decan-8-yl]-6-(hydroxymethyl)pyrazin-2-yl}sulfanyl)-3-chloropyridin-2-yl]azetidin-3-ol was synthesized in a manner similar to {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol except 3-chloro-2-(3-methanesulfonylazetidin-1-yl)pyridine-4-thiol was substituted with 1-(2-chloro-3-sulfanylphenyl)azetidin-3-ol. LCMS (ESI): m/z [M+H] calculated for $C_{22}H_{30}ClN_6O_3S$: 493.2; found 493.3; $^1$H NMR (500 MHz, Methanol-$d_4$) δ 8.31 (s, 1H), 7.75 (d, J=5.5 Hz, 1H), 6.15 (d, J=5.5 Hz, 1H), 4.69 (s, 2H), 4.62 (tt, J=6.6, 4.7 Hz, 1H), 4.52-4.46 (m, 2H), 4.32-4.24 (m, 1H), 4.01 (ddd, J=9.1, 4.7, 1.2 Hz, 2H), 3.92 (d, J=8.8 Hz, 1H), 3.84-3.73 (m, 3H), 3.26 (ddd, J=13.5, 10.5, 3.1 Hz, 1H), 3.21-3.14 (m, 2H), 1.94 (dddd, J=20.4, 14.0, 10.5, 3.8 Hz, 2H), 1.85-1.78 (m, 1H), 1.77-1.70 (m, 1H), 1.27 (d, J=6.5 Hz, 3H).

Example 30. Synthesis of {3-[(3S,4S)-4-amino-3-methyl-2-oxa-8-azaspiro[4.5]decan-8-yl]-6-[(2,3-dichlorophenyl)sulfanyl]pyrazin-2-yl}methanol. (Compound 30)

{3-[(3S,4S)-4-amino-3-methyl-2-oxa-8-azaspiro[4.5]decan-8-yl]-6-[(2,3-dichlorophenyl)sulfanyl]pyrazin-2-yl}methanol was synthesized in a manner similar to {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol except 3-chloro-2-(3-methanesulfonylazetidin-1-yl)pyridine-4-thiol was substituted with 2,3-dichlorobenzenethiol. LCMS (ESI): m/z [M+H] calculated for $C_{20}H_{24}Cl_2N_4O_2S$: 455.1; found 455.3; $^1$H NMR (500 MHz, Methanol-d4) δ 8.49 (s, 1H), 8.12 (d, J=0.5 Hz, 1H), 7.45 (ddd, J=7.9, 1.6, 0.5 Hz, 1H), 7.21 (td, J=7.9, 0.5 Hz, 1H), 7.15 (ddd, J=8.0, 1.6, 0.5 Hz, 1H), 4.64 (d, J=0.5 Hz, 2H), 4.28 (qd, J=6.5, 4.2 Hz, 1H), 3.94 (d, J=9.1 Hz, 1H), 3.83 (dd, J=9.1, 0.8 Hz, 1H), 3.79-3.64 (m, 2H), 3.41 (d, J=4.2 Hz, 1H), 3.10 (ddd, J=13.8, 11.1, 2.9 Hz, 1H), 3.03 (ddd, J=13.7, 11.2, 2.7 Hz, 1H), 2.66 (d, J=0.5 Hz, 3H), 1.95 (ddt, J=15.1, 11.1, 4.0 Hz, 2H), 1.86 (ddt, J=13.3, 4.7, 2.7 Hz, 1H), 1.72 (dt, J=12.8, 2.3 Hz, 1H), 1.31 (d, J=6.5 Hz, 3H).

Example 31. Synthesis of {6-[(2-amino-3-chloropyridin-4-yl)sulfanyl]-3-[(3S,4S)-4-amino-3-methyl-2-oxa-8-azaspiro[4.5]decan-8-yl]pyrazin-2-yl}methanol. (Compound 31)

{6-[(2-amino-3-chloropyridin-4-yl)sulfanyl]-3-[(3S,4S)-4-amino-3-methyl-2-oxa-8-azaspiro[4.5]decan-8-yl]pyrazin-2-yl}methanol was synthesized in a manner similar to {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}pyrazin-2-yl}methanol except 3-chloro-2-(3-methanesulfonylazetidin-1-yl)pyridine-4-thiol was substituted with 2-amino-3-chloro-4-pyridinethiol. LCMS (ESI): m/z [M+H] calculated for $C_{19}H_{25}ClN_6O_2S$: 437.1; found 437.4; $^1$H NMR (500 MHz, Methanol-d4) δ 8.50 (s, 2H), 8.31 (d, J=2.1 Hz, 1H), 7.62 (dd, J=5.7, 2.1 Hz, 1H), 6.07 (dd, J=5.7, 2.1 Hz, 1H), 4.68 (d, J=2.1 Hz, 2H), 4.33-4.26 (m, 1H), 3.96 (d, J=9.3 Hz, 1H), 3.91-3.77 (m, 4H), 3.40-3.34 (m, 1H), 3.24-3.09 (m, 2H), 1.95 (d, J=12.5 Hz, 2H), 1.88 (d, J=13.3 Hz, 1H), 1.74 (d, J=13.2 Hz, 1H), 1.31 (dd, J=6.5, 2.1 Hz, 3H).

Example 32. Synthesis of {3-[(3S,4S)-4-amino-3-methyl-2-oxa-8-azaspiro[4.5]decan-8-yl]-6-[(2-amino-5-chloropyridin-4-yl)sulfanyl]pyrazin-2-yl}methanol. (Compound 32)

{3-[(3S,4S)-4-amino-3-methyl-2-oxa-8-azaspiro[4.5]decan-8-yl]-6-[(2-amino-5-chloropyridin-4-yl)sulfanyl]pyrazin-2-yl}methanol was synthesized in a manner similar to {3-[(3S,4S)-4-amino-3-methyl-2-oxa-8-azaspiro[4.5]decan-8-yl]-6-{[3-chloro-2-(3-methanesulfonylazetidin-1-yl)

pyridin-4-yl]sulfanyl}pyrazin-2-yl}methanol except 3-chloro-2-(3-methanesulfonylazetidin-1-yl)pyridine-4-thiol was substituted with 2-amino-5-chloro-4-pyridinethiol. LCMS (ESI): m/z [M+H] calculated for $C_{19}H_{25}ClN_6O_2S$: 437.1; found 437.5; $^1$H NMR (500 MHz, Methanol-d4) δ 8.39 (s, 1H), 8.33 (s, 1H), 7.81 (s, 1H), 6.07 (s, 1H), 4.71 (s, 2H), 4.42-4.26 (m, 1H), 3.98 (d, J=9.1 Hz, 1H), 3.94-3.76 (m, 3H), 3.46 (d, J=4.1 Hz, 1H), 3.21-3.08 (m, 2H), 2.07-1.86 (m, 3H), 1.80-1.61 (m, 1H), 1.34 (d, J 6.5 Hz, 3H).

Example 33. Synthesis of [2-[(2-amino-3-chloro-4-pyridyl)sulfanyl]-5-[(3S,4S)-4-amino-3-methyl-2-oxa-8-azaspiro[4.5]decan-8-yl]pyrimidin-4-yl] methanol

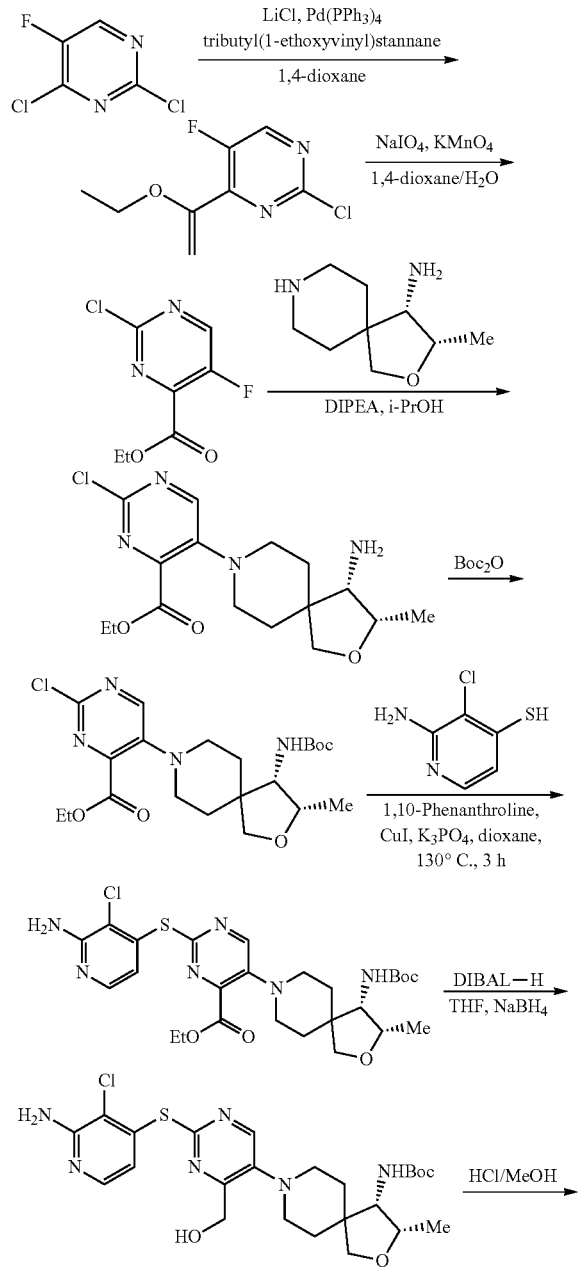

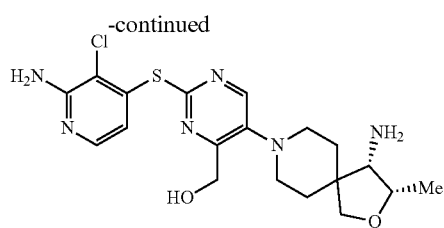

Step 1

To a solution of 2,4-dichloro-5-fluoro-pyrimidine (5 g, 30 mmol) in 1,4-dioxane (70 mL) was added tributyl(1-ethoxyvinyl)tin (9.73 g, 30 mmol, 9.10 mL), LiCl (3.8 g, 90 mmol, 1.84 mL) and Pd(PPh$_3$)$_4$ (1.73 g, 1.5 mmol). The mixture was stirred at 85° C. for 1.5 hrs. The reaction mixture was concentrated under reduced pressure and the resulting residue was purified by column chromatography to afford 2-chloro-4-(1-ethoxyvinyl)-5-fluoro-pyrimidine (3.9 g, 19.2 mmol, 64% yield) as a white solid. $^1$H NMR (400 MHz, Chloroform-d) 6=8.47 (d, J=2.9 Hz, 1H), 5.31 (d, J=3.1 Hz, 1H), 4.72 (d, J=2.9 Hz, 1H), 3.96 (q, J=7.0 Hz, 2H), 1.43 (t, J=6.9 Hz, 3H).

Step 2

To a solution of 2-chloro-4-(1-ethoxyvinyl)-5-fluoro-pyrimidine (3.7 g, 18.4 mmol) in 1,4-dioxane (260 mL) was added a solution of NaIO$_4$ (7.90 g, 37 mmol) in H$_2$O (130 mL). Solid KMnO$_4$ (438 mg, 2.77 mmol) was then added to this solution. The mixture was stirred at 25° C. for 1 hr. The reaction mixture was filtered and the resulting filtrate was diluted with EtOAc (50 mL), aqueous sodium bicarbonate (30 mL) and aqueous NaCl (30 mL). The resulting mixture was stirred for 5 min. The aqueous layer was extracted with EtOAc (50 mL×2) and the combined organic layers were dried over sodium sulfate, filtrated and concentrated under reduced pressure. The resulting residue was purified by column chromatography to afford ethyl 2-chloro-5-fluoro-pyrimidine-4-carboxylate (2.7 g, 13 mmol, 72% yield) as a colorless oil. $^1$H NMR (400 MHz, Chloroform-d) 6=8.70 (d, J=1.8 Hz, 1H), 4.51 (q, J=7.2 Hz, 2H), 1.44 (t, J=7.2 Hz, 3H).

Step 3

To a solution of ethyl 2-chloro-5-fluoro-pyrimidine-4-carboxylate (547 mg, 2.7 mmol) and (3S,4S)-3-methyl-2-oxa-8-azaspiro[4.5]decan-4-amine (650 mg, 2.7 mmol) in i-PrOH (10 mL) was added DIPEA (6.91 g, 53.5 mmol, 9.3 mL). The mixture was stirred at 0° C. for 12 hrs. The reaction mixture was used for next step without purification. LCMS (ESI): m/z: [M+H] calculated for $C_{16}H_{24}ClN_4O_3$: 355.2; found 355.1.

Step 4

To a solution of ethyl 5-[(3S,4S)-4-amino-3-methyl-2-oxa-8-azaspiro[4.5]decan-8-yl]-2-chloro-pyrimidine-4-carboxylate (949 mg, 2.7 mmol) in i-PrOH (5 mL) was added Boc$_2$O (2.92 g, 13.4 mmol, 3.1 mL) and DIPEA (6.9 g, 53.5 mmol, 9.3 mL). The mixture was stirred at 0° C. for 1 hr. The reaction mixture was concentrated under reduced pressure and the resulting residue was purified by prep-HPLC to afford ethyl 5-[(3S,4S)-4-(tert-butoxycarbonylamino)-3- methyl-2-oxa-8-azaspiro[4.5]decan-8-yl]-2-chloro-pyrimidine-4-carboxylate (600 mg, 1.3 mmol, 49% yield) as a yellow solid. LCMS (ESI): m/z: [M+H] calculated for $C_{21}H_{32}ClN_4O_5$: 455.20; found 455.4.

Step 5

To a solution of 2-amino-3-chloro-pyridine-4-thiol (159 mg, 0.99 mmol) and ethyl 5-[(3S,4S)-4-(tert-butoxycarbonylamino)-3-methyl-2-oxa-8-azaspiro[4.5]decan-8-yl]-2-chloro-pyrimidine-4-carboxylate (300 mg, 659 umol) in 1,4-dioxane (5 mL) was added 1,10-Phenanthroline (24 mg, 132 umol), CuI (13 mg, 66 umol) and $K_3PO_4$ (420 mg, 2 mmol) under $N_2$. The mixture was stirred at 130° C. for 3 hrs. The reaction mixture was filtered and the filtrate was concentrated under reduced pressure. The resulting residue was purified by prep-HPLC to afford ethyl 2-[(2-amino-3-chloro-4-pyridyl)sulfanyl]-5-[(3S,4S)-4-(tert-butoxycarbonylamino)-3-methyl-2-oxa-8-azaspiro[4.5]decan-8-yl]pyrimidine-4-carboxylate (180 mg, 311 umol, 47% yield) as a yellow oil. LCMS (ESI): m/z: [M+H] calculated for $C_{26}H_{36}ClN_6O_5S$: 579.2; found 579.3.

Step 6

To a solution of ethyl 2-[(2-amino-3-chloro-4-pyridyl)sulfanyl]-5-[(3S,4S)-4-(tert-butoxycarbonylamino)-3-methyl-2-oxa-8-azaspiro[4.5]decan-8-yl]pyrimidine-4-carboxylate (80 mg, 138 umol) in THF (1 mL) was added DIBAL-H (1 M in toluene, 414.43 uL). The mixture was stirred at −78° C. for 1 hr, and $NaBH_4$ (26 mg, 691 umol) in MeOH (1 mL) was then added to the reaction mixture. The reaction mixture was stirred at 25° C. for 1 hr. The mixture was quenched by the addition of $H_2O$ (2 mL). The mixture was filtered and the resulting filtrate was concentrated under reduced pressure. The remaining residue was purified by prep-HPLC to afford tert-butyl N-[(3S,4S)-8-[2-[(2-amino-3-chloro-4-pyridyl)sulfanyl]-4-(hydroxymethyl)pyrimidin-5-yl]-3-methyl-2-oxa-8-azaspiro[4.5]decan-4-yl]carbamate (40 mg, 75 umol, 54% yield) as a white solid. LCMS (ESI): m/z: [M+H] calculated for $C_{24}H_{34}ClN_6O_4S$: 537.2; found 537.3.

Step 7

A solution of tert-butyl N-[(3S,4S)-8-[2-[(2-amino-3-chloro-4-pyridyl)sulfanyl]-4-(hydroxymethyl)pyrimidin-5-yl]-3-methyl-2-oxa-8-azaspiro[4.5]decan-4-yl]carbamate (27 mg, 50 umol) in HCl/MeOH (4M, 10 mL) was stirred at 0° C. for 3 hr. The reaction mixture was concentrated under reduced pressure. The resulting residue was purified by prep-HPLC to afford [2-[(2-amino-3-chloro-4-pyridyl)sulfanyl]-5-[(3S,4S)-4-amino-3-methyl-2-oxa-8-azaspiro[4.5]decan-8-yl]pyrimidin-4-yl]methanol (2 mg, 4.6 umol, 9% yield) as a white solid. $^1$H NMR (400 MHz, Methanol-$d_4$) δ=8.55 (d, J=19.8 Hz, 1H), 8.35 (s, 1H), 7.83 (d, J=5.4 Hz, 1H), 6.93 (d, J=5.4 Hz, 1H), 4.68 (s, 2H), 4.33-4.22 (m, 1H), 3.92 (d, J=9.2 Hz, 1H), 3.81 (d, J=9.2 Hz, 1H), 3.40 (d, J=4.2 Hz, 1H), 3.23-3.05 (m, 2H), 2.96-2.77 (m, 2H), 2.04-1.83 (m, 3H), 1.73 (d, J=12.7 Hz, 1H), 1.30 (d, J=6.5 Hz, 3H). LCMS (ESI): m/z: [M+H] calculated for $C_{19}H_{26}ClN_6O_2S$: 437.1; found 437.1.

Example 34. Synthesis of (1R)-8-[5-(2,3-dichlorophenyl)-3-(difluoromethyl)pyrazin-2-yl]-8-azaspiro[4.5]decan-1-amine

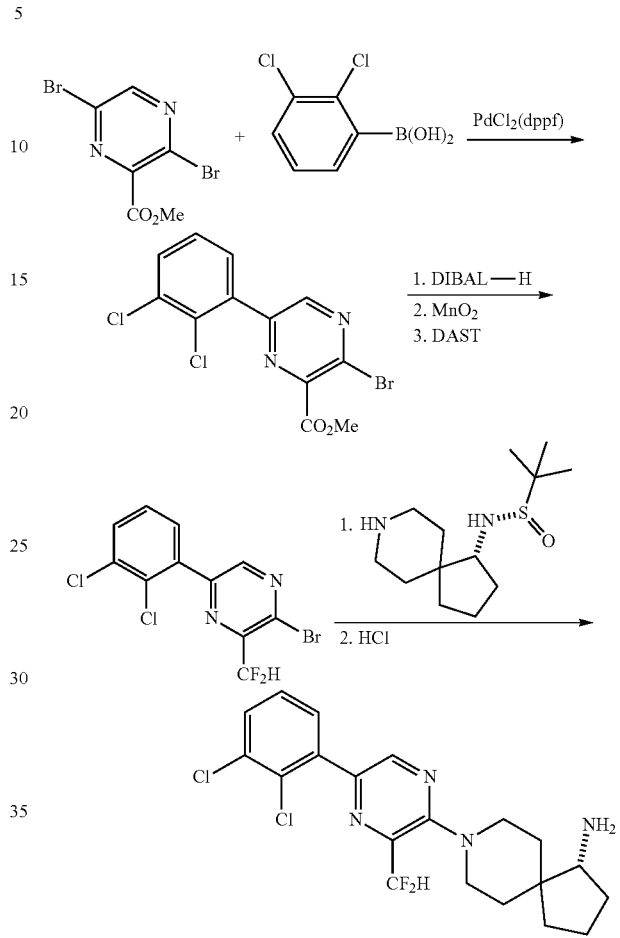

Step 1

To a solution of methyl 3,6-dibromopyrazine-2-carboxylate (583 mg, 1.97 mmol), and (2,3-dichlorophenyl)boronic acid (375 mg, 1.97 mmol) in dioxane (40 ml) was added $Cs_2CO_3$ (1.93 g, 5.91 mmol) in $H_2O$ (10 mL) and $PdCl_2$dppf (144 mg, 0.2 mmol). The reaction was refluxed for 20 min, allowed to cool to rt, and extracted with EtOAc. The combined organic layers were washed with brine and dried over $MgSO_4$. The mixture was concentrated under reduced pressure. Purification by flash chromatography resulted in 370 mg (52%) of the desired product. $^1$H NMR (500 MHz, $CDCl_3$) δ 8.58-8.53 (m, 1H), 7.38-7.32 (m, 1H), 7.29-7.22 (m, 1H), 7.14-7.08 (m, 1H), 3.82-3.76 (m, 3H).

Step 2

To a solution of methyl 3-bromo-6-(2,3-dichlorophenyl)pyrazine-2-carboxylate (270 mg, 0.75 mmol) in THF (5 mL) at −78° C. was added DIBAL-H (2.23 mL, 1 M, 2.23 mmol). The reaction was warmed to rt and stirred for 2 h. The reaction mixture cooled back to 0° C. and quenched with methanol and Rochelle's salt. Extraction with EtOAc, followed by drying over $MgSO_4$ gave (3-bromo-6-(2,3-dichlorophenyl)pyrazin-2-yl)methanol (108 mg, 43%) which was used without further purification in the next step.

Step 3

To a solution of (3-bromo-6-(2,3-dichlorophenyl)pyrazin-2-yl)methanol (224 mg, 0.67 mmol) in CH$_2$Cl$_2$ (5 mL) was added the Dess-Martin reagent (222 mg, 1.0 mmol). The reaction was stirred at rt for 1 h and quenched by addition of aqueous NaHSO$_3$. The mixture was extracted with EtOAc, organic layer was concentrated under reduced pressure, and the combined organic fractions were dried over MgSO$_4$. The resulting solution was filtered through a pad of silica gel to give 3-bromo-6-(2,3-dichlorophenyl)pyrazine-2-carbaldehyde (158 mg, 71%).

Step 4

To a solution of 3-bromo-6-(2,3-dichlorophenyl)pyrazine-2-carbaldehyde (70 mg, 0.21 mmol) in CH$_2$Cl$_2$ (5 mL) was added DAST (101 mg, 0.63 mmol). The reaction was stirred at rt for 1 h, concentrated under reduced pressure, and the resulting residue was purified by filtration through a plug of silica to give the desired 2-bromo-5-(2,3-dichlorophenyl)-3-(difluoromethyl)pyrazine (53 mg, 76%).

Step 5

To a solution of 2-bromo-5-(2,3-dichlorophenyl)-3-(difluoromethyl)pyrazine (50 mg, 0.14 mmol) in DMA (5 mL) was added (S)-2-methyl-N—((R)-8-azaspiro[4.5]decan-1-yl)propane-2-sulfinamide (72.8 mg, 0.28 mmol) and DIPEA (1 mL). The resulting solution was stirred under microwave conditions at 120° C. for 2 h. After cooling to rt the solvent was removed under reduced pressure and the crude residue was purified by flash chromatography to give (S)—N—((R)-8-(5-(2,3-dichlorophenyl)-3-(difluoromethyl)pyrazin-2-yl)-8-azaspiro[4.5]decan-1-yl)-2-methylpropane-2-sulfinamide (44 mg, 59%).

Step 6

To a solution of (S)—N—((R)-8-(5-(2,3-dichlorophenyl)-3-(difluoromethyl)pyrazin-2-yl)-8-azaspiro[4.5]decan-1-yl)-2-methylpropane-2-sulfinamide (35 mg, 0.066 mmol) in methanol (5 mL) was added 1 mL of HCl in dioxane. The resulting solution was stirred at rt for 10 min. After removal of all volatiles under reduced pressure the crude residue was purified by prep-HPLC to give (1R)-8-[5-(2,3-dichlorophenyl)-3-(difluoromethyl)pyrazin-2-yl]-8-azaspiro[4.5]decan-1-amines the formic acid salt (22 mg, 70%). 1H NMR (500 MHz, Methanol-d4) δ 8.82 (t, J=4.3 Hz, 1H), 8.06-7.50 (m, 3H), 7.44-6.82 (m, 1H), 4.36-3.70 (m, 5H), 2.79-1.06 (m, 10H). LC-MS (ESI): m/z [M+H] C$_{20}$H$_{22}$Cl$_2$F$_2$N$_4$ calculated 427.1; found 427.3.

Example 35. Synthesis of (3S,4S)-8-[5-(2,3-dichlorophenyl)-3-(difluoromethyl)pyrazin-2-yl]-3-methyl-2-oxa-8-azaspiro[4.5]decan-4-amine

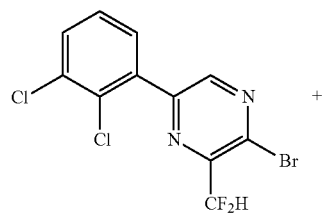

+

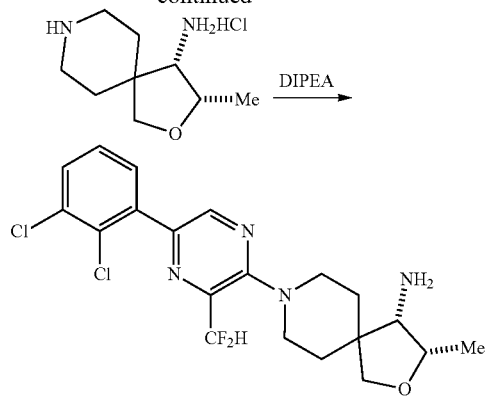

To a solution of 2-bromo-5-(2,3-dichlorophenyl)-3-(difluoromethyl)pyrazine (123 mg, 0.347 mmol, Example 34) in DMA (5 mL) was added (1R,2R)-2-methyl-8-azaspiro[4.5]decan-1-amine hydrochloride (168 mg, 0.694 mmol) and DIPEA (1 mL). The resulting solution was stirred under microwave conditions at 120° C. for 2 h. After cooling to rt the resulting mixture was concentrated under reduced pressure and the residue was purified by prep-HPLC to provide (3S,4S)-8-[5-(2,3-dichlorophenyl)-3-(difluoromethyl)pyrazin-2-yl]-3-methyl-2-oxa-8-azaspiro[4.5]decan-4-amine as the formate salt (30 mg, 18%). $^1$H NMR (500 MHz, Methanol-d$_4$) 8.63 (s, 1H), 7.65-7.42 (m, 3H), 6.93 (t, J=50 Hz, 1H, CF$_2$H), 4.34 (m, 1H), 4.02-3.19 (m, 7H), 2.68-1.94 (4H), 1.36 (d, J=5.0 Hz, 3H); LC-MS (ESI): m/z [M+H] C$_{20}$H$_{22}$C$_2$F$_2$N$_4$O calculated 443.1; found 443.3.

Biological Examples—SHP2 Allosteric Inhibition Assay

Without wishing to be bound by theory, SHP is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The phosphatase reactions were performed at room temperature in 96-well black polystyrene plate, flat bottom, non-binding surface (Corning, Cat #3650) using a final reaction volume of 100 μL and the following assay buffer conditions: 50 mM HEPES, pH 7.2, 100 mM NaCl, 0.5 mM EDTA, 0.05% P-20, 1 mM DTT.

The inhibition of SHP2 by compounds of the present disclosure (concentrations varying from 0.00005-10 μM) was monitored using an assay in which 0.2 nM of SHP2 was incubated with 0.5 μM of Activating Peptide 1 (sequence: H$_2$N-LN(pY)IDLDLV(dPEG8)LST(pY)ASINFQK-amide) or Activating Peptide 2 (sequence: H$_2$N-LN(pY)AQLWHA(dPEG8)LTI(pY)ATIRRF-amide). After 30-60-minutes incubation at 25° C., the surrogate substrate DiFMUP (Invitrogen, Cat #D6567) was added to the reaction and activity was determined by a kinetic read using a microplate reader (Envision, Perkin-Elmer or Spectramax M5, Molecular Devices). The excitation and emission wavelengths were 340 nm and 450 nm, respectively. Initial rates were determined from a linear fit of the data, and the inhibitor dose response curves were analyzed using normalized IC$_{50}$ regression curve fitting with control based normalization.

Using the above-protocol, SHP2 inhibition measured as set forth in Table 1.

TABLE 1

| SHP2 Inhibition of Tested Compounds | |
|---|---|
| Compound | SHP2 IC50, nM |
| Compound 1 (Example 1) | 145 |
| Compound 2 (Example 2) | 88 |
| Compound 3 (Example 3) | 461 |

Using the above-protocol, SHP2 inhibition measured as set forth in Table 2. In the table below: "+++" refers to <=50 nM; "++' refers to >50 nM to <=500 nM; and "+" refers to >500 nM.

TABLE 2

| Compound | Structure | Exact mass (g/mol) and Chemical formula | SHP2 Allosteric IC50 (nM) |
|---|---|---|---|
| 1 | [structure] | 407.128<br>C$_{19}$H$_{23}$Cl$_2$N$_5$O | ++ |
| 2 | [structure] | 406.1327<br>C$_{20}$H$_{24}$Cl$_2$N$_4$O | ++ |
| 3 | [structure] | 366.1014<br>C$_{17}$H$_{20}$Cl$_2$N$_4$O | ++ |
| 4 | [structure] | 380.1186<br>C$_{16}$H$_{21}$ClN$_6$OS | +++ |

TABLE 2-continued

SHP2 Inhibition of Tested Compounds

| Compound | Structure | Exact mass (g/mol) and Chemical formula | SHP2 Allosteric IC50 (nM) |
|---|---|---|---|
| 5 | 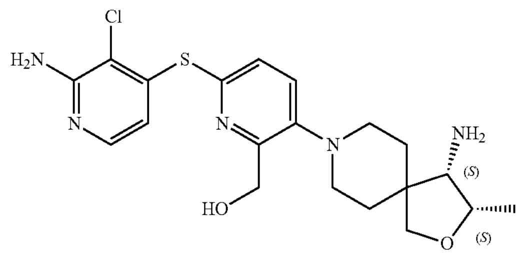 | 435.1<br>$C_{20}H_{26}ClN_5O_2S$ | +++ |
| 6 | 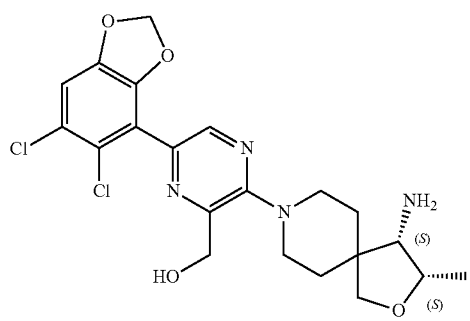 | 466.1175<br>$C_{21}H_{24}Cl_2N_4O_4$ | ++ |
| 7 | 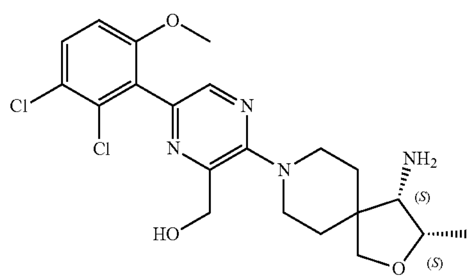 | 452.1382<br>$C_{21}H_{26}Cl_2N_4O_3$ | + |
| 8 | 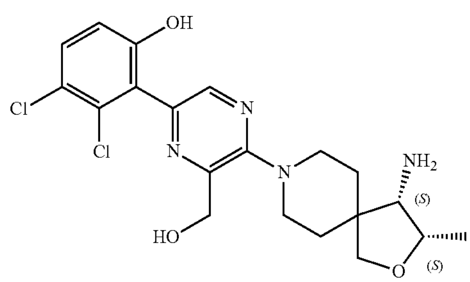 | 438.1225<br>$C_{20}H_{24}Cl_2N_4O_3$ | ++ |
| 9 | 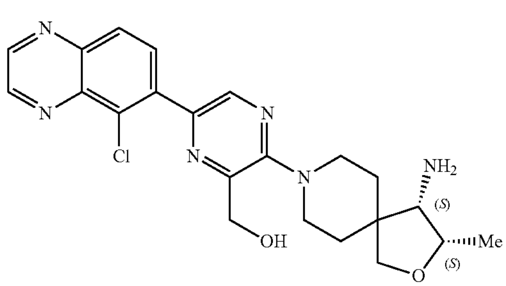 | 440.1728<br>$C_{22}H_{25}ClN_6O_2$ | ++ |

TABLE 2-continued

SHP2 Inhibition of Tested Compounds

| Compound | Structure | Exact mass (g/mol) and Chemical formula | SHP2 Allosteric IC50 (nM) |
|---|---|---|---|
| 10 | 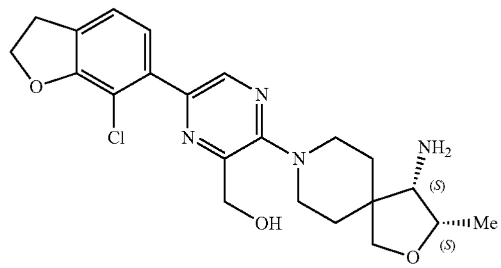 | 430.1772 $C_{22}H_{27}ClN_4O_3$ | ++ |
| 11 | 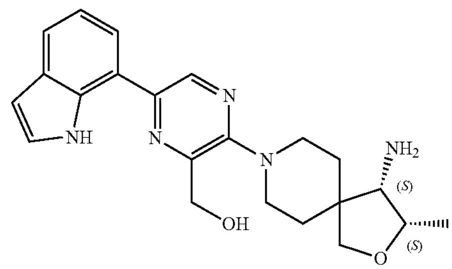 | 393.2165 $C_{22}H_{27}N_5O_2$ | +++ |
| 12 | 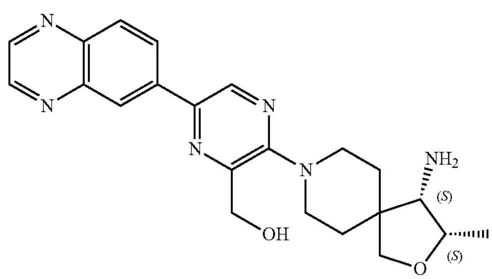 | 406.2117 $C_{22}H_{26}N_6O_2$ | + |
| 13 | 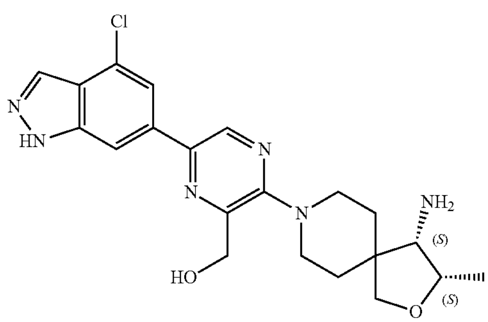 | 428.1728 $C_{21}H_{25}ClN_6O_2$ | ++ |
| 14 | 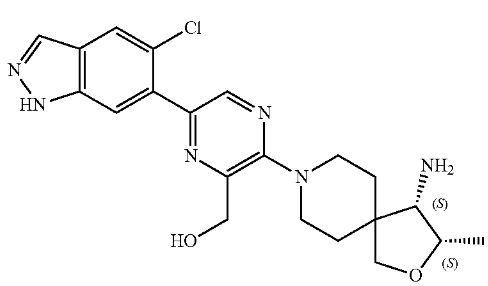 | 428.1728 $C_{21}H_{25}ClN_6O_2$ | ++ |

TABLE 2-continued

SHP2 Inhibition of Tested Compounds

| Compound | Structure | Exact mass (g/mol) and Chemical formula | SHP2 Allosteric IC50 (nM) |
|---|---|---|---|
| 15 | 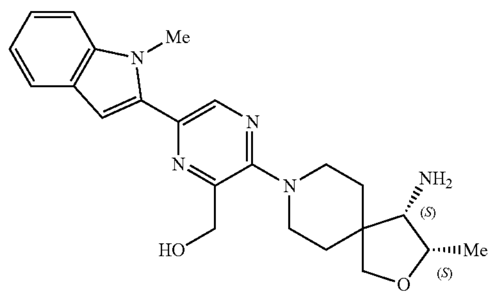 | 407.2321 $C_{23}H_{29}N_5O_2$ | +++ |
| 16 | 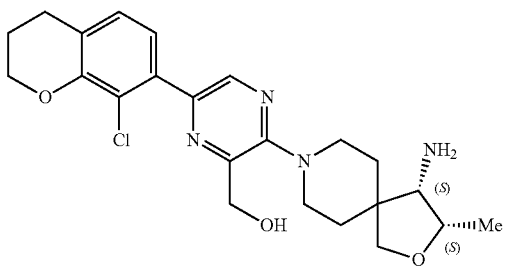 | 444.1928 $C_{23}H_{29}ClN_4O_3$ | ++ |
| 17 | 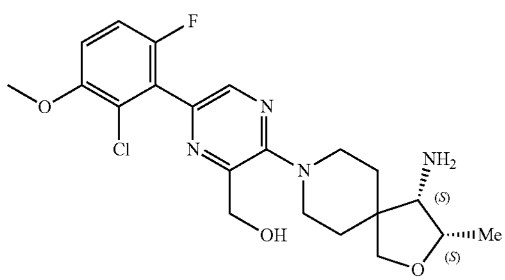 | 436.1677 $C_{21}H_{26}ClFN_4O_3$ | + |
| 18 | 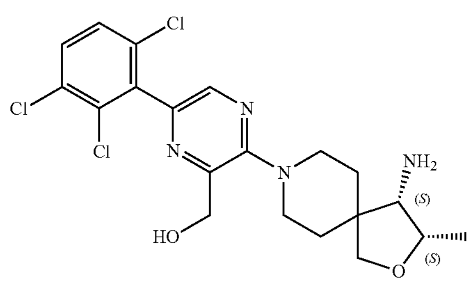 | 456.0887 $C_{20}H_{23}Cl_3N_4O_2$ | ++ |
| 19 | 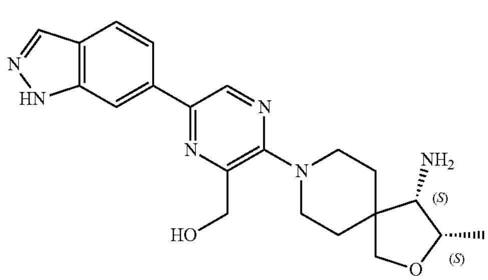 | 394.2117 $C_{21}H_{26}N_6O_2$ | +++ |

TABLE 2-continued

SHP2 Inhibition of Tested Compounds

| Compound | Structure | Exact mass (g/mol) and Chemical formula | SHP2 Allosteric IC50 (nM) |
|---|---|---|---|
| 20 | 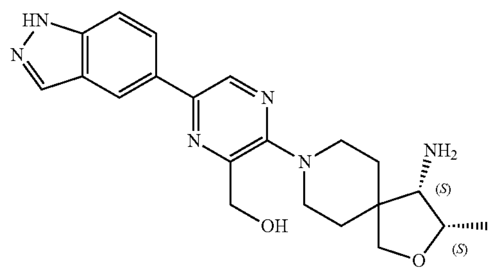 | 394.2117 $C_{21}H_{26}N_6O_2$ | ++ |
| 21 | 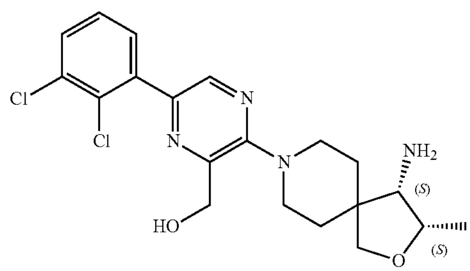 | 422.1276 $C_{20}H_{24}Cl_2N_4O_2$ | +++ |
| 22 | 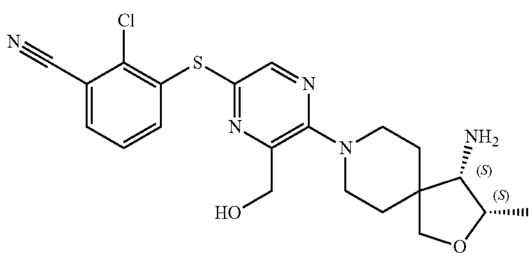 | 445.1339 $C_{21}H_{24}ClN_5O_2S$ | +++ |
| 23 | 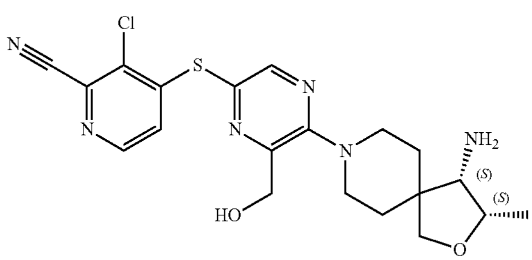 | 446.1292 $C_{20}H_{23}ClN_6O_2S$ | +++ |
| 24 | 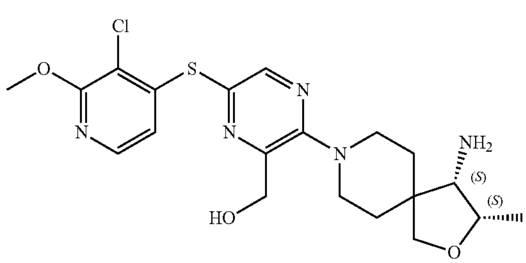 | 451.1445 $C_{20}H_{26}ClN_5O_3S$ | +++ |

TABLE 2-continued

SHP2 Inhibition of Tested Compounds

| Compound | Structure | Exact mass (g/mol) and Chemical formula | SHP2 Allosteric IC50 (nM) |
|---|---|---|---|
| 25 | 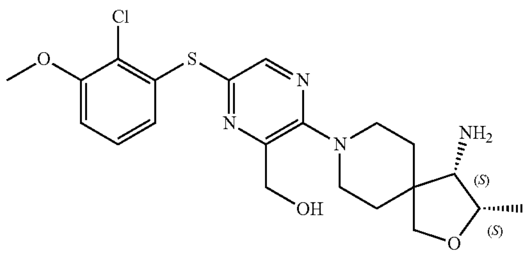 | 450.1492<br>$C_{21}H_{27}ClN_4O_3S$ | +++ |
| 26 | 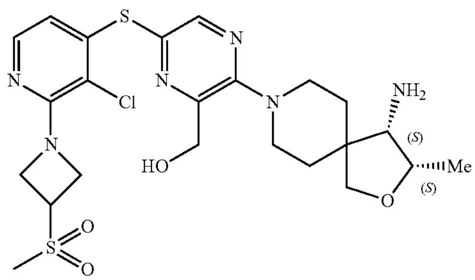 | 554.1537<br>$C_{23}H_{31}ClN_6O_4S_2$ | +++ |
| 27 | 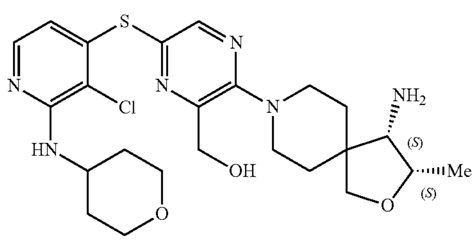 | 520.2023<br>$C_{24}H_{33}ClN_6O_3S$ | +++ |
| 28 | 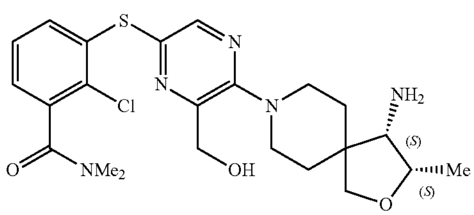 | 491.1758<br>$C_{23}H_{30}ClN_5O_3S$ | +++ |
| 29 | 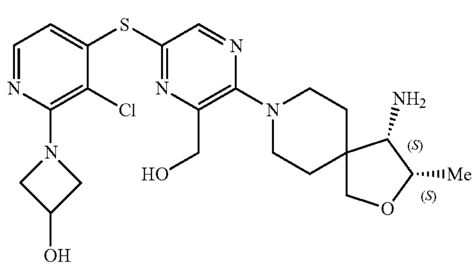 | 492.171<br>$C_{22}H_{29}ClN_6O_3S$ | +++ |
| 30 | 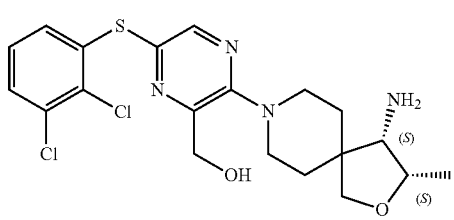 | 454.0997<br>$C_{20}H_{24}Cl_2N_4O_2S$ | +++ |

TABLE 2-continued

SHP2 Inhibition of Tested Compounds

| Compound | Structure | Exact mass (g/mol) and Chemical formula | SHP2 Allosteric IC50 (nM) |
|---|---|---|---|
| 31 | 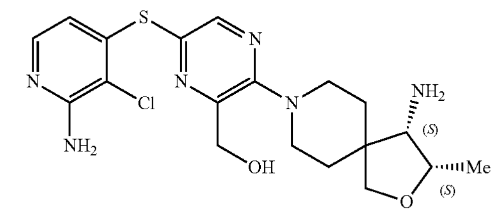 | 436.1448<br>$C_{19}H_{25}ClN_6O_2S$ | +++ |
| 32 | 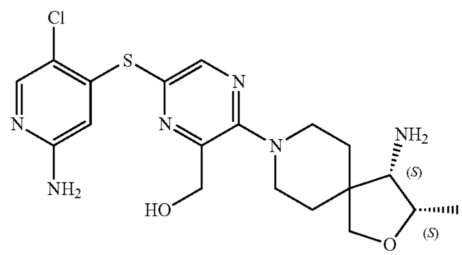 | 436.1448<br>$C_{19}H_{25}ClN_6O_2S$ | +++ |
| 33 | 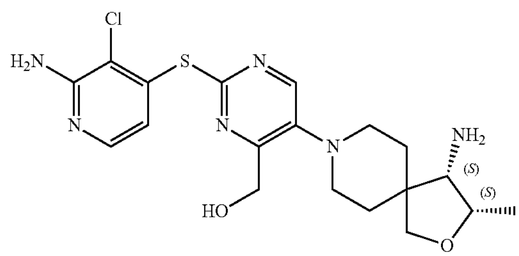 | 436.9<br>$C_{19}H_{25}ClN_6O_2S$ | |
| 34 | 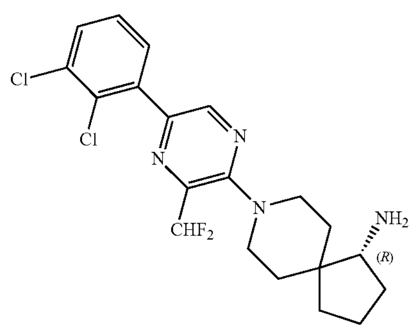 | 426.1<br>$C_{20}H_{22}Cl_2F_2N_4$ | ++ |
| 35 | 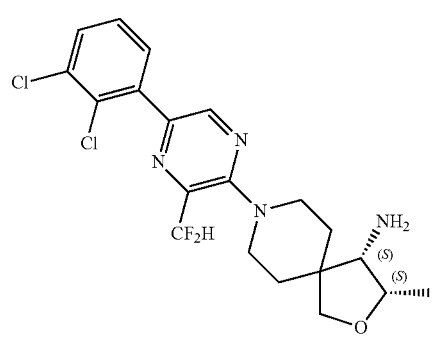 | 443.3<br>$C_{20}H_{22}Cl_2F_2N_4O$ | ++ |

In some embodiments, compounds of the disclosure tested in the assay described above demonstrated an activity of less than 1000 nM. In some embodiments, compounds of the disclosure tested in the assay described above demonstrated an activity of about 10 nM to about 100 nM. In some embodiments, compounds of the disclosure tested in the assay described above demonstrated an activity of 10 nM to 100 nM. In some embodiments, compounds of the disclosure tested in the assay described above demonstrated an activity of less than 10 nM.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 1 nM to about 10 nM of a compound of the disclosure. In some embodiments, SHP2 is inhibited after treatment with about 10 nM to about 100 nM of a compound of the disclosure. In some embodiments, SHP2 is inhibited after treatment with about 100 nM to about 10 μM of a compound of the disclosure.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A compound, or a pharmaceutically acceptable salt, solvate, hydrate, or stereoisomer thereof, selected from the group consisting of

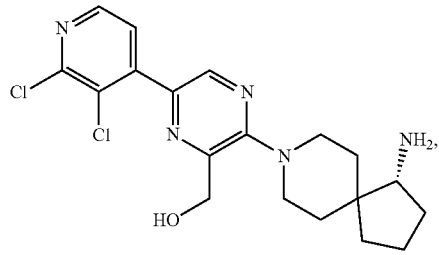

(1)

(2)

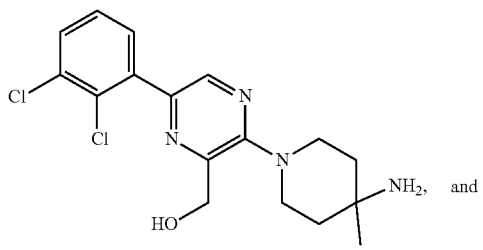

(3)

(4)

2. A compound, or a pharmaceutically acceptable salt, solvate, hydrate, or stereoisomer thereof, selected from the group consisting of

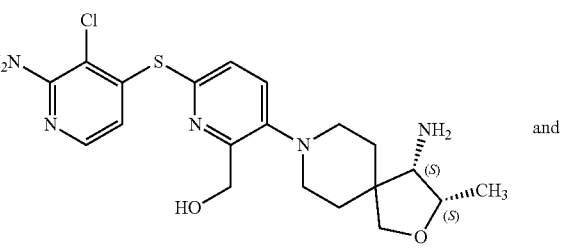

(5)

(5a)

3. A compound, or a pharmaceutically acceptable salt, solvate, hydrate, or stereoisomer thereof, selected from the group consisting of

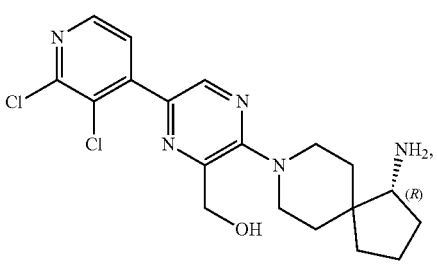

(1)

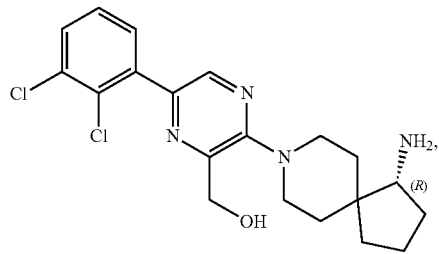
(2)
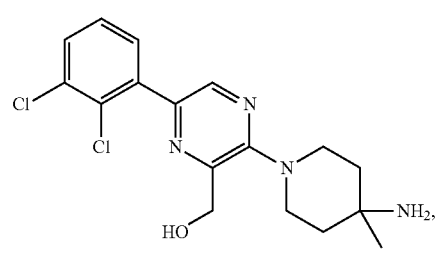
(3)
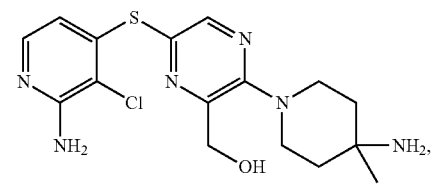
(4)
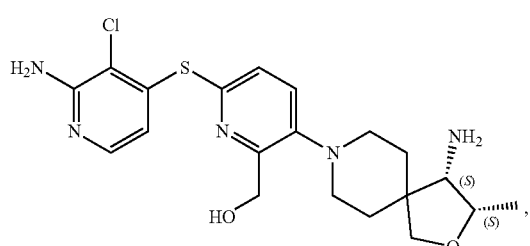
(5)
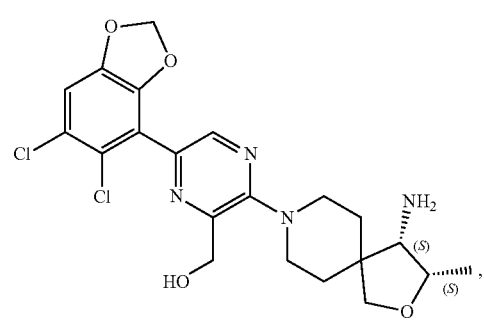
(6)
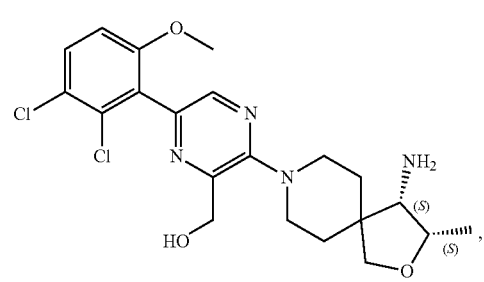
(7)
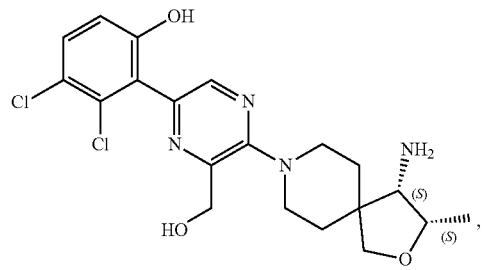
(8)
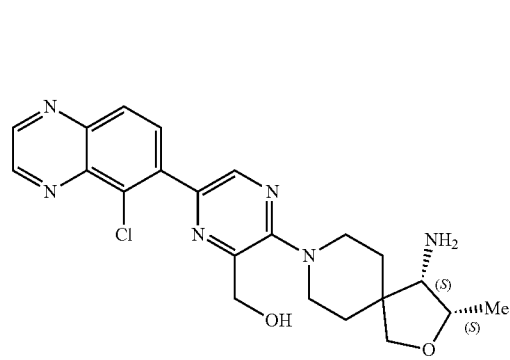
(9)
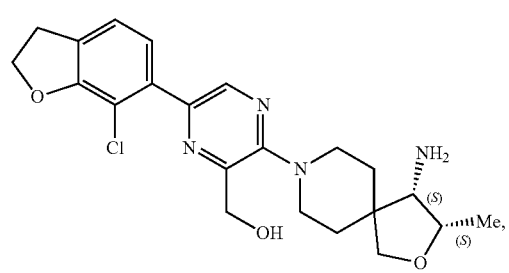
(10)
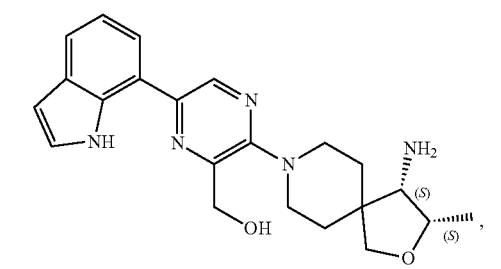
(11)
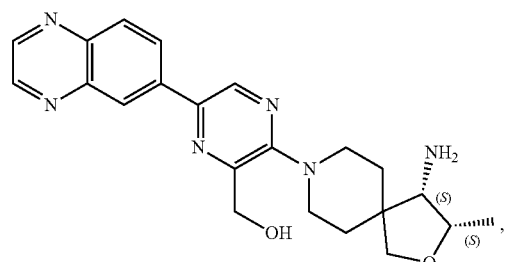
(12)

(13)
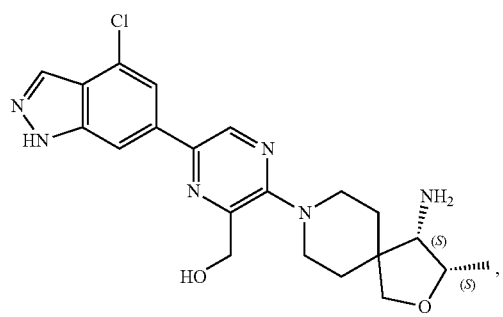
(14)
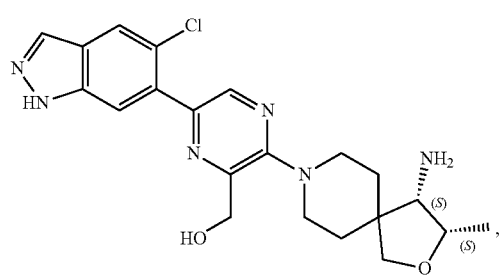
(15)
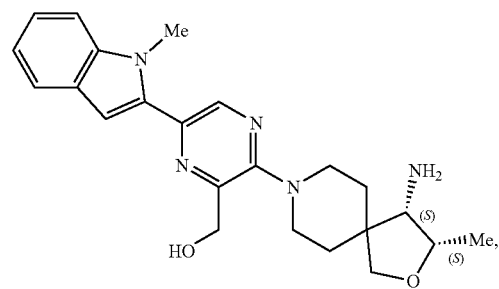
(16)
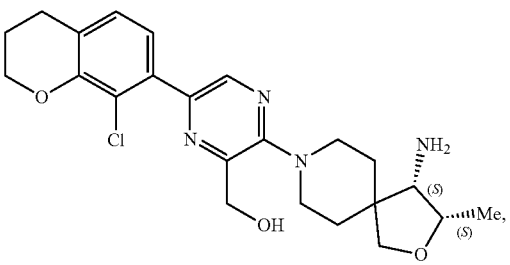
(17)
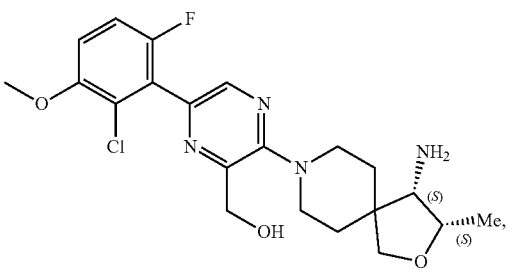
(18)
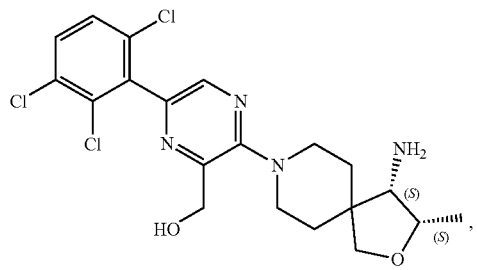
(19)
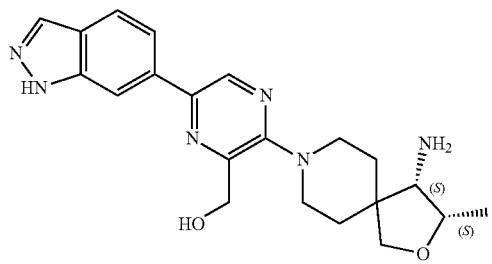
(20)
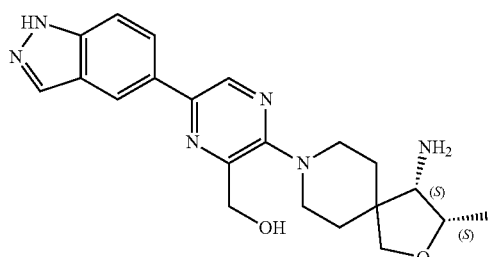
(21)
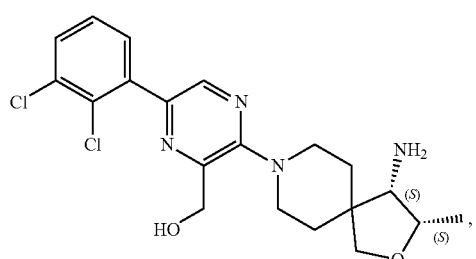
(22)
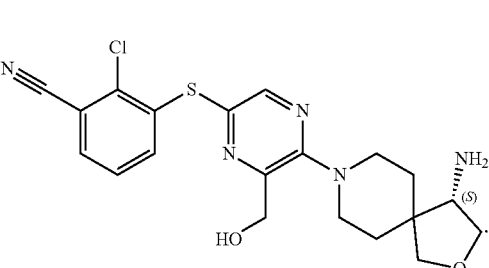
(23)
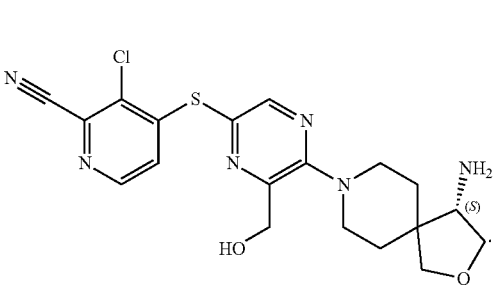

(24)
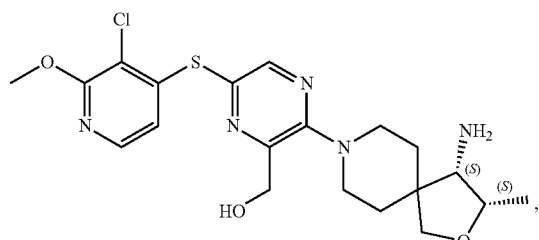

(25)
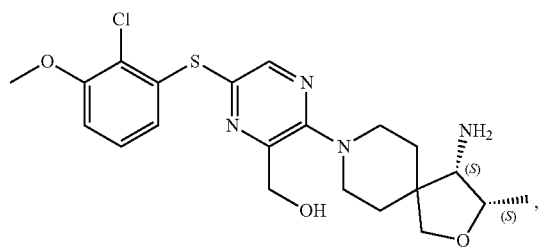

(26)
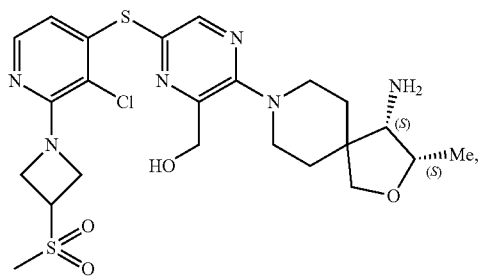

(27)
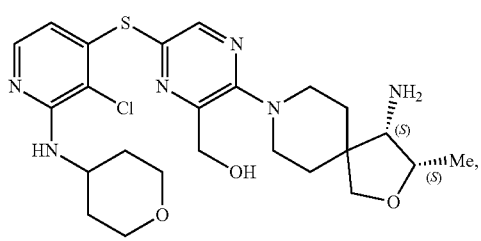

(28)
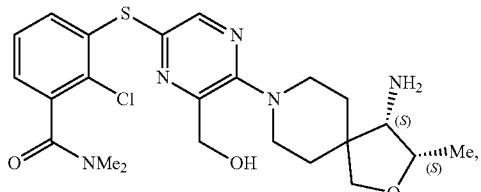

(29)
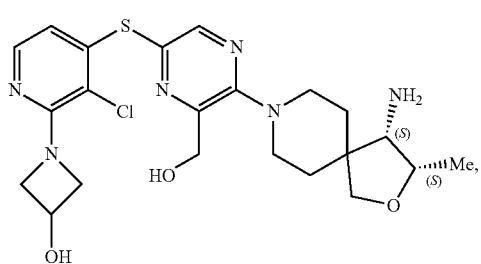

(30)
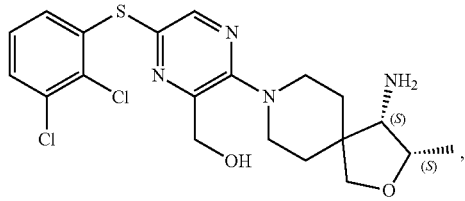

(31)
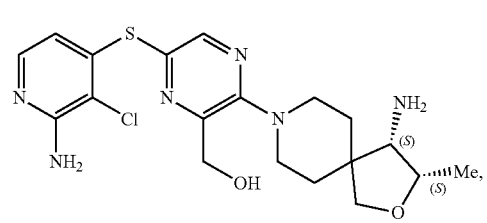

(32)
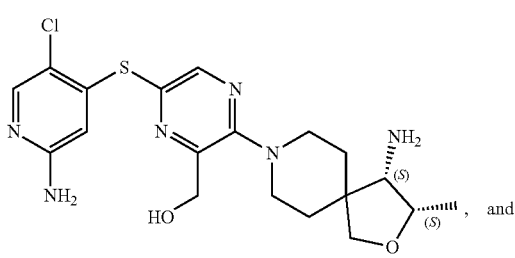

and

(33)
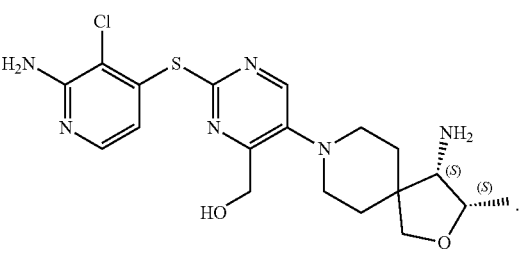

4. A pharmaceutical composition comprising a compound of claim 1, or a pharmaceutically acceptable salt, solvate, hydrate, or stereoisomer thereof, and a pharmaceutically acceptable carrier.

5. A pharmaceutical composition comprising a compound of claim 2, or a pharmaceutically acceptable salt, solvate, hydrate, or stereoisomer thereof, and a pharmaceutically acceptable carrier.

6. A pharmaceutical composition comprising a compound of claim 3, or a pharmaceutically acceptable salt, solvate, hydrate, or stereoisomer thereof, and a pharmaceutically acceptable carrier.

* * * * *